United States Patent
Kashi et al.

(10) Patent No.: US 11,692,166 B2
(45) Date of Patent: Jul. 4, 2023

(54) COMPOSITIONS AND METHODS FOR IMPROVING ALCOHOL TOLERANCE IN YEAST

(71) Applicant: Technion Research & Development Foundation Limited, Haifa (IL)

(72) Inventors: Yechezkel Kashi, D.N. Megiddo (IL); Roni Haas, Haifa (IL); Inbar Kesten, Haifa (IL); Keren Buhnik-Rosenblau, Kibbutz Usha (IL); Guy Horev, Kiryat-Tivon (IL)

(73) Assignee: Technion Research & Development Foundation Limited, Haifa (IL)

( * ) Notice: Subject to any disclaimer, the term of this patent is extended or adjusted under 35 U.S.C. 154(b) by 427 days.

(21) Appl. No.: 16/640,072

(22) PCT Filed: Aug. 23, 2018

(86) PCT No.: PCT/IL2018/050935
§ 371 (c)(1),
(2) Date: Feb. 19, 2020

(87) PCT Pub. No.: WO2019/038771
PCT Pub. Date: Feb. 28, 2019

(65) Prior Publication Data
US 2020/0199524 A1    Jun. 25, 2020

Related U.S. Application Data

(60) Provisional application No. 62/549,062, filed on Aug. 23, 2017.

(51) Int. Cl.
| | | |
|---|---|---|
| *C12N 1/36* | (2006.01) | |
| *C12N 1/16* | (2006.01) | |
| *C12P 7/06* | (2006.01) | |
| *C12Q 1/6895* | (2018.01) | |

(52) U.S. Cl.
CPC .............. *C12N 1/16* (2013.01); *C12N 1/36* (2013.01); *C12Q 1/6895* (2013.01)

(58) Field of Classification Search
CPC .......... C12N 1/16; C12N 1/36; C12Q 1/6895; C12P 7/06
See application file for complete search history.

(56) References Cited

FOREIGN PATENT DOCUMENTS

| WO | WO 2012143513 A2 * | 10/2012 | ........... C07K 14/395 |
|---|---|---|---|
| WO | WO 2012/175552 | 12/2012 | |
| WO | WO 2019/038771 | 2/2019 | |

OTHER PUBLICATIONS

Thammasittirong et al., "Improvement of ethanol production by ethanol-tolerant *Saccharomyces cerevisiae* UVNR56", SpringerPlus 2013, 2:583 (doi:10.1186/2193-1801-2-583) total pp. 1-5. (Year: 2013).*

Hua et al. 2012—CN 102373160 A—"A High Sugar, High Alcohol and High Acid *Saccharomyces cerevisiae* ATCC9763 Filtering and Application", English translation document, total pp. 1-7. (Year: 2012).*

International Preliminary Report on Patentability dated Mar. 5, 2020 From the International Bureau of WIPO Re. Application No. PCT/IL2018/050935. (10 Pages).

International Search Report and the Written Opinion dated Jan. 18, 2019 From the International Searching Authority Re. Application No. PCT/IL2018/050935. (18 Pages).

Invitation to Pay Additional Fees, Communication Relating to the Results of the Partial International Search and the Provisional Opinion dated Nov. 27, 2018 dated Nov. 27, 2018 From the International Searching Authority Re. Application No. PCT/IL2018/050935. (15 Pages).

Swinnen et al. "Identification of Novel Causative Genes Determining the Complex Trait of High Ethanol Tolerance in Yeast Using Pooled-Segregant Whole-Genome Sequence Analysis", Genome Research, XP009162009, 22(5): 975-984, May 2012. Abstract, p. 975, col. 2, Para 2, p. 982, col. 1, Para 1.

Voordeckers et al. "Adaptation to High Ethanol Reveals Complex Evolutionary Pathways", PLOS Genetics, XP055317207, 11(11): e1005635-1-e1005635-31, Nov. 6, 2015. Abstract, p. 14.

* cited by examiner

*Primary Examiner* — Satyendra K Singh

(57) ABSTRACT

Yeast strains are disclosed that are capable of surviving high ethanol concentrations and propagating in high ethanol concentrations. Genes that are involved in ethanol tolerance are disclosed as well.

12 Claims, 17 Drawing Sheets
(16 of 17 Drawing Sheet(s) Filed in Color)
Specification includes a Sequence Listing.

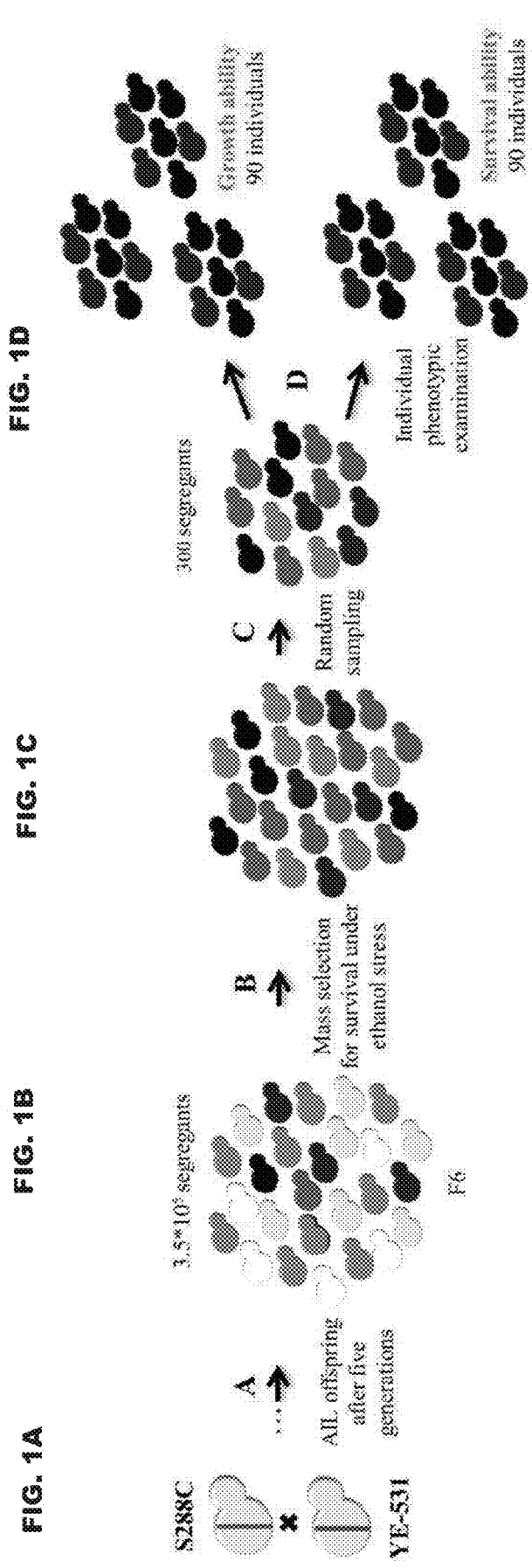

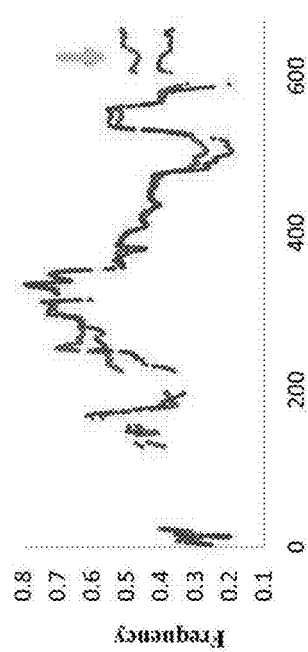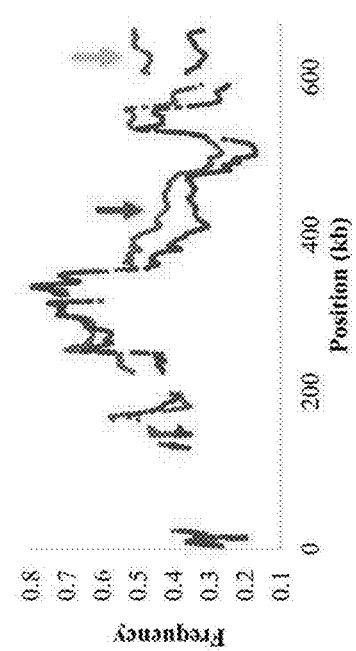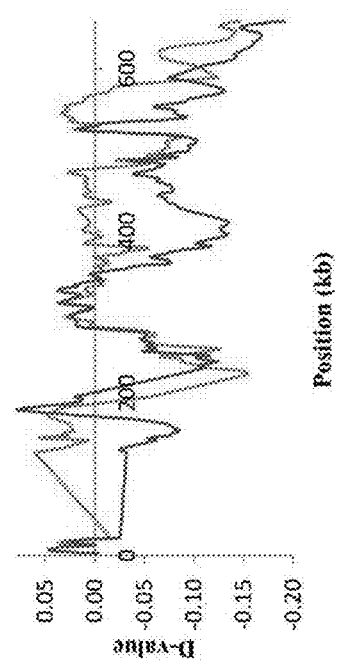
FIG. 4A
FIG. 4B
FIG. 4C

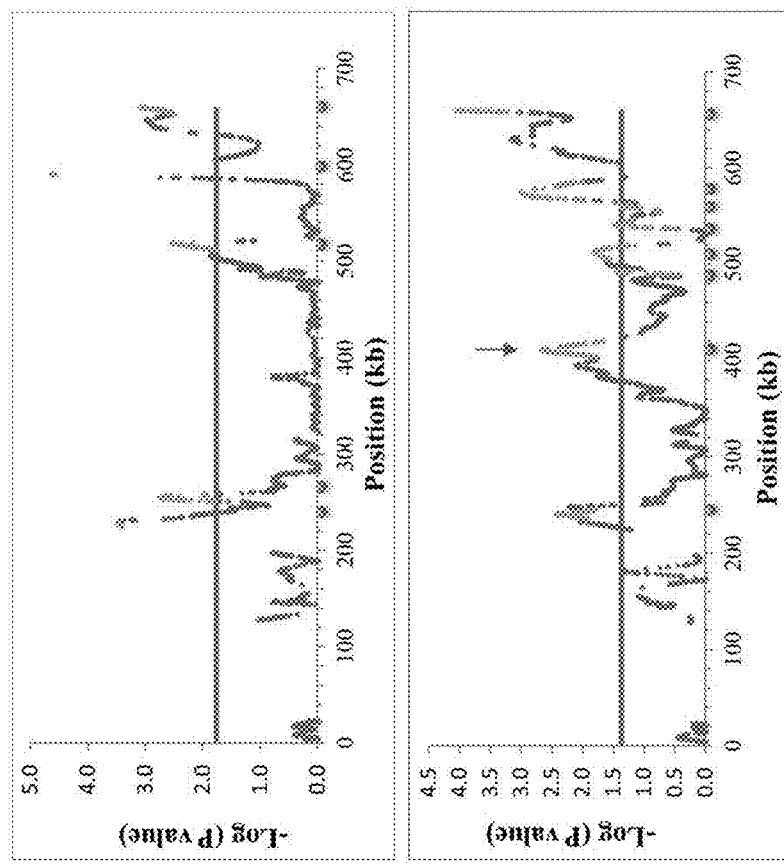

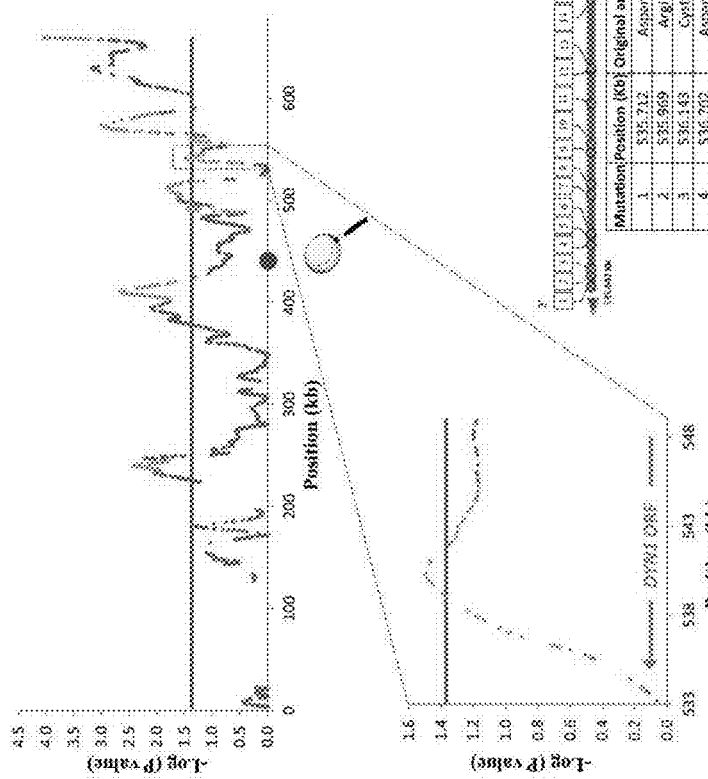
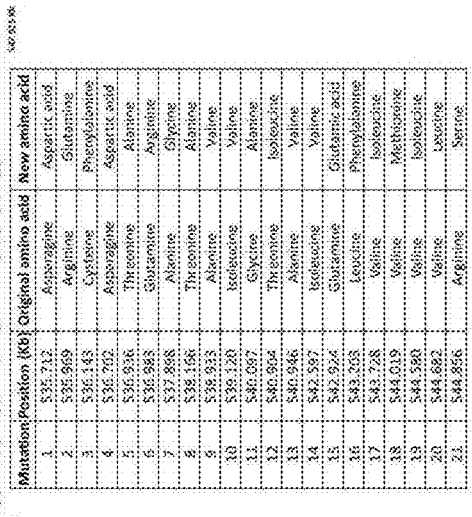
FIG. 6A
FIG. 6B
FIG. 6C

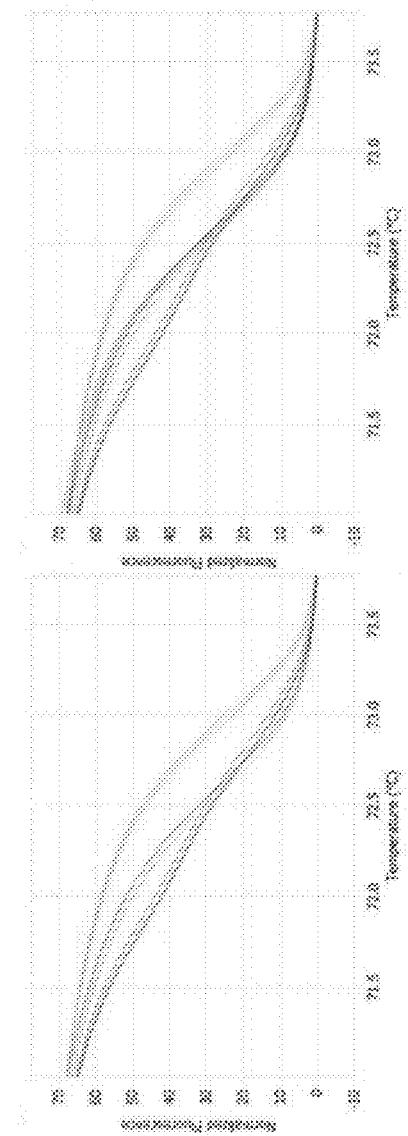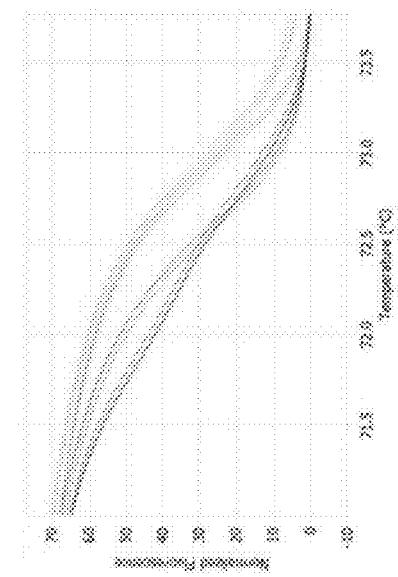
FIG. 10A
FIG. 10B
FIG. 10C

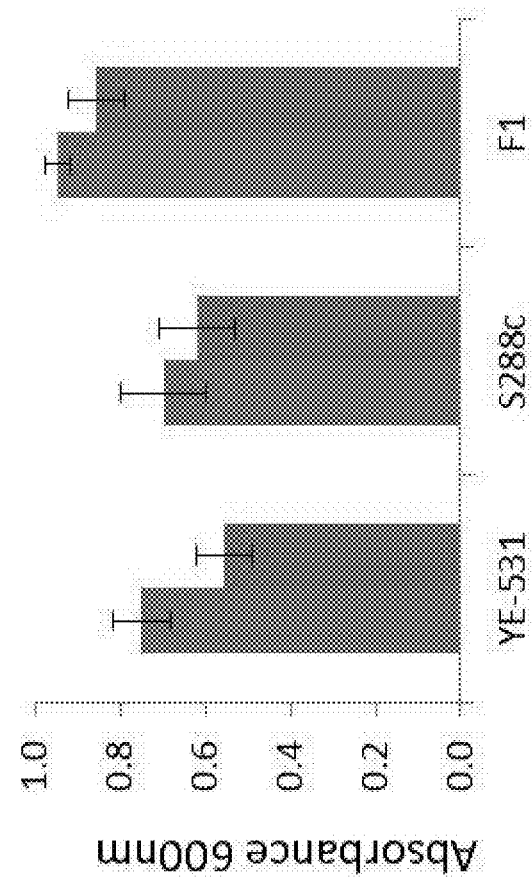
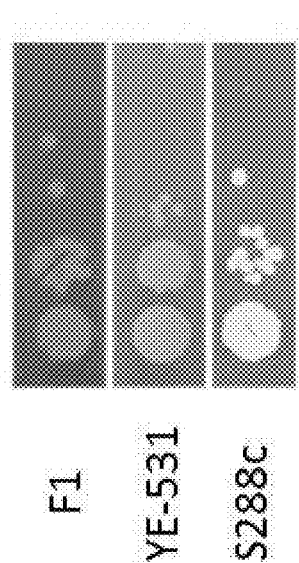
FIG. 13B
FIG. 13A

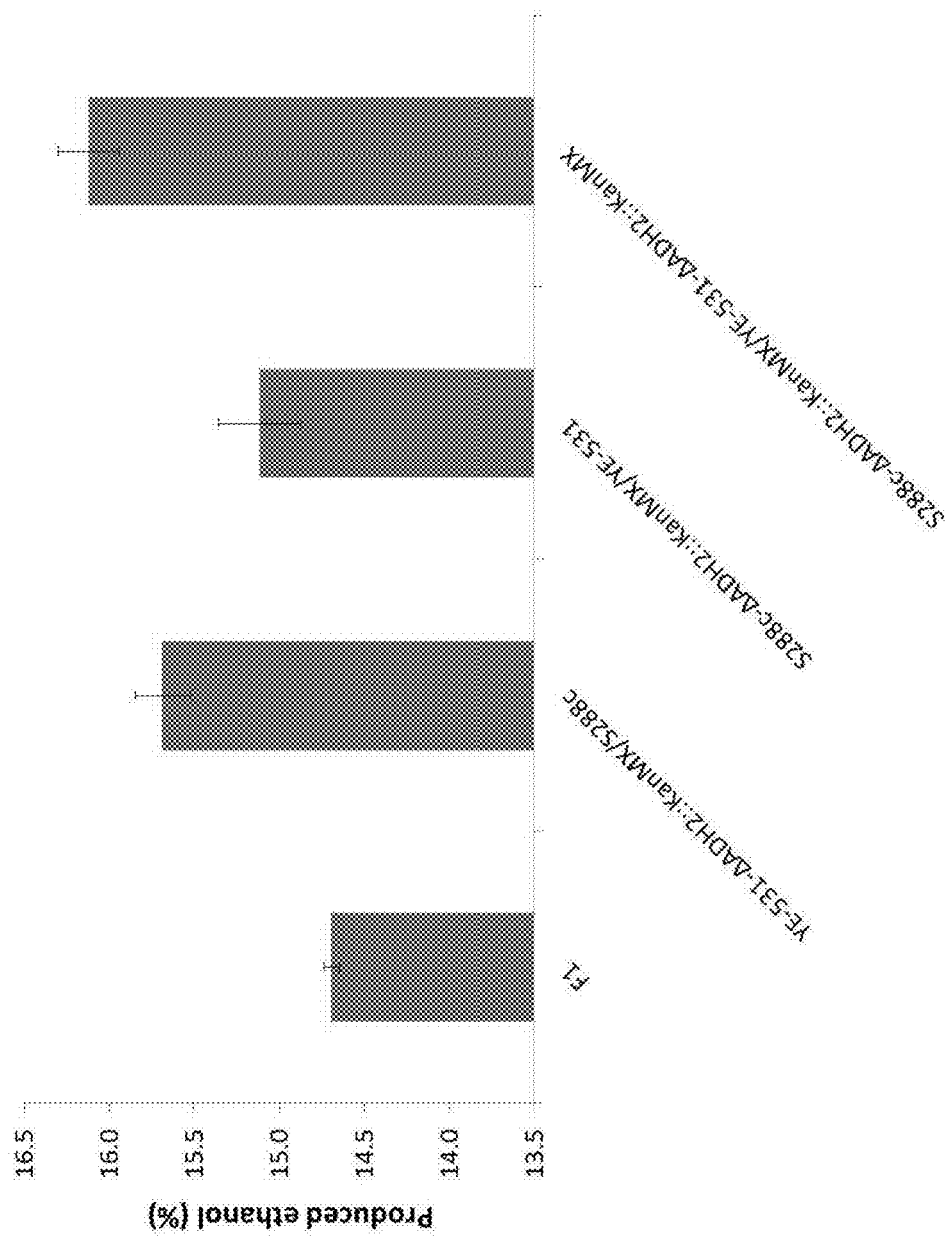

```
                         SEQUENCE LISTING

<160> NUMBER OF SEQ ID NOS: 207

<210> SEQ ID NO 1
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 1
gcgcttgtag gaactgtt                                                  18

<210> SEQ ID NO 2
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 2
gacgatttag agtaaggtc                                                 19

<210> SEQ ID NO 3
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 3
gcattagctc gatgacttag                                                20
```

<210> SEQ ID NO 4
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 4
cagtctcgga caataaatac gc                                            22

<210> SEQ ID NO 5
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 5
catgtgttga tagcaggtga cg                                            22

<210> SEQ ID NO 6
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 6
ctattctagt acttccctgc tg                                            22

<210> SEQ ID NO 7
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 7
gatgccagga aataaatgcg                                               20

<210> SEQ ID NO 8
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 8
gaatgatatt ctaggccctg                                               20

<210> SEQ ID NO 9
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 9
gacattcaat catcggttgc                                               20

<210> SEQ ID NO 10
<211> LENGTH: 20
<212> TYPE: DNA
<213> ORGANISM: Artificial sequence
<220> FEATURE:

<223> OTHER INFORMATION: Single strand DNA oligonucleotide

<400> SEQUENCE: 10
caatgccgcg tctacaattc                                          20

<210> SEQ ID NO 11
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 11
gaatgccgag ataggataac                                          20

<210> SEQ ID NO 12
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 12
caccttcttg ttgttcaaac                                          20

<210> SEQ ID NO 13
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 13
gctatagcat gcctatcac                                           19

<210> SEQ ID NO 14
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 14
tcactcgtgc tagcaaac                                            18

<210> SEQ ID NO 15
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 15
ggactgactc cttcatcgc                                           19

<210> SEQ ID NO 16
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 16
cactttcttc gctgctgg                                            18

```
<210> SEQ ID NO 17
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 17
gcgcttgtag gaactgtt                                                      18

<210> SEQ ID NO 18
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 18
tcaagttgtg taaaggctc                                                     19

<210> SEQ ID NO 19
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 19
caagtggtac cagaatacg                                                     19

<210> SEQ ID NO 20
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 20
ggtgtgtctg atactcctgc                                                    20

<210> SEQ ID NO 21
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 21
gcacgtccag gttctgtgac                                                    20

<210> SEQ ID NO 22
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 22
agataatcaa ggatccacc                                                     19

<210> SEQ ID NO 23
<211> LENGTH: 20
<212> TYPE: DNA
<213> ORGANISM: Artificial sequence
<220> FEATURE:
<223> OTHER INFORMATION: Single strand DNA oligonucleotide
```

<400> SEQUENCE: 23
gtttaagcac cgatgatacc                                                20

<210> SEQ ID NO 24
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 24
gagacgattc agaggagca                                                 19

<210> SEQ ID NO 25
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 25
cgaatatcat caacctcctg                                                20

<210> SEQ ID NO 26
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 26
tctttcaaga ttttcagcag aagca                                          25

<210> SEQ ID NO 27
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 27
aaaagttaga gggagatgat gagca                                          25

<210> SEQ ID NO 28
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 28
accaggatgt cacaaccctc                                                20

<210> SEQ ID NO 29
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 29
tcatagttgc tctctttgga ccat                                           24

<210> SEQ ID NO 30
<211> LENGTH: 9

```
<212> TYPE: PRT
<213> ORGANISM: Artificial Sequence
<220> FEATURE:
<223> OTHER INFORMATION: conserved amino acid sequence motif of the
      LAGLIDADG family of Meganucleases

<400> SEQUENCE: 30

Leu Ala Gly Leu Ile Asp Ala Asp Gly
1               5

<210> SEQ ID NO 31
<211> LENGTH: 6
<212> TYPE: PRT
<213> ORGANISM: Artificial Sequence
<220> FEATURE:
<223> OTHER INFORMATION: conserved amino acid sequence motif of the
      GIY-YIG family of Meganucleases

<400> SEQUENCE: 31

Gly Ile Tyr Tyr Ile Gly
1               5

<210> SEQ ID NO 32
<211> LENGTH: 20
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 32
aaaagtaagc ctcatcatcg                                              20

<210> SEQ ID NO 33
<211> LENGTH: 17
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 33
caaaaaaaaa aaaaaaa                                                 17

<210> SEQ ID NO 34
<211> LENGTH: 13
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 34
caaaaaaaaa aaa                                                     13

<210> SEQ ID NO 35
<211> LENGTH: 41
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 35
cctgttgtat tacgggctcg agtaataccg gagtgtcttg a                      41

<210> SEQ ID NO 36
```

```
<211> LENGTH: 39
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 36
ctgttgtatt acgggctcga gtaataccgg agtgtcttg                              39

<210> SEQ ID NO 37
<211> LENGTH: 20
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 37
atgtaagctg tggtttgcct                                                   20

<210> SEQ ID NO 38
<211> LENGTH: 13
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 38
ctaagtaaat aaa                                                          13

<210> SEQ ID NO 39
<211> LENGTH: 39
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 39
atatatatat atatatat atatatatat atgtgtgtg                                39

<210> SEQ ID NO 40
<211> LENGTH: 17
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 40
atatatatat atatgtg                                                      17

<210> SEQ ID NO 41
<211> LENGTH: 12
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 41
ggaaaaaaaa aa                                                           12

<210> SEQ ID NO 42
<211> LENGTH: 14
```

```
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 42
taaaaaaaaa aaaa                                                         14

<210> SEQ ID NO 43
<211> LENGTH: 20
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 43
tgtttgtttg tttgtttgca                                                   20

<210> SEQ ID NO 44
<211> LENGTH: 14
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 44
atttgtttat ttat                                                         14

<210> SEQ ID NO 45
<211> LENGTH: 14
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 45
caaaaaaaaa aaaa                                                         14

<210> SEQ ID NO 46
<211> LENGTH: 15
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 46
caaaaaaaaa aaaaa                                                        15

<210> SEQ ID NO 47
<211> LENGTH: 12
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 47
caaaaaaaaa aa                                                           12

<210> SEQ ID NO 48
<211> LENGTH: 30
<212> TYPE: DNA
```

```
<213> ORGANISM: Artificial sequence
<220> FEATURE:
<223> OTHER INFORMATION: partial sequencing product of Saccharomyces
      cerevisiae strain S288C

<400> SEQUENCE: 48
caagtgctaa ttatatcttt tccttgacaa                                      30

<210> SEQ ID NO 49
<211> LENGTH: 13
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 49
cacgacgacg acg                                                        13

<210> SEQ ID NO 50
<211> LENGTH: 11
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 50
aatatatata t                                                          11

<210> SEQ ID NO 51
<211> LENGTH: 13
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 51
aatatatata tat                                                        13

<210> SEQ ID NO 52
<211> LENGTH: 50
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 52 ctttttttt tttttttttt tttttatttt tttttttttt tttttttttt                 50

<210> SEQ ID NO 53
<211> LENGTH: 46
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 53 ctttttttt tttttttttt tttttttttt tttttttttt tttttt                     46

<210> SEQ ID NO 54
<211> LENGTH: 60
<212> TYPE: DNA
<213> ORGANISM: Artificial sequence
```

```
<220> FEATURE:
<223> OTHER INFORMATION: partial sequencing product of Saccharomyces
      cerevisiae strain S288C

<400> SEQUENCE: 54
cttttttttt tttttttttt tttttttttt tttttcttt tttttttttt tttttttttt          60

<210> SEQ ID NO 55
<211> LENGTH: 17
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 55
aatatatata tatatat                                                        17

<210> SEQ ID NO 56
<211> LENGTH: 19
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 56
aatatatata tatatatat                                                      19

<210> SEQ ID NO 57
<211> LENGTH: 41
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 57
ttaaagaaat aaggaatacc ataaggttga tcaaatttaa a                             41

<210> SEQ ID NO 58
<211> LENGTH: 39
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 58
taaagaaata aggaatacca taaggttgat caaatttaa                                39

<210> SEQ ID NO 59
<211> LENGTH: 38
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 59
taaagaaata aggaatacca taaggttgat caaattta                                 38

<210> SEQ ID NO 60
<211> LENGTH: 10
<212> TYPE: DNA
<213> ORGANISM: Artificial sequence
<220> FEATURE:
```

```
<223> OTHER INFORMATION: partial sequencing product of Saccharomyces
      cerevisiae strain S288C

<400> SEQUENCE: 60
ctgctgttgt                                                                10

<210> SEQ ID NO 61
<211> LENGTH: 35
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 61
cgaagtgcct gagggctggt tgcaaagggc cgtcg                                    35

<210> SEQ ID NO 62
<211> LENGTH: 16
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 62
cttttttttt tttttt                                                        16

<210> SEQ ID NO 63
<211> LENGTH: 8
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 63 ctttttttt                                                                 8

<210> SEQ ID NO 64
<211> LENGTH: 9
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 64 ctttttttt                                                                 9

<210> SEQ ID NO 65
<211> LENGTH: 10
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 65
aatgaaatag                                                                10

<210> SEQ ID NO 66
<211> LENGTH: 38
<212> TYPE: DNA
<213> ORGANISM: Artificial sequence
<220> FEATURE:
<223> OTHER INFORMATION: partial sequencing product of Saccharomyces
``` cerevisiae strain S288C

<400> SEQUENCE: 66 gatatttttta ttaataatta ttatttattt tttttttat                  38

<210> SEQ ID NO 67
<211> LENGTH: 39
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 67
atataagccc tgtcattgat tgcaaatgca caaattccg                   39

<210> SEQ ID NO 68
<211> LENGTH: 23
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 68
cttttttttt tttttttttt ttt                                    23

<210> SEQ ID NO 69
<211> LENGTH: 9
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 69 ctttttttt                                                     9

<210> SEQ ID NO 70
<211> LENGTH: 23
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 70
cttttttttt tttttttttt ttt                                    23

<210> SEQ ID NO 71
<211> LENGTH: 60
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 71
cttttttttt tttttttttt tttttttttt ttttttttctt tttttttttt tttttttttt   60

<210> SEQ ID NO 72
<211> LENGTH: 20
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 72
aaagaaaaaa agaaaaaaag                                                20

<210> SEQ ID NO 73
<211> LENGTH: 19
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 73
aagaaaaaaa gaaaaaaag                                                 19

<210> SEQ ID NO 74
<211> LENGTH: 17
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 74
aaaaaaaaga aaaaaag                                                   17

<210> SEQ ID NO 75
<211> LENGTH: 9
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 75 ctttttttt                                                             9

<210> SEQ ID NO 76
<211> LENGTH: 10
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 76
cttttttttt                                                           10

<210> SEQ ID NO 77
<211> LENGTH: 9
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 77 cttttttt                                                              9

<210> SEQ ID NO 78
<211> LENGTH: 14
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 78
gttcaaagct tttt                                                         14

<210> SEQ ID NO 79
<211> LENGTH: 16
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 79
cgatgatgat gatgat                                                       16

<210> SEQ ID NO 80
<211> LENGTH: 25
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 80
tcaacaacaa caacaacaac agcaa                                             25

<210> SEQ ID NO 81
<211> LENGTH: 10
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 81
acagcaacag                                                              10

<210> SEQ ID NO 82
<211> LENGTH: 33
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 82
catatatact tatatatata tatatatata tat                                    33

<210> SEQ ID NO 83
<211> LENGTH: 35
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 83
catatatact tatatatata tatatatata tatat                                  35

<210> SEQ ID NO 84
<211> LENGTH: 10
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 84
tggacttata                                                      10

<210> SEQ ID NO 85
<211> LENGTH: 10
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 85
gtgagctatt                                                      10

<210> SEQ ID NO 86
<211> LENGTH: 10
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 86
ctgttgcgct                                                      10

<210> SEQ ID NO 87
<211> LENGTH: 15
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 87
ttatatatat atata                                                15

<210> SEQ ID NO 88
<211> LENGTH: 17
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 88
ttatatatat atatata                                              17

<210> SEQ ID NO 89
<211> LENGTH: 16
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 89
actgaagcca atctat                                               16

<210> SEQ ID NO 90
<211> LENGTH: 25
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 90

```
agcagcagcc ccagctcccg tcgcg                                              25
```

<210> SEQ ID NO 91
<211> LENGTH: 13
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 91

```
ttatatatat ata                                                           13
```

<210> SEQ ID NO 92
<211> LENGTH: 15
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 92

```
ttatatatat atata                                                         15
```

<210> SEQ ID NO 93
<211> LENGTH: 13
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 93

```
gtatatatat ata                                                           13
```

<210> SEQ ID NO 94
<211> LENGTH: 11
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 94

```
gtatatatat a                                                             11
```

<210> SEQ ID NO 95
<211> LENGTH: 25
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 95

```
atgggatacg tcagtatgac aatac                                              25
```

<210> SEQ ID NO 96
<211> LENGTH: 18
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 96

```
ataaaacaca tatgaaac                                                      18
```

<210> SEQ ID NO 97
<211> LENGTH: 9
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 97 caaattata                                                                9

<210> SEQ ID NO 98
<211> LENGTH: 23
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 98
aattgtaaaa gaacgctatt att                                               23

<210> SEQ ID NO 99
<211> LENGTH: 10
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 99
caaaaaaaaa                                                              10

<210> SEQ ID NO 100
<211> LENGTH: 10
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 100
gaaaaaaaaa                                                              10

<210> SEQ ID NO 101
<211> LENGTH: 23
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 101
gaaaaaaaaa aaaaaaaaaa aaa                                               23

<210> SEQ ID NO 102
<211> LENGTH: 25
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 102
gaaaaaaaaa aaaaaaaaaa aaaaa                                             25

<210> SEQ ID NO 103
<211> LENGTH: 41
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 103
cctgttgtat tacgggctcg agtaataccg gagtgtcttg a                          41

<210> SEQ ID NO 104
<211> LENGTH: 39
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 104
ctgttgtatt acgggctcga gtaataccgg agtgtcttg                             39

<210> SEQ ID NO 105
<211> LENGTH: 20
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 105
atgtaagctg tggtttgcct                                                  20

<210> SEQ ID NO 106
<211> LENGTH: 13
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 106
ctaagtaaat aaa                                                         13

<210> SEQ ID NO 107
<211> LENGTH: 39
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 107
atatatatat atatatatat atatatatat atgtgtgtg                             39

<210> SEQ ID NO 108
<211> LENGTH: 17
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 108
atatatatat atatgtg                                                     17

```
<210> SEQ ID NO 109
<211> LENGTH: 12
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 109
acgaaagaga ac                                                          12

<210> SEQ ID NO 110
<211> LENGTH: 15
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 110
caaaaataaa aataa                                                       15

<210> SEQ ID NO 111
<211> LENGTH: 11
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 111
attaaagtgt c                                                           11

<210> SEQ ID NO 112
<211> LENGTH: 22
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 112
agcttcggct tcggcgtcag ct                                               22

<210> SEQ ID NO 113
<211> LENGTH: 9
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 113 aatatatat                                                               9

<210> SEQ ID NO 114
<211> LENGTH: 16
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 114
ttgttacctc gtcacc                                                      16

<210> SEQ ID NO 115
```

```
<211> LENGTH: 29
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 115
atatatatat atatatatat atatatatg                                    29

<210> SEQ ID NO 116
<211> LENGTH: 27
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 116
atatatatat atatatatat atatatg                                      27

<210> SEQ ID NO 117
<211> LENGTH: 10
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 117
atagtacttc                                                         10

<210> SEQ ID NO 118
<211> LENGTH: 29
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 118
taaaagaagt ttcctctttc ctaaactta                                    29

<210> SEQ ID NO 119
<211> LENGTH: 11
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 119
catatatata t                                                       11

<210> SEQ ID NO 120
<211> LENGTH: 13
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 120
catatatata tat                                                     13

<210> SEQ ID NO 121
<211> LENGTH: 22
```

```
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 121
gatacggaaa atttggaaag aa                                           22

<210> SEQ ID NO 122
<211> LENGTH: 23
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 122
gaaaaaaaaa aaaaaaaaaa aaa                                          23

<210> SEQ ID NO 123
<211> LENGTH: 10
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 123
gtccaatgct                                                         10

<210> SEQ ID NO 124
<211> LENGTH: 9
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 124 caaaaaaaa                                                           9

<210> SEQ ID NO 125
<211> LENGTH: 11
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 125
caaaaaaaaa a                                                       11

<210> SEQ ID NO 126
<211> LENGTH: 16
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 126
tatatatata tatata                                                  16

<210> SEQ ID NO 127
<211> LENGTH: 79
<212> TYPE: DNA
```

<213> ORGANISM: Artificial sequence
<220> FEATURE:
<223> OTHER INFORMATION: partial sequencing product of Saccharomyces
      cerevisiae strain S288C

<400> SEQUENCE: 127
ttgttacact gaacatgtta tatttacctg acataccact atattgtact gatgatactt    60
aagacgtgcc aattgcgcg                                                 79

<210> SEQ ID NO 128
<211> LENGTH: 43
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 128
atgttaatca gatatatggt agaaagctct aacttttac cct                       43

<210> SEQ ID NO 129
<211> LENGTH: 50
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 129
aattacagtt agtggctgtt tgctgacatt tcattgcttc ccttacaacc               50

<210> SEQ ID NO 130
<211> LENGTH: 12
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 130
ttcttttatg aa                                                        12

<210> SEQ ID NO 131
<211> LENGTH: 25
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 131
taaaaaaaaa aaaaaaaaa aaaaa                                           25

<210> SEQ ID NO 132
<211> LENGTH: 24
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 132
taaaaaaaaa aaaaaaaaa aaaa                                            24

<210> SEQ ID NO 133
<211> LENGTH: 11

```
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 133
ctgtatatat a                                                              11

<210> SEQ ID NO 134
<211> LENGTH: 31
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 134
ggcccaagct caagcacaag ctcaagcaca a                                        31

<210> SEQ ID NO 135
<211> LENGTH: 19
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 135
ggcccaggct caagcgcaa                                                      19

<210> SEQ ID NO 136
<211> LENGTH: 25
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 136
acagcaacag gcgccattat ctttt                                               25

<210> SEQ ID NO 137
<211> LENGTH: 25
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 137
gttgtcgttg tcgttgtcat tgtca                                               25

<210> SEQ ID NO 138
<211> LENGTH: 17
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 138
cagtaaatat tgaagaa                                                        17

<210> SEQ ID NO 139
<211> LENGTH: 14
<212> TYPE: DNA
```

-continued

```
<213> ORGANISM: Artificial sequence
<220> FEATURE:
<223> OTHER INFORMATION: partial sequencing product of Saccharomyces
      cerevisiae strain S288C

<400> SEQUENCE: 139
atggtattaa tagt                                                       14

<210> SEQ ID NO 140
<211> LENGTH: 13
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 140
caaaaaaaaa aaa                                                        13

<210> SEQ ID NO 141
<211> LENGTH: 38
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 141
attttatata aaataagt aacattccgt gaattaat                               38

<210> SEQ ID NO 142
<211> LENGTH: 25
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 142
gtgagatata tgtgggtaat tagat                                           25

<210> SEQ ID NO 143
<211> LENGTH: 32
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 143
agatatatgt gggtaattag ataattgttg gg                                   32

<210> SEQ ID NO 144
<211> LENGTH: 11
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 144
ctatatatat a                                                          11

<210> SEQ ID NO 145
<211> LENGTH: 21
<212> TYPE: DNA
<213> ORGANISM: Artificial sequence
```

```
<220> FEATURE:
<223> OTHER INFORMATION: partial sequencing product of Saccharomyces
      cerevisiae strain S288C

<400> SEQUENCE: 145
aatggaaaca attttacgga c                                              21

<210> SEQ ID NO 146
<211> LENGTH: 41
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 146
ttaaagaaat aaggaatacc ataaggttga tcaaatttaa a                        41

<210> SEQ ID NO 147
<211> LENGTH: 39
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 147
taaagaaata aggaataccz taaggttgat caaatttaa                           39
```

```
taaagaaata aggaatacca taaggttgat caaatttaa                           39

<210> SEQ ID NO 148
<211> LENGTH: 38
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 148
taaagaaata aggaatacca taaggttgat caaattta                            38

<210> SEQ ID NO 149
<211> LENGTH: 13
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 149
atatgatttg aag                                                       13

<210> SEQ ID NO 150
<211> LENGTH: 12
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 150
attttttttt tt                                                        12

<210> SEQ ID NO 151
<211> LENGTH: 10
<212> TYPE: DNA
<213> ORGANISM: Artificial sequence
<220> FEATURE:
```

<223> OTHER INFORMATION: partial sequencing product of Saccharomyces
      cerevisiae strain S288C

<400> SEQUENCE: 151
attttttttt                                                                10

<210> SEQ ID NO 152
<211> LENGTH: 9
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 152 ctatatata                                                                 9

<210> SEQ ID NO 153
<211> LENGTH: 11
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 153
ctatatatat a                                                             11

<210> SEQ ID NO 154
<211> LENGTH: 11
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 154
gtaatatgtc c                                                             11

<210> SEQ ID NO 155
<211> LENGTH: 22
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 155
ataacaatgt aggagaggcc tt                                                 22

<210> SEQ ID NO 156
<211> LENGTH: 10
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 156
tgaaaaaaaa                                                               10

<210> SEQ ID NO 157
<211> LENGTH: 73
<212> TYPE: DNA
<213> ORGANISM: Artificial sequence
<220> FEATURE:
<223> OTHER INFORMATION: partial sequencing product of Saccharomyces cerevisiae strain S288C

<400> SEQUENCE: 157
ccaagctacc accactactt tagccccaaa gagcaccgct gctgccgttt ctcaaatcgg    60
tgatggtcaa gtt    73

<210> SEQ ID NO 158
<211> LENGTH: 58
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 158
taagactacc gctgctgctg tctctcaaat tggtgatggt caagttcaag ctaccacc    58

<210> SEQ ID NO 159
<211> LENGTH: 10
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 159
aatggttacg    10

<210> SEQ ID NO 160
<211> LENGTH: 25
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 160
atcgtcatca tcatcgtcaa cattt    25

<210> SEQ ID NO 161
<211> LENGTH: 17
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 161
taatcgttat ctattac    17

<210> SEQ ID NO 162
<211> LENGTH: 38
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 162
gatattttta ttaataatta ttatttattt tttttat    38

<210> SEQ ID NO 163
<211> LENGTH: 39
<212> TYPE: DNA
<213> ORGANISM: Artificial sequence
<220> FEATURE:

<223> OTHER INFORMATION: partial sequencing product of Saccharomyces
      cerevisiae strain S288C

<400> SEQUENCE: 163
atataagccc tgtcattgat tgcaaatgca caaattccg                              39

<210> SEQ ID NO 164
<211> LENGTH: 23
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 164
cttttttttt tttttttttt ttt                                              23

<210> SEQ ID NO 165
<211> LENGTH: 9
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 165 ctttttttt                                                               9

<210> SEQ ID NO 166
<211> LENGTH: 23
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 166
cttttttttt tttttttttt ttt                                              23

<210> SEQ ID NO 167
<211> LENGTH: 60
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 167
cttttttttt tttttttttt tttttttttt ttttttcttt tttttttttt tttttttttt      60

<210> SEQ ID NO 168
<211> LENGTH: 10
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 168
tgcagcagca                                                             10

<210> SEQ ID NO 169
<211> LENGTH: 16
<212> TYPE: DNA
<213> ORGANISM: Artificial sequence
<220> FEATURE:
<223> OTHER INFORMATION: partial sequencing product of Saccharomyces cerevisiae strain S288C

<400> SEQUENCE: 169
tgcagcagca gcagca                                                            16

<210> SEQ ID NO 170
<211> LENGTH: 31
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 170
gtcgtcgtcg tcgtcgtcgt cgtcgtcgtc a                                           31

<210> SEQ ID NO 171
<211> LENGTH: 13
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 171
caaaaaaaaa aaa                                                               13

<210> SEQ ID NO 172
<211> LENGTH: 21
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 172
cttttttttt tttttttttt t                                                      21

<210> SEQ ID NO 173
<211> LENGTH: 33
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 173
aatgggtgaa tgttgagata attgttggga ttc                                         33

<210> SEQ ID NO 174
<211> LENGTH: 11
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 174
attttttttt t                                                                 11

<210> SEQ ID NO 175
<211> LENGTH: 13
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 175
ctgtggaaac tta                                                              13

<210> SEQ ID NO 176
<211> LENGTH: 10
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 176
ctgttgttgt                                                                  10

<210> SEQ ID NO 177
<211> LENGTH: 9
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 177 atttttttt                                                                    9

<210> SEQ ID NO 178
<211> LENGTH: 12
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 178 atttttttt tt                                                                12

<210> SEQ ID NO 179
<211> LENGTH: 9
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 179 ctttttttt                                                                    9

<210> SEQ ID NO 180
<211> LENGTH: 11
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 180
catatatata t                                                                11

<210> SEQ ID NO 181
<211> LENGTH: 13
<212> TYPE: DNA
<213> ORGANISM: Artificial sequence
<220> FEATURE:
<223> OTHER INFORMATION: partial sequencing product of Saccharomyces
      cerevisiae strain S288C

```
<400> SEQUENCE: 181
catatatata tat                                                            13

<210> SEQ ID NO 182
<211> LENGTH: 12
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 182
tttttttttt tg                                                             12

<210> SEQ ID NO 183
<211> LENGTH: 9
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 183 ctatatata                                                                  9

<210> SEQ ID NO 184
<211> LENGTH: 22
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 184 ggcataccte ccataccacc at                                                  22

<210> SEQ ID NO 185
<211> LENGTH: 12
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 185
caaaaaaaaa aa                                                             12

<210> SEQ ID NO 186
<211> LENGTH: 11
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 186
caaaaaaaaa a                                                              11

<210> SEQ ID NO 187
<211> LENGTH: 18
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 187
```

```
cttttttttt tttttttt                                          18
```

<210> SEQ ID NO 188
<211> LENGTH: 9
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 188

```
ctttttttt                                                     9
```

<210> SEQ ID NO 189
<211> LENGTH: 13
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 189

```
caataataat aat                                               13
```

<210> SEQ ID NO 190
<211> LENGTH: 49
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 190

```
caacaacaac aacaacaaca acaacaacaa caacaacaat aataataat        49
```

<210> SEQ ID NO 191
<211> LENGTH: 52
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 191

```
caacaacaac aacaacaaca acaacaacaa caacaacaac aataataata at    52
```

<210> SEQ ID NO 192
<211> LENGTH: 18
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 192

```
atgaaacgac tttataac                                          18
```

<210> SEQ ID NO 193
<211> LENGTH: 18
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 193

```
tttctttgaa aacaccag                                                   18

<210> SEQ ID NO 194
<211> LENGTH: 10
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 194
aggaaacgtc                                                            10

<210> SEQ ID NO 195
<211> LENGTH: 18
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 195
atcgtcccca gttttttcc                                                  18

<210> SEQ ID NO 196
<211> LENGTH: 11
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 196
ctttattcgt t                                                          11

<210> SEQ ID NO 197
<211> LENGTH: 12
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 197
gtcctaaata aa                                                         12

<210> SEQ ID NO 198
<211> LENGTH: 17
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 198
tttctataaa tatttga                                                    17

<210> SEQ ID NO 199
<211> LENGTH: 39
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 199
gtgacacaag ataaaacgac tccatggcca agttggtta                            39
```

```
<210> SEQ ID NO 200
<211> LENGTH: 17
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 200
ttcatcaaat acatctc                                                      17

<210> SEQ ID NO 201
<211> LENGTH: 22
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 201
gatatccata ttttggttgc aa                                                22

<210> SEQ ID NO 202
<211> LENGTH: 10
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 202
agaaagtaag                                                              10

<210> SEQ ID NO 203
<211> LENGTH: 37
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 203
agatgatgat gaagaagaag aagaagatga tgatgat                                37

<210> SEQ ID NO 204
<211> LENGTH: 10
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 204
caaaaaaaaa                                                              10

<210> SEQ ID NO 205
<211> LENGTH: 10
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 205
gaaaaaaaaa                                                              10
```

```
<210> SEQ ID NO 206
<211> LENGTH: 25
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 206
gaaaaaaaaa aaaaaaaaaa aaaaa                                          25

<210> SEQ ID NO 207
<211> LENGTH: 20
<212> TYPE: DNA
<213> ORGANISM: Artificial sequence
<220> FEATURE:
<223> OTHER INFORMATION: partial sequencing product of Saccharomyces
      cerevisiae strain S288C

<400> SEQUENCE: 207
agatatatgt gggtaattag                                                20
```

COMPOSITIONS AND METHODS FOR IMPROVING ALCOHOL TOLERANCE IN YEAST

RELATED APPLICATIONS

This application is a National Phase of PCT Patent Application No. PCT/IL2018/050935 having International filing date of Aug. 23, 2018, which claims the benefit of priority under 35 USC § 119(e) of U.S. Provisional Patent Application No. 62/549,062 filed on Aug. 23, 2017. The contents of the above applications are all incorporated by reference as if fully set forth herein in their entirety.

SEQUENCE LISTING STATEMENT

The ASCII file, entitled 81457SequenceListing.txt, created on Feb. 19, 2020 comprising 51,037 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to methods and compositions for improving alcohol tolerance in yeast and, more particularly, but not exclusively, to survival and propagation in ethanol.

Ethanol an important biofuel used worldwide and can be produced by fermentation in yeast such as *Saccharomyces cerevisiae*. Since ethanol can be toxic to the yeast cells, a cell's ethanol tolerance is a key factor in ethanol production (Amorim et al., 2011). Uncovering a genetic basis for variation for ethanol tolerance in the yeast *S. cerevisiae* is necessary in order to improve the efficiency of biofuel producing strains, through selection, introgression or engineering. However, ethanol tolerance of yeast is a polygenic and complex quantitative trait (Hu el al., 2007). In modern genetics, analysis of multiple loci, each with a small effect, remains a central challenge to identifying genes involved in a particular process (Swinnen et al., 2012b).

The present invention provides methods and compositions for improving ethanol tolerance in yeast and other related advantages.

SUMMARY OF THE INVENTION

According to an aspect of the present invention, there is provided a yeast strain being capable of surviving 15% (V/V) ethanol stress for at least 5 hours and capable of propagating under 9.5% (V/V) ethanol stress for at least 22 hours.

According to an aspect of the present invention, there is provided a yeast strain being capable of surviving 19% (V/V) ethanol stress for at least 5 hours and capable of propagating under 9.5% (V/V) ethanol stress for at least 22 hours.

According to an aspect of the present invention, there is provided a yeast strain being capable of surviving in 19% (V/V) ethanol stress for at least 5 hours.

According to an aspect of the present invention, there is provided a yeast strain, being a progeny of the yeast strain described herein.

According to an aspect of the present invention, there is provided a culture comprising the yeast strain of any one of claims 1-22 and a culture medium, wherein the percentage of ethanol in the medium is from about 5% (V/V) to about 50% (V/V).

According to an aspect of the present invention, there is provided a food, beverage or animal feed comprising the yeast strain of any one of claims 1-22.

According to an aspect of the present invention, there is provided a method of increasing the ability of a yeast strain to propagate under alcohol stress comprising mutating at least one site on a genome of a yeast having a location as set forth in Table 11, thereby increasing the ability of a yeast strain to propagate under alcohol stress.

According to an aspect of the present invention, there is provided a method of increasing the ability of a yeast strain to survive under alcohol stress comprising mutating at least one site on a genome of a yeast having a location as set forth in Table 12, thereby increasing the ability of a yeast strain to survive under alcohol stress.

According to an aspect of the present invention, there is provided a method of selecting a yeast strain which is capable of propagating under alcohol stress and/or surviving ethanol stress comprising analyzing for the presence of at least one mutation set forth in Tables 11 or 12, wherein the presence of the mutation is indicative of a yeast strain which is capable of propagating and or surviving under alcohol stress.

According to embodiments of the present invention, the yeast strain has a mutation in at least one gene associated with C-compounds and carbohydrate metabolism.

According to embodiments of the present invention, the at least one gene is selected from the group consisting of HAP2, RTG2, HXK2, PFK1, SNF6, PFK26, RGR1, MKS1, GCR2, GAL11, SNF2, GCR1, TAF14, BEM4 and GAL4.

According to embodiments of the present invention, the yeast strain has a mutation in at least one gene selected from the group consisting of ADH2, MOG1, YJR154W, RTG2, MGS1, ZRT1, RNR2 and MMP1.

According to embodiments of the present invention, the yeast strain has a mutation in ADH2 or ADR1 or the binding site of the product of ADR1.

According to embodiments of the present invention, the mutation causes a loss of function.

According to embodiments of the present invention, the yeast strain has a genomic mutation at a position set forth in Table 11.

According to embodiments of the present invention, the position is in an open reading frame of a gene.

According to embodiments of the present invention, the position is in a non-open reading frame of a gene.

According to embodiments of the present invention, the position of the mutation is set forth in Table 11.

According to embodiments of the present invention, the yeast strain has a mutation in at least one gene as set forth in Table 11.

According to embodiments of the present invention, the yeast strain has a mutation in at least one gene set forth in Table 12.

According to embodiments of the present invention, the yeast strain has a mutation at a position set forth in Table 12.

According to embodiments of the present invention, the yeast strain has a mutation in at least one gene set forth in Table 12.

According to embodiments of the present invention, the position of the mutation is set forth in Table 12.

According to embodiments of the present invention, the yeast strain is capable of propagating at a temperature above 30° C.

According to embodiments of the present invention, the yeast strain is capable of propagating in a medium comprising an amount of sugar above 5%.

According to embodiments of the present invention, the yeast strain is non-genetically modified.

According to embodiments of the present invention, the yeast strain is genetically modified to express a recombinant protein or a regulatory RNA.

According to embodiments of the present invention, the medium comprises a liquid medium.

According to embodiments of the present invention, the liquid medium comprises YPD.

According to embodiments of the present invention, the medium further comprises a carbon source.

According to embodiments of the present invention, the carbon source is glucose.

According to embodiments of the present invention, the carbon source is a waste product.

According to embodiments of the present invention, the culture is sterile.

According to embodiments of the present invention, the site is located in at least one gene of a yeast as set forth in Table 11.

According to embodiments of the present invention, the gene of a yeast is associated with C-compounds and carbohydrate metabolism.

According to embodiments of the present invention, the at least one gene is selected from the group consisting of HAP2, RTG2, HXK2, PFK1, SNF6, PFK26, RGR1, MKS1, GCR2, GAL11, SNF2, GCR1, TAF14, BEM4 and GAL4.

According to embodiments of the present invention, the alcohol comprises ethanol.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

The patent or application file contains at least one drawing executed in color. Copies of this patent or patent application publication with color drawing(s) will be provided by the Office upon request and payment of the necessary fee.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-D is a pictorial image illustrating AIL and tails selection. (A) F1 offspring were intercrossed for 5 generations to create F6. (B) First stage: Mass-selection for 35% survival under 15% (V/V) ethanol stress to create initial phenotypic upper tail group. (C) Random sampling of 300 colonies from the initial survival upper tail group. (D) Individual phenotypic evaluation of these 300 individuals separately for growth and for survival under ethanol stress, to create two final selected tails containing the highest 90 individuals each for growth and survival in the presence of ethanol. The entire F6 population (A) was used as a control for both traits. For statistical purposes, each tail and control group was randomly divided into 3 subgroups. Dark color, resistant strain.

FIGS. 4A-C are graphs illustrating the smoothed mean SNP Allele frequency and D-values on chromosome 11. Average frequency of YE-531 allele of the 3 replicates of a group, after LOESS smoothing. Blue: The general population; Red: upper tail; (A) growth; (B) survival. Some regions show large differences between the allele frequencies of tails and general (arrows: Red arrow, significant region only for survival; orange arrows, significant region for both traits). (C) The allele frequency difference between the tail groups and the F6 (D-values). Orange: growth; Purple: survival.

FIGS. 5A-C: Declaring QTLs on Chromosome 11. Log P values of SNPs after LOESS smoothing of allele frequency and SD were plotted against the marker position. Significant regions are those above FDR 0.2 and after log-drop procedure as in Lipkin et. al., 2016[23]. Blue diamond, smoothed SNP-log P-value; red line, 0.2 FDR, Green diamond, QTL after log-drop procedure. (A) Growth. The position of 5 declared QTLs is marked by gold circles on the X axis. The gap around location 210 is a result of lack of SNPs at that region, due to data filtered out for technical reasons). (B) Survival. The position of 8 declared QTLs marked by gold circles. (C) Log drop boundaries on chromosome 11. QTL unique to growth or survival can be seen (e.g., Survival 401-419 kb; red arrow on B).

FIGS. 6A-C: Example for mapping resolution to a single gene level. Shown are QTLs of survival trait on Chromosome 11. Blue dots, smoothed SNP-log P-value; red line, 0.2 FDR; Green dots, QTL log-drop boundaries; red circle, centromere. (A) Smoothed P-values. (B) Zoom-in on a small QTL containing part of DYN1 gene. (C) Non-synonymous mutations in DYN1. Blue line, DYN1 ORF; Orange circles, serial number by location of non-synonymous mutations. Mutations position and alternative amino acids are summarized in the table.

FIGS. 10A-C are graphs of individual frequency estimates of a tested SNP by real time PCR coupled to High Resolution Melting (HRM) genotyping. The charts are focused on the $T_m$ area for a SNP located in the gene UPT20 on chromosome 2 position 228,251 (examined for 30 individuals which composed one of the survival upper tail group and 30 random segregants of the entire F6 population) (A) HRM results for S288c (blue), YE-531 (green) and a mix of both (brown). (B) HRM results for S288c (blue), YE-531 (green) mix of both of them (brown) and segregant YE-159 having the allele of S288c (pink). (C) HRM results for S288c (blue), YE-531 (green) mix of both (brown) and one of the segregant YE-270 having the allele of YE-531 (yellow).

FIGS. 13A-B: Ethanol tolerance of parental lines. (A) Survival of parental lines and the F1 in the presence of ethanol. Cells from each strain were incubated in YPD medium in 19% (V/V) ethanol at 30° C. for 5 hours, in anaerobic conditions. Each drop was seeded in spot assay at 1 to 100,000 fold dilution. The process was done in 4 biological repeats. (B) Growth ability of parental lines and the F1 in the presence of 9.5% (V/V) ethanol (Blue) and 10.8% (V/V) ethanol (red). Cells from each strain, in equal concentrations, were grown in YPD medium with ethanol content at 30° C. for 22 hours, in anaerobic condition. Final 600 nm absorbance was measured. The mean values and SD are presented

FIG. 17: Improved ethanol production by ADH2 deletion strains in accordance to RHA. Shown is average ethanol production of the F1, ADH2 reciprocal hemizygous deletions, and a double deletion strain in the F1 background, after 17 fermentation hours. Results are the average of 2 biological replicates (for each one 2 technical repeats). Fermentations were conducted using corn mash at 32.5° C. and 160 rpm agitation, under anaerobic conditions, with initial cell concentration of $10^7$ cells/ml.

DESCRIPTION OF SPECIFIC EMBODIMENTS OF THE INVENTION

Figure 2A:
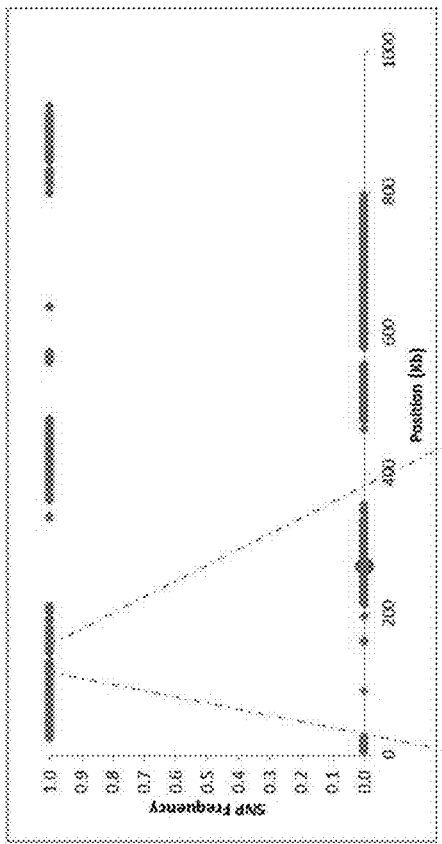
FIGS. 2A-B are graphs illustrating recombination block structure of Line-8, an F6 individual haploid segregant. (A) Founder SNPs origin across chromosome 13. Sequences were aligned to the reference S288c genome sequence. Thus, SNP frequencies 0 or 1 indicates an S288c or YE-531 allele, respectively. Red circle, centromere; (B) Zoom-in on a small haplotype block of size 4,554 bp.

The present invention, in some embodiments thereof, relates to methods and compositions for improving alcohol tolerance in yeast and, more particularly, but not exclusively, to survival and propagation in ethanol.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Ethanol, the end product of fermentation in *Saccharomyces cerevisiae*, is the main biofuel used worldwide. Since ethanol is toxic to the yeast cell, ethanol production is inhibited by its accumulation. Therefore, understanding the genetic basis of ethanol tolerance is important for the development of improved yeast strains with higher ethanol tolerance and yields. However, up until presently, genomic elements affecting ethanol tolerance have only been mapped at low resolution, hindering their identification. The present inventors have now used an Advanced Intercross Line design, to perform high resolution mapping of (quantitative trait locii) QTLs affecting ethanol tolerance in yeast; two-stage Selective DNA Pooling and whole-genome sequencing, with LOESS smoothing and log-drop boundaries to produce a High Resolution Mapping Tool-kit (HRMT) for high resolution mapping of complex traits. The tool-kit was applied to an F6 intercross between two *S. cerevisiae* strains, which are phylogenetically distinct, but phenotypically similar, to identify QTLs affecting growth and survival under ethanol stress.

Fifty-one and 96 QTLs affecting growth and survival, respectively, were identified by applying a unique statistical pipeline based on LOESS smoothing and Log drop. This is a much larger number than in all previous ethanol tolerance mapping studies combined. Importantly, the QTLs were much narrower than previously reported by non-AIL studies, with some including only a single gene. The median size of a QTL was 9.4 Kb (growth) and 10.53 Kb (survival). The QTLs explained 34% of the phenotypic variation for growth and 72% for survival. High statistical power provided by HRMT tool-kit allowed detection of many loci with small, but mappable effects uncovering a novel "quasi-infinitesimal" genetic architecture, which may hold the key to the "missing heritability" conundrum. These results provide a striking confirmation of the very large amounts of cryptic genetic variations exposed in crosses between strains with similar phenotypes. The findings suggest that ethanol tolerance is under natural evolutionary fitness-selection for an optimum phenotype, that would tend to eliminate alleles of large effect. Significant effects of novel chosen mapped genes were shown showed experimentally for MOG1, MGS1 and YJR154W. In addition, a strong effect of candidate causative mutations was predicted on RNR2 and MMP1 protein structures. The study provides a platform for development of ethanol tolerant strains far superior to any currently available.

Thus, according to one aspect of the present invention there is provided a yeast strain being capable of surviving 15% (V/V) ethanol stress for at least 5 hours and capable of propagating under 9.5% (V/V) ethanol stress for at least 22 hours.

According to another aspect of the present invention, there is provided a yeast strain being capable of surviving in 19% (V/V) ethanol stress for at least 5 hours.

The yeast strain of the present invention may belong to the genus *Saccharomyces*, *Zygosaccharomyces*, *Pichia*, *Kluyveromyces*, *Candida*, *Shizosaccharomyces*, *Issachenkia*, or *Hansenula*.

A strain belonging to *Saccharomyces* may belong to the species *S. cerevisiae*, *S. bayanus*, *S. boulardii*, *S. bulderi*, *S. cariocanus*, *S. cariocus*, *S. chevalieri*, *S. dairenensis*, *S. ellipsoideus*, *S. eubayanus*, *S. exiguus*, *S. florentinus*, *S. kluyveri*, *S. martiniae*, *S. monacensis*, *S. norbensis*, *S. paradoxus*, *S. pastorianus*, *S. spencerorum*, *S. turicensis*, *S. unisporus*, *S. uvarum*, or *S. zonatus*.

According to a particular embodiment, the yeast strain is *S. cerevisiae*.

The yeast strains of the present invention are capable of propagating in a medium comprising about 7% (v/v), 7.5%, 8%, 8.5%, 9%, 9.5%, 10%, 10.5% alcohol (e.g. ethanol) at 30° C. for at least 3 hours, 12 hours, 22 hours, 24 hours or longer.

Another way of characterizing the yeast of this aspect of the present invention is by their ability to tolerate (remain alive) in the presence of alcohol (e.g. ethanol). Thus, for example, in one embodiment the yeast strains of the present invention are capable of surviving in a medium comprising about 15% (V/V) ethanol stress, 16% (V/V) ethanol stress for at least 5 hours, 17% (V/V) ethanol stress for at least 5 hours, 18% (V/V) ethanol stress for at least 5 hours, 19% (V/V) ethanol stress for at least 5 hours or even 20% (V/V) ethanol stress for at least 5 hours at 30° C.

Another way of characterizing the yeast of this aspect of the present invention is by their ability to tolerate, grow and ferment in high osmotic stress. Thus, for example, in one embodiment the yeast strains of the present invention are capable of surviving (and optionally growing) in a medium comprising more than about 6% (v/v) glucose, more than 7% (v/v) glucose, more than 8% (v/v) glucose, more than 9% (v/v) glucose, more than 10% (v/v) glucose at 30° C. for at least 24 hours and more preferably at least 48 hours.

Another way of characterizing the yeast of this aspect of the present invention is by their ability to tolerate, grow and ferment in high temperatures. Thus, for example, in one embodiment the yeast strains of the present invention are capable of surviving (and optionally growing) at 34° C., 35° C., 36° C., 37° C., 38° C., 39° C. or even 40° C. for at least 24 hours and more preferably at least 48 hours.

The yeast strain which is capable of surviving 15% (V/V) ethanol stress for at least 5 hours and capable of propagating under 9.5% (V/V) ethanol stress for at least 22 hours may have a genomic mutation at a position shown in Table 11.

The term "mutation" as used herein refers to a change in a nucleic acid sequence compared to the reference genome strain S288c, version R64-1-1.

The mutation may be an insertion, a deletion or a substitution mutation (including silent mutations, nonsense mutations and missense mutations).

In one embodiment, the mutation is a point mutation.

In still another embodiment, the mutation comprises a loss of function alteration.

As used herein, the phrase "loss-of-function alterations" refers to any mutation in the DNA sequence of a gene which results in downregulation of the expression level and/or activity of the expressed product, i.e., the mRNA transcript and/or the translated protein. Non-limiting examples of such loss-of-function alterations include a missense mutation, i.e., a mutation which changes an amino acid residue in the protein with another amino acid residue and thereby abolishes the enzymatic activity of the protein; a nonsense mutation, i.e., a mutation which introduces a stop codon in a protein, e.g., an early stop codon which results in a shorter protein devoid of the enzymatic activity; a frame-shift mutation, i.e., a mutation, usually, deletion or insertion of nucleic acid(s) which changes the reading frame of the protein, and may result in an early termination by introducing a stop codon into a reading frame (e.g., a truncated protein, devoid of the enzymatic activity), or in a longer amino acid sequence (e.g., a readthrough protein) which affects the secondary or tertiary structure of the protein and results in a non-functional protein, devoid of the enzymatic activity of the non-mutated polypeptide; a readthrough mutation due to a frame-shift mutation or a modified stop codon mutation (i.e., when the stop codon is mutated into an amino acid codon), with an abolished enzymatic activity; a promoter mutation, i.e., a mutation in a promoter sequence, usually 5' to the transcription start site of a gene, which results in down-regulation of a specific gene product; a regulatory mutation, i.e., a mutation in a region upstream or downstream, or within a gene, which affects the expression of the gene product; a deletion mutation, i.e., a mutation which deletes coding nucleic acids in a gene sequence and which may result in a frame-shift mutation or an in-frame mutation (within the coding sequence, deletion of one or more amino acid codons); an insertion mutation, i.e., a mutation which inserts coding or non-coding nucleic acids into a gene sequence, and which may result in a frame-shift mutation or an in-frame insertion of one or more amino acid codons; an inversion, i.e., a mutation which results in an inverted coding or non-coding sequence; a splice mutation i.e., a mutation which results in abnormal splicing or poor splicing; and a duplication mutation, i.e., a mutation which results in a duplicated coding or non-coding sequence, which can be in-frame or can cause a frame-shift.

The yeast strain of any of the aspects of the present invention may have any of number of the above identified mutations, preferably at least 10, 20, 30, 40, 50, 60, 70, 80, 90, 100, 200, 300, 400, 500, 600, 700, 800, 900, 1000 or more of those shown in Tables 11 and 12.

In one embodiment, the mutation is on an open reading frame at a position shown in Table 11.

In another embodiment, the mutation is on a non-open reading frame at a position shown in Table 11.

In still another embodiment, the mutation is on a gene, the name of which is set forth in Table 11.

Particular genes which may be mutated include, but are not limited to ADH2, MOG1, MGS1 and YJR154W. Other exemplary genes that may be mutated include RTG2, ZRT1 and MMP1. Still another gene that may be mutated is ADR1.

Other genes which may be mutated are those associated with regulation of C-compounds and/or carbohydrate metabolism. Examples of such include, but are not limited to HAP2, RTG2, HXK2, PFK1, SNF6, PFK26, RGR1, MKS1, GCR2, GAL11, SNF2, GCR1, TAF14, BEM4 and GAL4.

Other genes which may be mutated are those that show strong candidate mutations on protein structure include, such as RNR2 and MMP1.

The yeast strain which is capable of surviving in 19% (V/V) ethanol stress for at least 5 hours may have a genomic mutation at a position shown in Table 12.

In one embodiment, the mutation is on an open reading frame at a position shown in Table 12.

In another embodiment, the mutation is on a non-open reading frame at a position shown in Table 12.

In still another embodiment, the mutation is on a gene, the name of which is set forth in Table 12.

The present inventors have further determined which QTLs contribute the largest effect on survival (see Table 10B). Thus, for example the present inventors anticipate that mutations in QTL 2 will affect survival to a greater extent than QTL 96, as shown by the increase in allele effect (δ).

Below is a list (in order of influence) of the most influential QTLs which may be mutated in order to increase ethanol survival in yeast:

QTL 2>QTL 30 and 34>QTL 95>QTL 21>QTL 6>QTL41>QTL40, wherein the range of the QTLs is set forth in Table 8 and the position within the range are specified in Table 12.

In one embodiment, the yeast strain of the present invention is generated by breeding, for example by using the Ether-Zymolyase (EZ) Ascospore isolation procedure which is a technique that allows rapid and efficient spore isolation in yeast. Briefly, at least two haploid strains are crossed and grown using standard techniques (e.g. YPD plates at 30° C. overnight). The strains may be comprised in a mixture of 2-100 different strains. The cultures are then sporulated using standard techniques. Ascospores are isolated from sporulated cultures in each generation by treatment with ether and zymolyase (EZ) as described in Bahalul et al. (2010). The ascospores are germinated and then intercrossed. This cycle of random intercrosses, sporulation, spore isolation and germination is repeated multiple times. In some embodiments, the cycle is repeated about 3 times, about 4 times, about 5 times, about 6 times, about 7 times, about 8 times, about 9 times, about 10 times, or more. In a particular embodiment, the cycle of random intercrosses, sporulation, spore isolation and germination is repeated about 6 times. This repetition of the cycle over 6 generations allows numerous genetic combinations with reduced linkage disequilibrium.

Any appropriate haploid laboratory strain may be used including, but not limited to, S288c, BY4743, FY4, DBY12020, DBY12021, FY1679, AB972, A364A, DC5, X2180-la, XJ24-24a, YNN216, YPH499, YPH500, YPH501, Sigma1278b, SKI, CEN.PK, W303, W303-1A, W303-1B, W303-K6001, DY1457, D273-10B, FL100, SEY6210, SEY6211, JK9-3d, RM11-1A, and Y55. In a particular embodiment, the haploid laboratory strain is S288c. Any appropriate haploid natural strain may be used including, but not limited to, UCD51, UCD175, UCD522, UCD762, UCD765, UCD820, UCD2120, M5, M13, BC191, BC192, BC193, YPS606, YPS623, YPS2052, YPS2056, BC186, BC187, BC210, BC216, BC217, BC233, BC235, BC240, BC241, BC248, BC251 and YE-531.

In a particular embodiment, the strains that are crossed are S288c and YE-531.

Pools of yeast cultures exhibiting enhanced growth in alcohol (e.g. ethanol) or enhanced survival in alcohol (e.g. ethanol) may be identified using a selection process. In one embodiment, the yeast strain is first selected by testing for increased survival at various ethanol percentages. In some embodiments, the yeast are tested for increased survival in about 1% (v/v) to about 30% (v/v) ethanol compared to survival in one or both of the parental strains. In some embodiments, the yeast are tested for increased survival in about 5% (v/v) ethanol, about 6% (v/v) ethanol, about 7% (v/v) ethanol, about 8% (v/v) ethanol, about 9% (v/v)

ethanol, about 10% (v/v) ethanol, about 11% (v/v) ethanol, about 12% (v/v) ethanol, about 13% (v/v) ethanol, about 15% (v/v) ethanol, about 16% (v/v) ethanol, about 17% (v/v) ethanol, about 18% (v/v) ethanol, about 19% (v/v) ethanol, or about 20% (v/v) ethanol or more compared to survival in one or both parental strains. In particular embodiments, in the last round of testing, the yeast are tested for survival in about 15% (v/v) or 19% (v/v) ethanol.

In some embodiments, the target survival rate (based on CFU of the unselected and challenged populations) is about 10%, about 20%, about 30%, about 35%, about 40%, about 45%, about 50% or more. In some embodiments, the target survival rate is obtained with ethanol stress for a particular time period. In some embodiments, the target survival rate is obtained with ethanol stress concentrations of about 1% (v/v) to 40% (v/v) for about 0.5 hours to about 10 hours. In particular embodiments, the target survival rate is obtained with about 15% (v/v) ethanol stress for about 5 hours. In particular embodiments, the target survival rate is about 35%.

Survival is determined as the ability of the cells to remain viable under the applied stress. Cell viability refers to whether a cell is living or dead. Cell viability measurements may be used to evaluate the death or life of cells. Cell viability tests can be used to determine the ability of cells to remain alive upon after exposure to ethanol. Survival in ethanol can be measured using any appropriate means in the art. In some embodiments, survival is measured by diluting and plating for CFU (colony forming units) estimation. In particular embodiments, survival is measured by suspending a cell culture in YPD-15% (v/v) ethanol for 5 hours and then spread on a plate for live count (CFU) measurement. In other embodiments, survival is measured by suspending a cell culture in YPD-19% (v/v) ethanol for 5 hours and then spread on a plate for live count (CFU) measurement.

In another embodiment, the yeast are tested for their ability to grow and survive in alcohol (e.g. ethanol). The test may be performed at any of the ethanol concentrations and time periods disclosed above. In a particular embodiment, the final test is performed at 9.5% (v/v) ethanol. In some embodiments, the yeast are tested for their ability to grow and survive in about 1% (v/v) to about 40% (v/v) ethanol. In some embodiments, the yeast are tested for their ability to grow and survive in about 5% (v/v) ethanol, about 6% (v/v) ethanol, about 7% (v/v) ethanol, about 8% (v/v) ethanol, about 9% (v/v) ethanol, about 9.5% (v/v) ethanol about 10% (v/v) ethanol, about 11% (v/v) ethanol, about 12% (v/v) ethanol, about 13% (v/v) ethanol, about 15% (v/v) ethanol, about 16% (v/v) ethanol, about 17% (v/v) ethanol, about 18% (v/v) ethanol, about 19% (v/v) ethanol, or about 20% (v/v) ethanol or more. In some embodiments the test is a comparative test, using at least one of the parental strains as a control.

In some embodiments, the increased growth and survival is obtained after a particular time period. In some embodiments, the increased growth is obtained with ethanol concentrations of about 1% (v/v) to 40% (v/v) for about 0.5 hours to about 24 hours. In some embodiments, the target survival rate is obtained with about 19% (v/v) ethanol for about 5 hours.

Growth is determined as the ability of cells to keep dividing and increase cell density. Growth in ethanol can be measured using any appropriate means in the art. In some embodiments, growth is measured by detection at optical density (OD) 600 nm. In some embodiments, growth is measured by diluting and plating colonies. In some embodiments, growth is detected by measuring colony forming units (CFU). In particular embodiments, growth is measured by suspending a cell culture in YPD-9.5% (v/v) ethanol for 22 hours and then measuring for growth at OD 600 nm. The strains that rank best in this growth test are selected for further analysis.

The present inventors have further determined which QTLs contribute the largest effect growth (see Table 10A). Thus, for example the present inventors anticipate that mutations in QTL 18 will affect growth to a greater extent than QTL 47, as shown by the increase in allele effect (δ).

Below is a list (in order of influence) of the most influential QTLs which may be mutated in order to increase growth of yeast:

QTL 18>QTL 1>QTL 17>QTL 6>QTL 7>QTL4, wherein the range of the QTLs is set forth in Table 7 and the position within the range are specified in Table 11.

In one embodiment, the yeast strains of the present invention are not genetically modified. In another embodiment, the yeast strains do not express a recombinant protein that alters the ethanol susceptibility.

In other embodiments, the yeast strains of the present invention may be genetically modified to express:

1. Polypeptides which are involved with the trans-membrane transportation of sugars;
2. Polypeptides which are involved with cellulose degradation (cellulases);
3. Polypeptides which are involved with Hemicellulose degradation;
4. Polypeptides which are involved with Lignocellulose degradation;
5. Polypeptides which are involved with Pectin degradation;
6. Proteins that are part of the pentose phosphate pathway.

Other contemplated polypeptides which may be expressed in the yeast strains of the present invention include an amylase genes such as glucoamylase (GlaA) and alpha amylase. Other contemplated polypeptides which may be expressed in the yeast strains include, but are not limited to cellulase and other polysaccharides degrading enzymes as well as proteases.

It will be appreciated that as well as expressing a recombinant protein, the present invention also contemplates expressing regulatory RNAs in the yeast strains of the present invention.

In yet another embodiment, the yeast strains are genetically modified so as to express an industrially useful or therapeutic protein.

The protein may be a secreted protein or an intracellular protein.

Exemplary therapeutic proteins that can be produced in the yeast of this aspect of the present invention include but are not limited human hormones (e.g., insulin, growth hormone, insulin-like growth factor 1, follicle-stimulating hormone, and chorionic gonadotropin), hematopoietic proteins (e.g., erythropoietin, C-CSF, GM-CSF, and IL-11), thrombotic and hematostatic proteins (e.g., tissue plasminogen activator and activated protein C), immunological proteins (e.g., interleukin), antibodies and other enzymes (e.g., deoxyribonuclease I). Exemplary vaccines that can be produced by the subject compositions and methods include but are not limited to vaccines against various influenza viruses (e.g., types A, B and C and the various serotypes for each type such as H5N2, H1N1, H3N2 for type A influenza viruses), HIV, hepatitis viruses (e.g., hepatitis A, B, C or D), Lyme disease, and human papillomavirus (HPV). Examples of heterologously produced protein diagnostics include but are not limited to secretin, thyroid stimulating hormone (TSH), HIV antigens, and hepatitis C antigens.

Other proteins or peptides that may be produced in the yeast strains of the present invention include, but are not limited to carbohydrates digest enzymes like amylase, cellulose degrading enzymes, maltase, lactase and Melibiose, cytokines, chemokines, lymphokines, ligands, receptors, hormones, enzymes, antibodies and antibody fragments, and growth factors. Non-limiting examples of receptors include TNF type I receptor, IL-1 receptor type II, IL-1 receptor antagonist, IL-4 receptor and any chemically or genetically modified soluble receptors. Examples of enzymes include acetylcholinesterase, lactase, activated protein C, factor VII, collagenase (e.g., marketed by Advance Biofactures Corporation under the name Santyl); agalsidase-beta (e.g., marketed by Genzyme under the name Fabrazyme); domase-alpha (e.g., marketed by Genentech under the name Pulmozyme); alteplase (e.g., marketed by Genentech under the name Activase); pegylated-asparaginase (e.g., marketed by Enzon under the name Oncaspar); asparaginase (e.g., marketed by Merck under the name Elspar); and imiglucerase (e.g., marketed by Genzyme under the name Ceredase). Examples of specific polypeptides or proteins include, but are not limited to granulocyte macrophage colony stimulating factor (GM-CSF), granulocyte colony stimulating factor (G-CSF), macrophage colony stimulating factor (M-CSF), colony stimulating factor (CSF), interferon beta (IFN-beta), interferon gamma (IFNgamma), interferon gamma inducing factor I (IGIF), transforming growth factor beta (IGF-beta), RANTES (regulated upon activation, normal T-cell expressed and presumably secreted), macrophage inflammatory proteins (e.g., MIP-1-alpha and MIP-1-beta), Leishmnania elongation initiating factor (LEIF), platelet derived growth factor (PDGF), tumor necrosis factor (TNF), growth factors, e.g., epidermal growth factor (EGF), vascular endothelial growth factor (VEGF), fibroblast growth factor, (FGF), nerve growth factor (NGF), brain derived neurotrophic factor (BDNF), neurotrophin-2 (NT-2), neurotrophin-3 (NT-3), neurotrophin-4 (NT-4), neurotrophin-5 (NT-5), glial cell line-derived neurotrophic factor (GDNF), ciliary neurotrophic factor (CNTF), TNF alpha type II receptor, erythropoietin (EPO), insulin and soluble glycoproteins e.g., gp120 and gp160 glycoproteins. The gp120 glycoprotein is a human immunodeficiency virus (WIV) envelope protein, and the gp 160 glycoprotein is a known precursor to the gp 120 glycoprotein. Other examples include secretin, nesiritide (human B-type natriuretic peptide (hBNP)) and GYP-I.

Bioactive peptides may also be produced in the yeast strains of the present invention. Examples include: BOTOX, Myobloc, Neurobloc, Dysport (or other serotypes of botulinum neurotoxins), alglucosidase alfa, daptomycin, YH-16, choriogonadotropin alfa, filgrastim, cetrorelix, interleukin-2, aldesleukin, teceleulin, denileukin diftitox, interferon alfa-n3 (injection), interferon alfa-n1, DL-8234, interferon, Suntory (gamma-la), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alfa, collagenase, carperitide, recombinant human epidermal growth factor (topical gel, wound healing), DWP401, darbepoetin alfa, epoetin omega, epoetin beta, epoetin alfa, desirudin, lepirudin, bivalirudin, nonacog alpha, Mononine, eptacog alfa (activated), recombinant Factor VIII+VWF, Recombinate, recombinant Factor VIII, Factor VIII (recombinant), Alphnmate, octocog alfa, Factor VIII, palifermin, Indikinase, tenecteplase, alteplase, pamiteplase, reteplase, nateplase, monteplase, follitropin alfa, rFSH, hpFSH, micafungin, pegfilgrastim, lenograstim, nartograstim, sermorelin, glucagon, exenatide, pramlintide, iniglucerase, galsulfase, Leucotropin, molgramostirn, triptorelin acetate, histrelin (subcutaneous implant, Hydron), deslorelin, histrelin, nafarelin, leuprolide sustained release depot (ATRIGEL), leuprolide implant (DUROS), goserelin, somatropin, Eutropin, KP-102 program, somatropin, somatropin, mecasermin (growth failure), enlfavirtide, Org-33408, insulin glargine, insulin glulisine, insulin (inhaled), insulin lispro, insulin detemir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alfa, trafermin, ziconotide, taltirelin, diboterminalfa, atosiban, becaplermin, eptifibatide, Zemaira, CTC-111, Shanvac-B, HPV vaccine (quadrivalent), octreotide, lanreotide, ancestim, agalsidase beta, agalsidase alfa, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omnapatrilat, recombinant serum albumin, certolizumab pegol, glucarpidase, human recombinant C1 esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alfa-n3 (oral), belatacept, transdermal insulin patches, AMG-531, MBP-8298, Xerecept, opebacan, AIDSVAX, GV-1001, LymphoScan, ranpimase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, rornidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, T-10, ularitide, depelestat, hematide, Chrysalin (topical), rNAPc2, recombinant Factor V111 (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, AOD-9604, linaclotid eacetate, *CETi*-1, Hemospan, VAL (injectable), fast-acting insulin (injectable, Viadel), intranasal insulin, insulin (inhaled), insulin (oral, eligen), recombinant methionyl human leptin, pitrakinra subcutancous injection, eczema), pitrakinra (inhaled dry powder, asthma), Multikine, RG-1068, MM-093, NBI-6024, AT-001, PI-0824, Org-39141, Cpn10(autoimmune iseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alfa-n3 (topical), IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85A vaccine (tuberculosis), FARA04, BA-210, recombinant plague F1V vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, P1A, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 11 In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCRI, AT-1100 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OSI, AC-162352, PRX-302, LFn-p24 fusion vaccine (Therapore), EP-1043, *S. pneumoniae* pediatric vaccine, malaria vaccine, *Neisseria meningitidis* Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, ViaDerm), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, and TP-9201.

Expression of polypeptides in the yeast strains may be effected using methods known in the art. To express exogenous polypeptides in yeast cells, a polynucleotide sequence encoding the polypeptide is preferably ligated into a nucleic acid construct suitable for yeast cell expression. Such a nucleic acid construct includes a promoter sequence for directing transcription of the polynucleotide sequence in the cell in a constitutive or inducible manner.

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

It will be appreciated that the nucleic acid construct of some embodiments of the invention can also utilize homologues (e.g. glucoamylase homologues) which exhibit the desired activity. Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the sequence reported under its GenBank Accession number, as determined using the BestFit software of the Wisconsin sequence analysis package, utilizing the Smith and Waterman algorithm, where gap weight equals 50, length weight equals 3, average match equals 10 and average mismatch equals −9.

The polypeptides may be expressed with a leader sequence for external extraction from the cell.

In one embodiment, the polypeptide which is expressed is *Aspergillus niger* glucoamylase and the leader sequence is of *Aspergillus niger* glucoamylase.

In another embodiment, the polypeptide which is expressed is *Aspergillus niger* glucoamylase and the leader sequence is of the *Aspergillus niger* alpha amylase gene.

Nucleic acid sequences of the polypeptides of some embodiments of the invention may be optimized for yeast expression. Examples of such sequence modifications include, but are not limited to, an altered G/C content to more closely approach that typically found in the yeast species/strain of interest, and the removal of codons atypically found in the yeast species/strain commonly referred to as codon optimization.

The phrase "codon optimization" refers to the selection of appropriate DNA nucleotides for use within a structural gene or fragment thereof that approaches codon usage within the yeast species/strain of interest. Therefore, an optimized gene or nucleic acid sequence refers to a gene in which the nucleotide sequence of a native or naturally occurring gene has been modified in order to utilize statistically-preferred or statistically-favored codons within the yeast species/strain.

The present invention further comprises cultures of the yeast strains of the present invention.

Thus, according to another aspect of the present invention there is provided a culture comprising the yeast strains described herein and a culture medium.

In one embodiment, the culture medium is a solid medium.

In another embodiment, the culture medium is a liquid medium.

The medium used in yeast cell culturing may be any general medium appropriate for growth of a host cell such as a minimal medium or a complex medium including an appropriate supplement.

In one embodiment, the medium is sterile.

In another embodiment, the medium is xeno-free.

An exemplary liquid medium contemplated by the present inventors is yeast extract peptone dextrose (YPD).

Other media contemplated by the present inventors include corn, molasses, sugar beet, sugarcane, *Panicum virgatum, Miscanthus*, and pulp.

In order for the yeast cells to generate ethanol, the culture medium preferably comprises a carbon source.

The carbon source may be a monosaccharide, a disaccharide, a polysaccharide, and others. The carbon source may be an assimilable sugar. An assimilable sugar may be a hexose or a pentose. Specifically, glucose, maltose, fructose, mannose, galactose or others, including combinations of the above may be used as the carbon source.

Exemplary amounts of glucose are between 1%-50%, more preferably between 1%-40%, more preferably between 1%-30% and even more preferably between 1%-5%.

In one embodiment, the carbon source is a lignocellulosic biomass, processed lignocellulosic biomass, pulp, paper, paper-based products, carbohydrate-rich industrial waste, and combinations thereof. The naturally occurring lignocellulosic biomass may comprise size-reduced softwood, sugarcane bagasse, wheat straw, corn stover, switchgrass, miscanthus, and combinations thereof. Additionally, the carbon source may be a carbohydrate-rich industrial waste selected from the group consisting of food waste, components of municipal solid waste, and combinations thereof.

Other contemplated carbon sources include glucose, maltose, starch, cellulose, glycerol, acetate, sucrose, fructose, galactose, melibiose, ethanol, oleate, manose, arabinose, xylose, ribose, cellobiose, trehalose, lactulose, lactose, chitobiose, chitin, xylobiose, rutinulose, rutinose, melibiulose, mannobiose, gentiobiulose, maltulose, palatinose, turanose, gentiobiose, laminaribiose, sophorose, isomaltose, nigerose, kojibiose, glyceraldehyde, pectin, amylopectin, glycogen, amylose, callose, laminarin, chrysolaminarin, xylan, arabinoxylan, mannan, fucoidan, galactomannan, glucopyranose, glycan, fructo-oligosaccharides, mannan oligosaccharides, galacto-oligosaccharide, inulins, erythrose, threose, mannoheptulose, erythrulose, sedoheptulose, allose, altrose, gulose, idose, talose, psicose, sorbose, tagatose, lyxose, xylulose, ribulose, furanose, ketotriose, aldotrioses, erythritol, threitol, arabitol, xylitol, ribitol, mannitol, sorbitol, galactitol, fucitol, iditol, inositol, volemitol, isomalt, maltitol, lactitol, maltotriitol, maltotetraitol, polyglycitol, sugar acids, hemicellulose, and lignin.

The medium may further comprise additional components such as bacto-agar, antibiotics, a nitrogen source, a salt, a trace element, and a combination thereof.

According to a particular embodiment, the medium comprises at least one synthetic component.

The yeast of the present invention may be cultured in order to produce ethanol.

The yeast strains of the present invention may be used in the baking industry. Thus, the present invention also contemplates an edible dough comprising the yeast. In addition, yeast extracts prepared from the yeast strains described herein may be used to prepare a variety of foods and beverages. Furthermore, the present invention contemplates both food and beverages comprising the yeast (preferably non-genetically modified forms thereof) strains of the present invention. In one embodiment, the food is an animal feed.

The yeast strains of the present invention may further be used in the pharmaceutical industry and/or as a human food and animal feed supplement.

The present inventors also contemplate increasing the ability of a yeast strain to propagate in and/or survive alcohol stress by mutating at least one site on the genome of a yeast having a location as set forth in Tables 11 or 12.

The term "alcohol" refers to an organic compound in which the hydroxyl functional group (—OH) is bound to a saturated carbon atom.

Exemplary alcohols contemplated by the present include, but are not limited to methanol, ethanol, butanol, phenyl ethanol and propanol.

In a preferred embodiment, the alcohol is ethanol.

Methods of introducing nucleic acid alterations into the yeast genome are well known in the art [see for example Menke D. Genesis (2013) 51:-618; Capecchi, Science (1989) 244:1288-1292; Santiago et al. Proc Natl Acad Sci USA (2008) 105:5809-5814; International Patent Application Nos. WO 2014085593, WO 2009071334 and WO 2011146121; U.S. Pat. Nos. 8,771,945, 8,586,526, 6,774,279 and UP Patent Application Publication Nos. 20030232410, 20050026157, US20060014264; the contents of which are incorporated by reference in their entireties] and include targeted homologous recombination, site specific recombinases, PB transposases and genome editing by engineered nucleases. Agents for introducing nucleic acid alterations to a gene of interest can be designed publically available sources or obtained commercially from Transposagen, Addgene and Sangamo Biosciences.

Following is a description of various exemplary methods used to introduce nucleic acid alterations into a genome and agents for implementing same that can be used according to specific embodiments of the present invention.

Genome Editing using engineered endonucleases—this approach refers to a reverse genetics method using artificially engineered nucleases to cut and create specific double-stranded breaks at a desired location(s) in the genome, which are then repaired by cellular endogenous processes such as, homology directed repair (HDS) and non-homologous end-joining (NFfEJ). NFfEJ directly joins the DNA ends in a double-stranded break, while HDR utilizes a homologous sequence as a template for regenerating the missing DNA sequence at the break point. In order to introduce specific nucleotide modifications to the genomic DNA, a DNA repair template containing the desired sequence must be present during HDR. Genome editing cannot be performed using traditional restriction endonucleases since most restriction enzymes recognize a few base pairs on the DNA as their target and the probability is very high that the recognized base pair combination will be found in many locations across the genome resulting in multiple cuts not limited to a desired location. To overcome this challenge and create site-specific single- or double-stranded breaks, several distinct classes of nucleases have been discovered and bioengineered to date. These include the meganucleases, Zinc finger nucleases (ZFNs), transcription-activator like effector nucleases (TALENs) and CRISPR/Cas system.

*Meganucleases*—Meganucleases are commonly grouped into four families: the LAGLIDADG (SEQ ID NO: 30) family, the GIY-YIG (SEQ ID NO: 31) family, the His-Cys box family and the HNH family. These families are characterized by structural motifs, which affect catalytic activity and recognition sequence. For instance, members of the LAGLIDADG (SEQ ID NO: 30) family are characterized by having either one or two copies of the conserved LAGLIDADG (SEQ ID NO: 30) motif. The four families of meganucleases are widely separated from one another with respect to conserved structural elements and, consequently, DNA recognition sequence specificity and catalytic activity. Meganucleases are found commonly in microbial species and have the unique property of having very long recognition sequences (>14 bp) thus making them naturally very specific for cutting at a desired location. This can be exploited to make site-specific double-stranded breaks in genome editing. One of skill in the art can use these naturally occurring meganucleases, however the number of such naturally occurring meganucleases is limited. To overcome this challenge, mutagenesis and high throughput screening methods have been used to create meganuclease variants that recognize unique sequences. For example, various meganucleases have been fused to create hybrid enzymes that recognize a new sequence. Alternatively, DNA interacting amino acids of the meganuclease can be altered to design sequence specific meganucleases (see e.g., U.S. Pat. No. 8,021,867). Meganucleases can be designed using the methods described in e.g., Certo, M T et al. Nature Methods (2012) 9:073-975; U.S. Pat. Nos. 8,304,222; 8,021,867; 8,119,381; 8, 124,369; 8, 129,134; 8,133,697; 8,143,015; 8,143,016; 8, 148,098; or 8, 163,514, the contents of each are incorporated herein by reference in their entirety. Alternatively, meganucleases with site specific cutting characteristics can be obtained using commercially available technologies e.g., Precision Biosciences' Directed Nuclease Editorm genome editing technology.

ZFNs and TALENs—Two distinct classes of engineered nucleases, zinc-finger nucleases (ZFNs) and transcription activator-like effector nucleases (TALENs), have both proven to be effective at producing targeted double-stranded breaks (Christian et al., 2010; Kim et al., 1996; Li et al., 2011; Mahfouz et al., 2011; Miller et al., 2010).

Basically, ZFNs and TALENs restriction endonuclease technology utilizes a non-specific DNA cutting enzyme which is linked to a specific DNA binding domain (either a series of zinc finger domains or TALE repeats, respectively). Typically a restriction enzyme whose DNA recognition site and cleaving site are separate from each other is selected. The cleaving portion is separated and then linked to a DNA binding domain, thereby yielding an endonuclease with very high specificity for a desired sequence. An exemplary restriction enzyme with such properties is FokI. Additionally FokI has the advantage of requiring dimerization to have nuclease activity and this means the specificity increases dramatically as each nuclease partner recognizes a unique DNA sequence. To enhance this effect, FokI nucleases have been engineered that can only function as heterodimers and have increased catalytic activity. The heterodimer functioning nucleases avoid the possibility of unwanted homodimer activity and thus increase specificity of the double-stranded break.

Thus, for example to target a specific site, ZFNs and TALENs are constructed as nuclease pairs, with each member of the pair designed to bind adjacent sequences at the targeted site. Upon transient expression in cells, the nucleases bind to their target sites and the FokI domains heterodimerize to create a double-stranded break. Repair of these double-stranded breaks through the nonhomologous end-joining (NHEJ) pathway most often results in small deletions or small sequence insertions. Since each repair made by NHEJ is unique, the use of a single nuclease pair can produce an allelic series with a range of different deletions at the target site. The deletions typically range anywhere from a few base pairs to a few hundred base pairs in length, but larger deletions have successfully been generated in cell culture by using two pairs of nucleases simultaneously (Carlson et al., 2012; Lee et al., 2010). In addition, when a fragment of DNA with homology to the targeted region is introduced in conjunction with the nuclease pair, the double-stranded break can be repaired via homology directed repair to generate specific modifications (Li et al., 2011; Miller et al., 2010; Urnov et al., 2005).

Although the nuclease portions of both ZFNs and TALENs have similar properties, the difference between these engineered nucleases is in their DNA recognition peptide. ZFNs rely on Cys2-His2 zinc fingers and TALENs on TALEs. Both of these DNA recognizing peptide domains have the characteristic that they are naturally found in combinations in their proteins. Cys2-His2 Zinc fingers typically found in repeats that are 3 bp apart and are found in diverse combinations in a variety of nucleic acid interacting proteins. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities. Approaches for making site-specific zinc finger endonucleases include, e.g., modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries, among others. ZFNs can also be designed and obtained commercially from e.g., Sangamo Biosciences™ (Richmond, Calif.).

Method for designing and obtaining TALENs are described in e.g. Reyon et al. Nature Biotechnology 2012 May; 30(5):460-5; Miller et al. Nat Biotechnol. (2011) 29: 143-148; Cermak et al. Nucleic Acids Research (2011) 39 (12): e82 and Zhang et al. Nature Biotechnology (2011) 29 (2): 149-53. A recently developed web-based program named Mojo Hand was introduced by Mayo Clinic for designing TAL and TALEN constructs for genome editing applications (can be accessed through www(dot)talendesign (dot)org). TALEN can also be designed and obtained commercially from e.g., Sangamo Biosciences™ (Richmond, Calif.).

CRISPR-Cas System—Many bacteria and archea contain endogenous RNA-based adaptive immune systems that can degrade nucleic acids of invading phages and plasmids. These systems consist of clustered regularly interspaced short palindromic repeat (CRISPR) genes that produce RNA components and CRISPR associated (Cas) genes that encode protein components. The CRISPR RNAs (crRNAs) contain short stretches of homology to specific viruses and plasmids and act as guides to direct Cas nucleases to degrade the complementary nucleic acids of the corresponding pathogen. Studies of the type II CRISPR/Cas system of *Streptococcus pyogenes* have shown that three components form an RNA/protein complex and together are sufficient for sequence-specific nuclease activity: the Cas9 nuclease, a crRNA containing 20 base pairs of homology to the target sequence, and a trans-activating crRNA (tracrRNA) (Jinek et al. Science (2012) 337: 816-821). It was further demonstrated that a synthetic chimeric guide RNA (gRNA) composed of a fusion between crRNA and tracrRNA could direct Cas9 to cleave DNA targets that are complementary to the crRNA in vitro. It was also demonstrated that transient expression of Cas9 in conjunction with synthetic gRNAs can be used to produce targeted double-stranded brakes in a variety of different species (Cho et al., 2013; Cong et al., 2013; DiCarlo et al., 2013; Hwang et al., 2013a,b; Jinek et al., 2013; Mali et al., 2013).

The CRIPSR/Cas system for genome editing contains two distinct components: a gRNA and an endonuclease e.g. Cas9.

The gRNA is typically a 20 nucleotide sequence encoding a combination of the target homologous sequence (crRNA) and the endogenous bacterial RNA that links the crRNA to the Cas9 nuclease (tracrRNA) in a single chimeric transcript. The gRNA/Cas9 complex is recruited to the target sequence by the base-pairing between the gRNA sequence and the complement genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the Cas9 can cut both strands of the DNA causing a double-strand break. Just as with ZFNs and TALENs, the double-stranded brakes produced by CRISPR/Cas can undergo homologous recombination or NHEJ.

The Cas9 nuclease has two functional domains: RuvC and HNH, each cutting a different DNA strand. When both of these domains are active, the Cas9 causes double strand breaks in the genomic DNA.

A significant advantage of CRISPR/Cas is that the high efficiency of this system coupled with the ability to easily create synthetic gRNAs enables multiple genes to be targeted simultaneously. In addition, the majority of cells carrying the mutation present biallelic mutations in the targeted genes.

However, apparent flexibility in the base-pairing interactions between the gRNA sequence and the genomic DNA target sequence allows imperfect matches to the target sequence to be cut by Cas9.

Modified versions of the Cas9 enzyme containing a single inactive catalytic domain, either RuvC- or HNH-, are called 'nickases'. With only one active nuclease domain, the Cas9 nickase cuts only one strand of the target DNA, creating a single-strand break or 'nick'. A single-strand break, or nick, is normally quickly repaired through the HDR pathway, using the intact complementary DNA strand as the template. However, two proximal, opposite strand nicks introduced by a Cas9 nickase are treated as a double-strand break, in what is often referred to as a 'double nick' CRISPR system. A double-nick can be repaired by either NHEJ or HDR depending on the desired effect on the gene target. Thus, if specificity and reduced off-target effects are crucial, using the Cas9 nickase to create a double-nick by designing two gRNAs with target sequences in close proximity and on opposite strands of the genomic DNA would decrease off-target effect as either gRNA alone will result in nicks that will not change the genomic DNA.

Modified versions of the Cas9 enzyme containing two inactive catalytic domains (dead Cas9, or dCas9) have no nuclease activity while still able to bind to DNA based on gRNA specificity. The dCas9 can be utilized as a platform for DNA transcriptional regulators to activate or repress gene expression by fusing the inactive enzyme to known regulatory domains. For example, the binding of dCas9 alone to a target sequence in genomic DNA can interfere with gene transcription.

There are a number of publically available tools available to help choose and/or design target sequences as well as lists of bioinformatically determined unique gRNAs for different genes in different species such as the Feng Zhang lab's Target Finder, the Michael Boutros lab's Target Finder (E-CRISP), the RGEN Tools: Cas-OFFinder, the CasFinder: Flexible algorithm for identifying specific Cas9 targets in genomes and the CRISPR Optimal Target Finder.

In order to use the CRISPR system, both gRNA and Cas9 should be expressed in a target cell. The insertion vector can contain both cassettes on a single plasmid or the cassettes are expressed from two separate plasmids. CRISPR plasmids are commercially available such as the px330 plasmid from Addgene.

"Hit and run" or "in-out"—involves a two-step recombination procedure. In the first step, an insertion-type vector containing a dual positive/negative selectable marker cassette is used to introduce the desired sequence alteration. The insertion vector contains a single continuous region of homology to the targeted locus and is modified to carry the mutation of interest. This targeting construct is linearized with a restriction enzyme at a one site within the region of homology, electroporated into the cells, and positive selection is performed to isolate homologous recombinants. These homologous recombinants contain a local duplication that is separated by intervening vector sequence, including the selection cassette. In the second step, targeted clones are subjected to negative selection to identify cells that have lost the selection cassette via intrachromosomal recombination between the duplicated sequences. The local recombination event removes the duplication and, depending on the site of recombination, the allele either retains the introduced mutation or reverts to wild type. The end result is the introduction of the desired modification without the retention of any exogenous sequences.

The "double-replacement" or "tag and exchange" strategy—involves a two-step selection procedure similar to the hit and run approach, but requires the use of two different targeting constructs. In the first step, a standard targeting vector with 3' and 5' homology arms is used to insert a dual positive/negative selectable cassette near the location where the mutation is to be introduced. After electroporation and positive selection, homologously targeted clones are identified. Next, a second targeting vector that contains a region of homology with the desired mutation is electroporated into targeted clones, and negative selection is applied to remove the selection cassette and introduce the mutation. The final allele contains the desired mutation while eliminating unwanted exogenous sequences.

Site-Specific Recombinases—The Cre recombinase derived from the P1 bacteriophage and Flp recombinase derived from the yeast *Saccharomyces cerevisiae* are site-specific DNA recombinases each recognizing a unique 34 base pair DNA sequence (termed "Lox" and "FRT", respectively) and sequences that are flanked with either Lox sites or FRT sites can be readily removed via site-specific recombination upon expression of Cre or Flp recombinase, respectively. For example, the Lox sequence is composed of an asymmetric eight base pair spacer region flanked by 13 base pair inverted repeats. Cre recombines the 34 base pair lox DNA sequence by binding to the 13 base pair inverted repeats and catalyzing strand cleavage and religation within the spacer region. The staggered DNA cuts made by Cre in the spacer region are separated by 6 base pairs to give an overlap region that acts as a homology sensor to ensure that only recombination sites having the same overlap region recombine.

Basically, the site specific recombinase system offers means for the removal of selection cassettes after homologous recombination. This system also allows for the generation of conditional altered alleles that can be inactivated or activated in a temporal or tissue-specific manner. Of note, the Cre and Flp recombinases leave behind a Lox or FRT "scar" of 34 base pairs. The Lox or FRT sites that remain are typically left behind in an intron or 3' UTR of the modified locus, and current evidence suggests that these sites usually do not interfere significantly with gene function.

Thus, Cre/Lox and Flp/FRT recombination involves introduction of a targeting vector with 3' and 5' homology arms containing the mutation of interest, two Lox or FRT sequences and typically a selectable cassette placed between the two Lox or FRT sequences. Positive selection is applied and homologous recombinants that contain targeted mutation are identified. Transient expression of Cre or Flp in conjunction with negative selection results in the excision of the selection cassette and selects for cells where the cassette has been lost. The final targeted allele contains the Lox or FRT scar of exogenous sequences.

Transposases—As used herein, the term "transposase" refers to an enzyme that binds to the ends of a transposon and catalyzes the movement of the transposon to another part of the genome.

As used herein the term "transposon" refers to a mobile genetic element comprising a nucleotide sequence which can move around to different positions within the genome of a single cell. In the process the transposon can cause mutations and/or change the amount of a DNA in the genome of the cell.

A number of transposon systems that are able to also transpose in cells e.g. vertebrates have been isolated or designed, such as Sleeping Beauty [Izsvák and Ivics Molecular Therapy (2004) 9, 147-156], piggyBac [Wilson et al. Molecular Therapy (2007) 15, 139-145], Tol2 [Kawakami et al. PNAS (2000) 97 (21): 11403-11408] or Frog Prince [Miskey et al. Nucleic Acids Res. December 1, (2003) 31(23): 6873-6881]. Generally, DNA transposons translocate from one DNA site to another in a simple, cut-and-paste manner. Each of these elements has their own advantages, for example, Sleeping Beauty is particularly useful in region-specific mutagenesis, whereas Tol2 has the highest tendency to integrate into expressed genes. Hyperactive systems are available for Sleeping Beauty and piggyBac. Most importantly, these transposons have distinct target site preferences, and can therefore introduce sequence alterations in overlapping, but distinct sets of genes. Therefore, to achieve the best possible coverage of genes, the use of more than one element is particularly preferred. The basic mechanism is shared between the different transposases, therefore we will describe piggyBac (PB) as an example.

PB is a 2.5 kb insect transposon originally isolated from the cabbage looper moth, *Trichoplusia ni*. The PB transposon consists of asymmetric terminal repeat sequences that flank a transposase, PBase. PBase recognizes the terminal repeats and induces transposition via a "cut-and-paste" based mechanism, and preferentially transposes into the host genome at the tetranucleotide sequence TTAA. Upon insertion, the TTAA target site is duplicated such that the PB transposon is flanked by this tetranucleotide sequence. When mobilized, PB typically excises itself precisely to reestablish a single TTAA site, thereby restoring the host sequence to its pretransposon state. After excision, PB can transpose into a new location or be permanently lost from the genome.

Typically, the transposase system offers an alternative means for the removal of selection cassettes after homologous recombination quit similar to the use Cre/Lox or Flp/FRT. Thus, for example, the PB transposase system involves introduction of a targeting vector with 3' and 5' homology arms containing the mutation of interest, two PB terminal repeat sequences at the site of an endogenous TTAA sequence and a selection cassette placed between PB terminal repeat sequences. Positive selection is applied and homologous recombinants that contain targeted mutation are identified. Transient expression of PBase removes in conjunction with negative selection results in the excision of the selection cassette and selects for cells where the cassette has been lost. The final targeted allele contains the introduced mutation with no exogenous sequences.

For PB to be useful for the introduction of sequence alterations, there must be a native TTAA site in relatively close proximity to the location where a particular mutation is to be inserted.

Methods for qualifying efficacy and detecting sequence alteration are well known in the art and include, but not limited to, DNA sequencing, electrophoresis, an enzyme-based mismatch detection assay and a hybridization assay such as PCR, RT-PCR, RNase protection, in-situ hybridization, primer extension, Southern blot, Northern Blot and dot blot analysis.

Sequence alterations in a specific gene can also be determined at the protein level using e.g. chromatography, electrophoretic methods, immunodetection assays such as ELISA and western blot analysis and immunohistochemistry.

In addition, one ordinarily skilled in the art can readily design a knock-in/knock-down/knock-out construct including positive and/or negative selection markers for efficiently selecting transformed cells that underwent a homologous recombination event with the construct. Positive selection provides a means to enrich the population of clones that have taken up foreign DNA. Non-limiting examples of such positive markers include glutamine synthetase, dihydrofolate reductase (DHFR), markers that confer antibiotic resistance, such as neomycin, hygromycin, puromycin, and blasticidin S resistance cassettes. Negative selection markers are necessary to select against random integrations and/or elimination of a marker sequence (e.g. positive marker). Non-limiting examples of such negative markers include the herpes simplex-thymidine kinase (HSV-TK) which converts ganciclovir (GCV) into a cytotoxic nucleoside analog, hypoxanthine phosphoribosyltransferase (HPRT) and adenine phosphoribosytransferase (ARPT).

Particular genes which may be knocked-out include, but are not limited to ADH2, ADR1 and its binding site.

Other genes which may be knocked-out/knocked-in are those associated with regulation of C-compounds and/or carbohydrate metabolism. Examples of such include, but are not limited to HAP2, RTG2, HXK2, PFK1, SNF6, PFK26, RGR1, MKS1, GCR2, GAL11, SNF2, GCR1, TAF14, BEM4 and GAL4.

Other genes which may be knocked-out/knocked-in are those that show strong candidate mutations on protein structure include, such as MOG1, MGS1, YJR154W, RTG2, ZRT1, MMP1 RNR2 and MMP1.

According to a particular embodiment, the gene which is knocked-out/knocked-in is ADH2.

According to a particular embodiment, the gene which is knocked-out/knocked-in is ADR1 or a gene comprising its binding site.

Following introduction of the mutation, the yeast strain may be analyzed for improved survival or growth in alcohol as explained herein above.

According to another aspect of the present invention there is provided a method of selecting a yeast strain which is capable of propagating under alcohol stress and/or surviving alcohol stress comprising analyzing for the presence of at least one mutation at a position set forth in Tables 11 or 12, wherein the presence of the mutation is indicative of a yeast strain which is capable of propagating and/or surviving under alcohol stress.

Tracing or detecting whether there is a mutation in the genome of a modified gene-compared to a wild type strain can also be determined by any method known in the art, as further described herein above.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Examples

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the Materials and Methods Intercross: S288c, the haploid laboratory strain that provided the standard yeast genome sequence, and YE-531, a heterothallic haploid strain YE-531 isolated from nature 7, were crossed to create an F1, and the cross population was intercrossed for 5 more generations to create the F6 AIL population using the Ether-zymolyase (EZ) ascospore isolation procedure (Bahalul, et al. 2010). The effective number of segregants was >10$^5$ each generation, far greater than the recommended number of at least 100 individuals per generation to minimize sampling effects on recombination proportions across the genome[13].

Selective DNA Pooling:

Pool construction: A two-stage selection was employed in F6 to obtain the upper tail groups for growth and survival under ethanol stress (FIGS. 1A-D). For both traits, the first stage consisted of mass-selection at an enthanol concentration that provided 35% survivial (based on CFU of the unselected and challenged populations). This level of survival was chosen as one that would provide significant selection while maintaining genetic variation in the selected group. The 35% survival target was obtained with 15% (V/V) ethanol stress for 5 hours. At the end, 300 colonies randomly sampled among the survivors were isolated and stored.

Figure 12B:
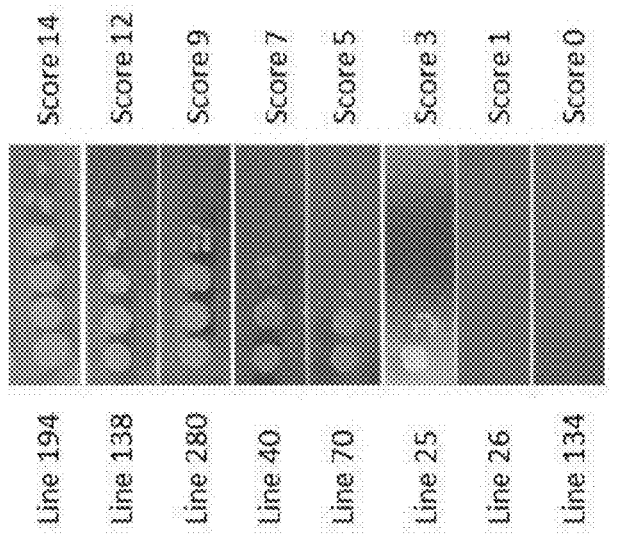
FIGS. 12A-B: An example of ethanol tolerance of the segregants. (A) Growth ability of 11 segregants (out of 300 tested) and the founder S288c in 9.5% (V/V) ethanol. Cells were grown in YPD medium with ethanol at 30° C. for 20 hours, in anaerobic conditions. Final 600 nm absorbance was measured. The mean values and SD are presented. (B) Survival test of 8 segregants (out of 300 tested) in the presence of 19% (V/V) ethanol for 5 hours. Cells in equal concentrations were incubated in YPD medium with ethanol at 30° C. for 5 hours, in anaerobic conditions. Samples were seeded at 1 to 100,000-fold dilutions. Survival score (0-14) was assigned depending on the final dilution showing survival in the spot assay (see examples on the right).
Figure 12A:
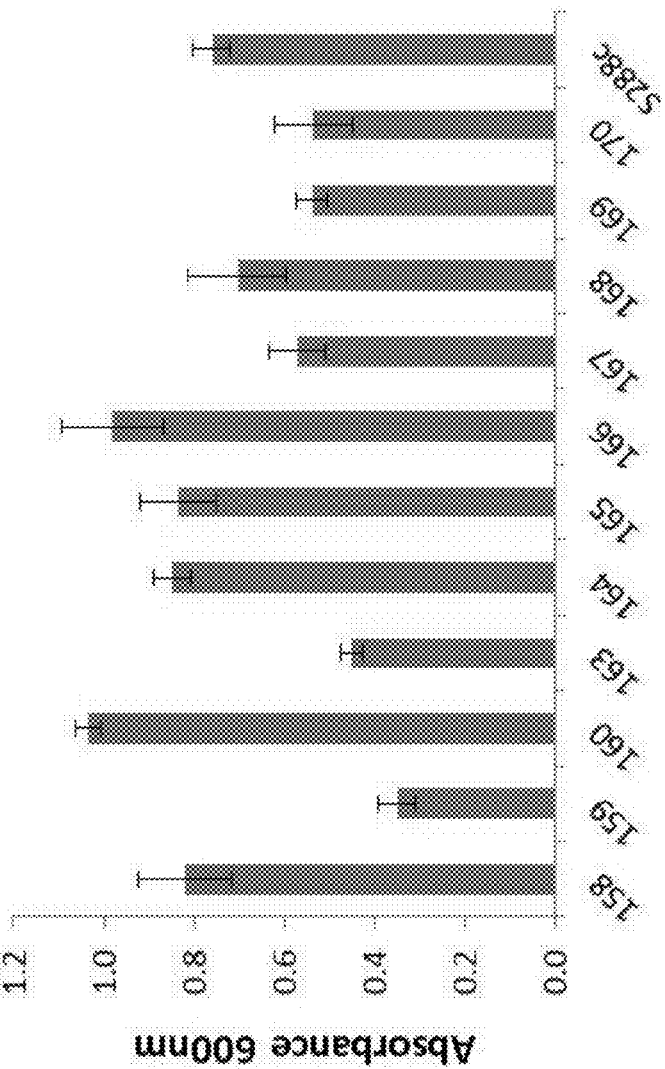

For the second stage of the selection, each of the 300 colonies went through growth and survival tests detailed below (FIGS. 12A-B). Each colony was tested in four independent samples taken from the colony (biological replicates). (FIGS. 12A-B).

For identification of the colonies to make up of the selected growth upper tail, the ability to grow under stress of 9.5% (V/V) ethanol for 22 hours was tested by final OD600 nm measurement. Specifically, 1 ml final volume of a cell culture suspended in YPD liquid media mixed with ethanol, was transferred into one well of a 24 multiwell plate. Anaerobic conditions were obtained using a polyester-based microplate film, designed to minimize evaporation. Each colony was tested in four replicates. Biological samples were separated into two multiwall plates and placed in different areas of each plate. Average and standard deviation of final OD600 nm values were calculated for each tested colony (FIGS. 12A-B). The 90 colonies showing the highest OD values were chosen to form the upper tail. These 90 colonies were tested for ethanol degrading ability to disqualify any segregants with an advantage for ethanol decline under anaerobic condition. Such cultures would deal with the ethanol challenge by degrading the ethanol, rather than resisting its effects. To test for ethanol degrading ability, cultures were suspended in 9.5% (V/V) ethanol and the ethanol concentration of these cultures was determined by Headspace GC-FID (Gas Chromatography with Flame Ionization Detector) before and after overnight growth for 22 hours. Based on the results, 10 segregants suspected of having ethanol degrading activity were excluded.

For the creation of the survival upper tail group, the ability to survive in 19% (V/V) ethanol solution for 5 hours was tested by a spot assay. Namely, 1 ml final volume of a cell culture suspended in YPD liquid media mixed with ethanol, was transferred into one well of a 24 multiwell plate. Anaerobic conditions were obtained using the polyester-based microplate film. A spot assay at 1- to 100,000-fold dilution was done to evaluate cell survival ability. The survival ability test was designed for a short time and under high ethanol stress in order to distinguish between survival and growth under ethanol stress. Here too, each colony was tested in four replicates (FIGS. 12A-B). Each duplicate was assigned a survival score depending on the final dilution showing survival in the spot assay, and selection was on the basis of total score across all four repeats.

The 300 colonies selected in the first stage were ranked on basis of OD in the growth test and serial dilutions in the survival test, and the top 90 most tolerant colonies for each trait were chosen for the pools. For both traits the 90 selected colonies were divided at random into 3 independent groups of 30 colonies each. Division of the total sample into three pools was for the statistical analysis. In addition, 3 independent control pools were prepared from the entire F6 population, each consisting of many thousands of individuals. The F6 culture was harvested for the control pools after recovering from Ether-zymolyase ascospore isolation procedure[21] for 36 hours in YPD media.

Preparation of DNA samples and genotyping by whole-genome deep sequence pool analysis: Genomic DNA from founder strains and pools was extracted with MasterPure yeast DNA purification kit (Epicenter, Madison, Wis.), according to the manufacturer's instructions.

Genotyping was by sequencing. To reduce costs, rather than individually sequence each of the individual trait colonies, whole genome deep sequencing of pools made from the individual colonies was performed. For each of the 6 tail pools (30 colonies per pool) 3 subgroups were formed, each composed of 10 individuals. Based on OD600 nm absorption, an equal number of cells was taken for each individual. Cells for the ten individual of the subgroup were combined, and DNA extracted. After extraction, equal DNA amounts of the 3 subgroups were pooled, representing the 30 individual colonies in each pool). For the control pools, DNA was extracted in pools from 10 OD600 nm cell culture. For accuracy, estimates of allele frequency in the pools were obtained by deep sequencing at very high coverage using Illumina HiSeq 2500 technology, rather than by densitometric methods. Sequencing was generated at paired ends of 100 bp fragments. Genome coverage (Table 1A) was close to or over 1000 for all pools. Sequence quality per base was confirmed using FastQC[43]. All bases were with quality score >20.

TABLE 1A

Sequencing coverage of analyzed pool replicates.
AIL F6 population served as the control.

| Sample | Coverage of reads |
|---|---|
| Control-replicate1 | 3,180 |
| Control-replicate2 | 2,217 |
| Control-replicate3 | 1,842 |
| Growth upper tail replicate1 | 968 |
| Growth upper tail replicate2 | 1,009 |
| Growth upper tail replicate3 | 946 |
| Survival upper tail replicate1 | 1,013 |
| Survival upper tail replicate2 | 951 |
| Survival upper tail replicate3 | 1,019 |
| Random F6 haploid individual | 989 |
| S288c | 705 |
| YE-531 | 1,385 |

DNA reads were aligned to strain S288c reference genome sequence, version R64-1-1[27], and to a YE-531 reference genome that we generated by: (1) Initial assembly of YE-531 High Throuput Sequencing data using Edena assembler[44]; and (2) Extending the contigs using Align-Graph[45] and the S288c genome.

Sequence alignment was done with BWA-mem algorithm, version 0.7.10[46]. Only unique mappings were used in the analysis. PCR duplicates were marked by Picard-Tools 1.123. Alignment manipulations and variant calling were done by GATK best practice v.3.3-0[47]. Suggested protocol with the default parameters was used. In addition to variant calling with GATK, MUMmer 3 package[48] variant was used, calling to compare between S288c and YE-531 assemblies. For QTL analysis we used only SNPs identified by both GATK and MUMmer.

Frequency estimates: Allele frequency was estimated by GATK. To further improve the estimates, frequency along each chromosome was smoothed using LOESS local regression with span (i.e. window)=80 SNPs and degree=2. The LOESS implementation in R was used that is based on the 1998 version of cloess package of Cleveland, Grosse and Shyu[22]. The smoothed allele frequencies were used to calculate D-value, the frequency difference between the tail groups and the entire population of F6.

Confirmation of pool frequency estimates: Pool frequency estimates of 2 SNPs were confirmed by real time PCR coupled to high resolution melting (HRM) genotyping[49] using ECO real time PCR system (Illumina) (Table 1B, herein below).

TABLE 1B

Primers used for FIRM analyses

| Name | Sequence 5' to 3' | Amplicon length |
|---|---|---|
| UPT20-F | TCTTTCAAGATTTTCAGCAGAAGCA SEQ ID NO: 26 | 114 |
| UPT20-R | AAAAGTTAGAGGGAGATGATGAGCA SEQ ID NO: 27 | |
| PRP28-F | ACCAGGATGTCACAACCCTC SEQ ID NO: 28 | 105 |
| PRP28-R | TCATAGTTGCTCTCTTTGGACCAT SEQ ID NO: 29 | |

Thirty individuals randomly chosen from the general population were genotyped for both SNPs, along with two groups of 30 individuals from each of the tail pools of growth and survival. SNP frequency was calculated for each group and compared to that obtained from deep sequencing of the pools.

Phylogenetic Analysis: Phylogenetic analysis was performed on the whole genome sequence of 15 strains using RealPhy[50]. The natural strain YE-531 was compared with a selection of commercial and wild strains available in the SGD database[27]. Some of the strains represent main lineages that appear in Liti et al 2009[18]. A radial phylogenetic tree is presented in FIG. 9.

Quality control: For QTL definition only SNPs agreed between GATK and MUMmer were used. The frequency of each variant was estimated in AIL F6 population pool samples twice, based on S288c and YE-531 reference genomes separately. Variants that differed in their frequency obtained by the two reference genomes were removed from the analysis.

Since YE-531 is haploid, it can be expected that any allele that differs from S288c will have YE-531 frequency of 1. Therefore, markers with YE-531 frequency <1 were removed, as they might reflect sequencing and mapping errors. Markers having MAF<0.05 for pool samples were removed from the analysis as well. After filtration, 35,134 SNPs for growth and 35,019 for survival were used for mapping QTL.

Statistical Analysis

Notation

Let $pM_{ijk}$ be the LOESS smoothed frequency estimate (eFrequency) of the YE-531 allele of the $i^{th}$ marker in the $j^{th}$ pool of the $k^{th}$ category, where, I=1 to M markers used in the study, j=1 to 3, is the serial number of the pool within its category, k=1 to 3 is the category, where 1=Growth selected pools; 2=Survival selected pools; 3=Control (AIL-F6 population) pools.

Thus, pM111 would be the eFrequency of the Marker 1, in pool 1, of the growth selected pools.

Marker-trait association was determined by a single marker test, where CWER P-value of the $i^{th}$ marker for the $k^{th}$-category was set equal to $P_{i.k}$=2×area of the standard normal curve to the right of $Z_{i.k}$=$D_{i.k}$/SE(D..k) where, $D_{i.1}$=Avg($pM_{i.1}$)−Avg($pM_{i.3}$), for the growth trait pools, and $D_{i.2}$=Avg($pM_{i.2}$)−Avg($pM_{i.3}$), for the survival trait pools.

Avg($pM_{i.1}$) is the average of pMi taken across the three growth pools,

Avg($pM_{i.2}$) is the average of pMi taken across the three survival pools,

Avg($pM_{i.3}$) is the average of pMi taken across the three AIL-F6 control pools.

SE(D..k) is the standard error associated with Di. 1 and Di.2, respectively.

By definition, the SE of a "treatment" effect (the above D..k), is the expected standard deviation under the null hypothesis that the treatment has no effect. An empirical estimate of the SE(D..k) was obtained based on the assumption that the variance of marker allele frequency among pools of the same category (i.e., among growth, survival or control pools), is affected by sampling variation and technical variation, but do not represent a real difference in marker allele frequency. Thus, it is a measure of sampling variation among pools of the given category under the null hypothesis[7,25,52]. SE(D..k) was obtained by appropriate weighting of these variances estimates.

To implement this, for each marker the variance of the marker allele frequency across the three F6 control pools was calculated. The locally smoothed variance between control pools across span of 10% of the markers was calculated to obtain VarPijk for each marker, an empirical estimate of the sampling variation among control pools under the null hypothesis. Similarly, for each marker x trait combination, the variance of marker allele frequency across all three tail pools was calculated. Then the locally smoothed variance across span of 10% of the markers for growth and survival pools, respectively (VarSijk..1 and VarSijk..2) was calculated.

Since Avg(pMi) for the various categories is an average of 3 pools, $SE^2(D_{ijk})$=VarSijk/3+VarPijk/3.

Declaring significance and QTL mapping: To account for the multiple tests involved in the present study (>35,000 marker tests for each trait), the False Discovery Rate (FDR) criterion[52] was used, with alpha=0.2 to set experiment wide significance for the individual marker x trait combination (FIGS. 5A-C).

QTL boundaries were defined with a 1.0 log-drop procedure as in Lipkin et. al. 2016[3]. Note that a single QTL may be considered as 2 QTLs when two adjacent peaks are observed. QTLs of the two traits were considered as overlap when their boundaries were partly overlapping.

Marker allele substitution effect: Allele substitution effect (δ) was calculated for each marker located in a QTL following Darvasi and Soller (Darvasi and Soller 1994), except that instead of twice the allele substitution effect (2δ), obtained by comparing 2 extreme tails, here δ was obtained by comparing each tail to the unselected F6 population. The phenotypic means of each tail and control F6 isolates were obtained from ethanol exposure experiments, similarly to those described in the second stage of the Pool construction.

As detailed above, a two-stage selection scheme was used (FIGS. 1A-D). Selection proportions in the tails were 35% and 30% in the first and the second stage, together 10.5%. However, as the design used here was a 1-tail design (unlike Darvasi and Soller (Darvasi and Soller 1994) 2-tails design), average selection was equivalent to 21%.

QTLs allele effect and contribution to the phenotypic variance: The average effects of the top three markers in each QTL was used to estimate the QTL allele effect, δ. The contribution of the QTL to the phenotypic variation was calculated as $VarQ=2pq\delta^2$ (Mosig, et al. 2001), where p and q are the means of allele frequencies of the same three markers used to estimate the QTL effect. VarP, the phenotypic variance of each trait in the entire F6 population, was obtained from ethanol exposure experiments, performed similarly to the second stage selection procedures, and the proportional contribution of the QTL to VarP was calculated as VarQNarP.

Reciprocal Hemizygosity Analysis (RHA): For RHA (Steinmetz, et al. 2002), deletions were made in the S288c and YE-531 haploid backgrounds, using the strategy of Yeast Deletion Project (worldwideweb(dot)sequence(dot)stanford(dot)edu/group/yeast_deletion_project/proj ect_desc), based on the deletion strain collection (EUROSCARF). Deletion KanMX "cassettes" were constructed using PCR reactions for the BY4741 deletion strains, with primers designed 50-250 bp upstream and downstream of each candidate ORF (Table 1C). Selection for transformants was made on agar plates with G418 (Geneticin). Selected colonies were further verified by PCR (Table 1D). Reciprocal strains were generated by crossing the deletion parental with the other parental strain.

TABLE 1C

Oligonucleotides utilized as specific deletion primers for "cassettes" constructions for transformation (for RHA)

| Name | Sequence 5' to 3' |
|---|---|
| YBR001C-F | GCGCTTGTAGGAACTGT T (SEQ ID NO: 1) |
| YBR001C-R | GACGATTTAGAGTAAGG TC (SEQ ID NO: 2) |
| YGL255W-F | GCATTAGCTCGATGACT TAG (SEQ ID NO: 3) |
| YGL255W-R | CAGTCTCGGACAATAAA TACGC (SEQ ID NO: 4) |
| YJR154W-F | CATGTGTTGATAGCAGG TGACG (SEQ ID NO: 5) |

TABLE 1C-continued

Oligonucleotides utilized as specific deletion primers for "cassettes" constructions for transformation (for RHA)

| Name | Sequence 5' to 3' |
|---|---|
| YJR154W-R | CTATTCTAGTACTTCCCT GCTG (SEQ ID NO: 6) |
| YLL061W-F | GATGCCAGGAAATAAAT GCG (SEQ ID NO: 7) |
| YLL061W-R | GAATGATATTCTAGGCC CTG (SEQ ID NO: 8) |
| YNL218W-F | GACATTCAATCATCGGT TGC (SEQ ID NO: 9) |
| YNL218W-R | CAATGCCGCGTCTACAA TTC (SEQ ID NO: 10) |
| YGL252C-F | GAATGCCGAGATAGGAT AAC (SEQ ID NO: 11) |
| YGL252C-R | CACCTTCTTGTTGTTCAA AC (SEQ ID NO: 12) |
| YMR303C-F | GCTATAGCATGCCTATC AC (SEQ ID NO: 13) |
| YMR303C-R | TCACTCGTGCTAGCAAA C (SEQ ID NO: 14) |
| YJR074W-F | GGACTGACTCCTTCATC GC (SEQ ID NO: 15) |
| YJR074W-R | CACTTTCTTCGCTGCTG G (SEQ ID NO: 16) |

Deletion KanMX "cassettes" were constructed using PCR reactions for the BY4741 deletion strains, with primers designed (50-250) bp upstream and downstream each candidate ORF. The reaction was made to extend the specific ORF homology to enable mitotic recombination of the gene disruption cassette. F, forward primers; R, reverse primers.

TABLE 1D

Specific primers that were used for deletion strain confirmation (for RHA)

| Name | Sequence 5' to 3' |
|---|---|
| KanMX+ (used for all tests) | GCGCTTGTAGGAACTGTT (SEQ ID NO: 17) |
| YBR001C-CheckR | TCAAGTTGTGTAAAGGCTC (SEQ ID NO: 18) |
| YGL255W-CheckR | CAAGTGGTACCAGAATACG (SEQ ID NO: 19) |
| YJR154W-CheckR | GGTGTGTCTGATACTCCTGC (SEQ ID NO: 20) |
| YLL061W-CheckR | GCACGTCCAGGTTCTGTGAC (SEQ ID NO: 21) |
| YNL218W- CheckR | AGATAATCAAGGATCCACC (SEQ ID NO: 22) |
| YGL252C-CheckR | GTTTAAGCACCGATGATACC (SEQ ID NO: 23) |
| YMR303C- CheckR | GAGACGATTCAGAGGAGCA (SEQ ID NO: 24) |

TABLE 1D-continued

Specific primers that were used for
deletion strain confirmation (for RHA)

| Name | Sequence 5' to 3' |
|---|---|
| YJR074W- CheckR | CGAATATCATCAACCTCCTG (SEQ ID NO: 25) |

Selected colonies after "cassette" transformation were further verified by PCR for correct replacement of the gene with KanMX. PCR was performed using internal and external primers to the cassette. The internal forward primer was KanMX+, for all tests; the external reverse primer was CheckR, which is specific to each site. Appearance of PCR products of the expected size proved the correct replacement of the gene with KanMX.

To determine whether one allele is advantageous over the other in the RHA tests, growth and survival of the two reciprocal deletion strains were tested under ethanol stress, exactly as in the second stage of the pool construction. 6 genes were tested for a single trait only (growth or survival), and 2 genes were tested for both traits, making a total of 10 gene×trait tests. Each deletion strain was tested in 2-5 "batches", each batch consisting of four replicates. For growth, the performance of the strain under 9.5-11% ethanol was taken as the mean OD600 nm across the replicates and batches. For survival, each replicate was graded under 18% or 19% ethanol. All candidate genes were first tested under the ethanol concentrations originally used (9.5% for growth and 19% for survival) to evaluate the F6 phenotypic abilities. Since only a single candidate gene was tested in the F1 background, unlike the tests performed in the F6, in some cases several more batches under slightly higher/lower ethanol concentrations were performed to detect differences between alternative alleles. The performance of the deletion strain was taken as the sum of grades across replicates and batches. Grade for a replicate was assigned as follows. Each replicate was tested at five 10-fold dilutions, giving a total of 6 dilutions (including 0 dilution); and each dilution was scored 0 (no growth) to 3 (full growth) by a visual inspection. The grade for the replicate was the simple sum of the dilution scores.

For example, Gene YNL218W deletion strain S288c-Δ::kanMX/YE-531 was graded in four batches. For Batch 1, Replicate 1, results were: Dilution 0, score 2; Dilution 1, score 2; Dilution 2, score 1; Dilution 3, score 1; Dilution 4 and 5, score 0. Total score: 6. Replicates 2, 3 and 4 had total scores 5, 7, 7, respectively, giving the grade 25 for Batch 1. In the same way, scores, 19, 19, 40 were obtained for Batches 2, 3, 4, for the grade 103 for S288c-Δ::kanMX/YE-531 deletion of the gene YNL218W. The average value was then calculated as the grade divided by the number of observations (103/96).

A two-way ANOVA (R aov) with batch and allele as main effects was used to test the null hypothesis of equal growth of the alternative deletion strains. A Non-parametric ANCOVA (Young and Bowman 1995) test was used to test the null hypothesis of equal slopes obtained from regressing survival scores on serial dilutions.

For the significance of the overall hypothesis that "effects on ethanol tolerance of alternative alleles at single genes as obtained by QTL mapping procedures, are validated by the RHA analyses", a nonparametric sign test was used to test the null hypothesis that the favorable allele identified by QTL mapping and the favorable allele identified by RHA are independent. To do this, the present inventors compared the favorable allele by QTL mapping and favorable allele by RHA for each of 10 gene x trait combinations. Results of all three analyses are shown in Table 1E.

TABLE 1E

Comparison of QTL and RHA effects

| Gene | Standard name | Trait | Favor QTL allele | RHA Allele effect S288c-Δ::kanMX/ YE-531 | RHA Allele effect YE-531-Δ::kanMX/ S288c | Favor RHA allele | P | Sign |
|---|---|---|---|---|---|---|---|---|
| ADH2 | YMR303C | G | YE-531 | 0.594 | 0.500 | YE-531 | 0.010 | + |
| MOG1 | YJR074W | G | YE-531 | 0.521 | 0.433 | YE-531 | 0.0020 | + |
| None | YJR154W | G | YE-531 | 0.649 | 0.636 | YE-531 | 0.38 | + |
| RTG2 | YGL252C | G | S288c | 0.819 | 0.830 | S288c | 0.42 | + |
| MGS1 | YNL218W | S | S288c | 1.073 | 1.135 | S288c | 0.0060 | + |
| ZRT1 | YGL255W | S | S288c | 1.250 | 1.313 | S288c | 0.40 | + |
| NTH2 | YBR001C | S | S288c | 0.986 | 0.986 | EQUAL | 0.19 | NI |
| MMP1 | YLL061W | S | S288c | 1.010 | 1.063 | S288c | 0.18 | + |
| None | YJR154W | S | YE-531 | 0.992 | 0.767 | YE-531 | 0 | + |
| ADH2 | YMR303C | S | YE-531 | 1.104 | 1.083 | YE-531 | 0.20 | + |

G, growth;
S, survival;
RHA Allele effect, average effect;
P, CWER p-value by ANOVA (growth trait) or nonparametric ANCOVA (survival).
Sign: +, QTL mapping and RHA agree on favorable allele;
−, QTL and RHA disagree;
EQUAL, the two alleles have exactly the same effect on RHA;
NI, comparison is not informative for sign test.

Testing candidate causative mutations in three-dimensional (3D) protein structures: For gene with a known protein structure, the PDB data (Bernstein, et al. 1977) were used. For proteins with unknown structure, the structure using the servers Phyre2 (Kelley, et al. 2015) and I-TASSER (Roy, et al. 2010; Yang, et al. 2015; Zhang 2008) was predicted. The location of non-synonymous mutations on the 3D structure of tested proteins was identified. In addition, the level of evolutionary conservation based on each mutation was estimated using ConSurf software (Ashkenazy, et al. 2010; Celniker, et al. 2013); favorable sites for protein-protein interaction were detected by ODA (Fernandez-Recio, et al. 2005); effects of mutations on protein stability was predicted by DUET (Pires, et al. 2014).

Ethanol production assay: Incubation of 200 ml final volume, of 10' cells/ml yeast cells suspended in ground degraded corn prepared following the method described by Bothast and Schlicher 2005, was in 250 ml Erlenmeyer flasks at 32.5° C. under constant agitation (160 rpm). After 17 hr of incubation, ethanol levels of the sample supernatant and of reference ethanol standards (European Reference Materials) were quantified using Thermo Scientific Trace 1300 gas chromatograph with flame ionization detector. Glucose levels were quantified using glucose (HK) assay kit (Sigma Aldrich) initially and after 17 hr.

Results

Figure 9:
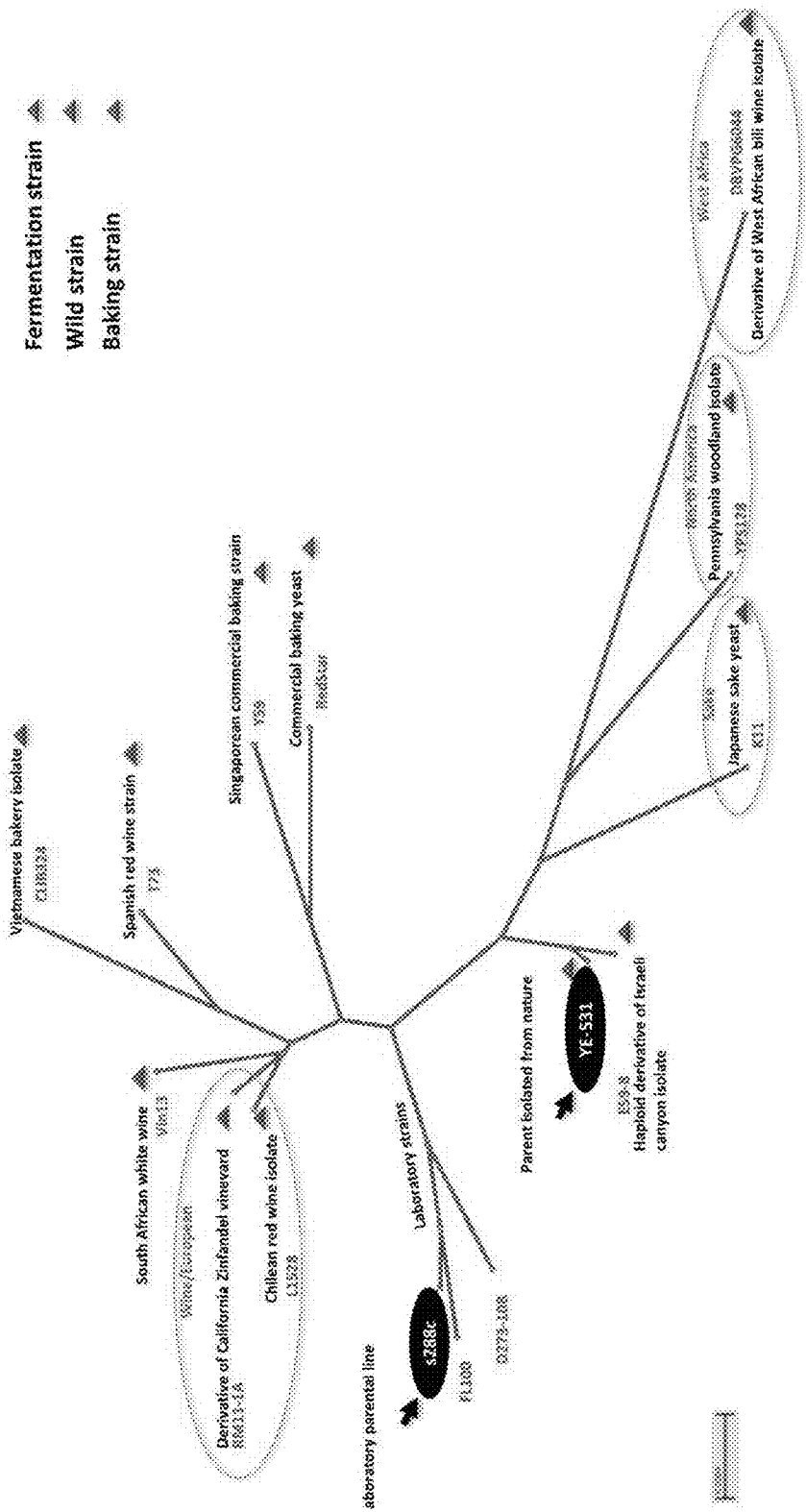
FIG. 9 illustrates a phylogenetic analysis, based on whole genome sequences, of the AIL parental lines in relation to known *S. cerevisiae* strains representing different lineages and groups, Black text, strain description; red text, full genome name of the strain; green circle, clean-lineages[18]; arrows and black ellipses, AIL parental lines. The branch length units are the number of changes in the sequence divided by the sequence length in bp.

Genetic background of parental strains: The AIL population was established by crossing of a haploid laboratory line S288c with a known genome sequence, and a haploid strain isolated from nature YE-531[17]. The two haploid strains had similar mean phenotypic values (FIGS. 13A-B). We generated the genome of YE-531 by de novo sequencing. The full genomes of the two founders and 13 publicly available *S. cerevisiae* genomes of different lineages[18] were used to determine phylogenetic relationships (FIG. 9). Clearly YE-531 is distinct from the standard S288c, as well as from the sample of wild and commercial yeast strains. YE-531 is phylogenetically close to EC9-8a. This is expected, as both strains were isolated from "Evolution Canyon", Mt. Carmel, Israel[17,19].

Construction of phenotypic groups for selective DNA pooling: Selective DNA pooling (SDP) is typically implemented by selection of alternative tail groups from the overall phenotypic distribution of the mapping population. For survival, selection of the resistant tail is simply achieved by exposing the population to the selective agent (ethanol in the present case), and retaining survivors. Selection of the susceptible tail, however, is technically complex since individuals that do not survive cannot be used to produce progeny; and non-survivors may also include numerous genes affecting normal cell function. Therefore, as suggested by Lebowitz et al. (1986)[20] the entire unselected AIL F6 population was taken, (more than $3.5*10^5$ segregants/cc), to serve as the control group. Three independent aliquots, each consisting of thousands of segregants, were taken to form three unselected control pools.

To establish the resistant tail pools, a two-stage selection scheme was used. The first stage consisted of mass-selection of the AIL F6 population for survival under moderate ethanol stress. For the second stage, 300 colonies chosen at random from among the thousands of first-stage survivors were individually evaluated for growth and separately for survival under ethanol stress (FIGS. 1A-D).

Pool Genotyping: To determine marker allele frequencies in the pools, whole genome sequencing was performed followed by variant calling and LOESS smoothing. To confirm the allele frequencies obtained by deep sequencing, two of the SNPs (on chromosome 2 position 228,251, and on chromosome 4 position 949,385) in 30 random single individuals from the control and from the growth and survival tail pools were individually genotyped, using High Resolution Melting (HRM) analysis (FIGS. 10A-C). DNA of the tested strains was extracted for each individual and diluted into equal concentration of 100 ng/ml. Amplification was performed using Eco real-Time PCR system (Illumina) in 3 replicates for each strain. Amplification reaction consisted of 1 µl DNA, 0.2 µl of 10 µM of forward and reverse primers, 5 µl reaction mix (FastSYBER green master mix, Applied Biosystems), 3.6 µl ddH$_2$O. Analyses were done by Eco version 4 software. SNP frequency was calculated for each group and compared to that obtained by deep sequencing. A very high correlation (r=0.891) was found between frequency estimates from the pools and frequency estimates from individual genotyping (Table 1F).

TABLE 1F

Comparison of HRM and deep sequencing frequency estimates bp, position in bp; Pool, Source of segregants; S, S288c allele; Y, YE-531 allele; HRM, Y-allele frequency estimate obtained by HRM; DS, Y-allele frequency estimate obtained by deep sequencing.

| SNP | Chr | bp | Pool | SS | YY | SY | HRM Y allele frequency | DS[1] Y allele frequency |
|---|---|---|---|---|---|---|---|---|
| 1 | 4 | 949,385 | Growth | 11 | 7 | 12 | 0.433 | 0.430 |
|   |   |   | Population | 6 | 9 | 15 | 0.550 | 0.670 |
| 2 | 2 | 228,251 | Survival | 12 | 12 | 6 | 0.500 | 0.550 |
|   |   |   | Population | 2 | 17 | 11 | 0.750 | 0.730 |

[1]DS frequencies directly obtained after alignment to S288c reference genome, before smoothing by LOESS.

There was very wide variation in marker allele frequencies in the F6 population (Table 2, herein below). Although the F1 is expected to have allele frequency 0.5, some variation is expected in the F6 due to sampling. Surprisingly, there was very wide variation in marker allele frequencies in the F6 population. This variation is much larger than would be expected by cumulative binomial sampling. Even for effective population size of only 1000, binomial sampling would generate a frequency variance of no more than 0.02 per generation, or 0.08 across 6 generations. Thus, the remainder must have been generated by selection during the 6 AIL generations. As noted, S288c and YE-531 represent widely separated lineages (FIG. 9). Thus, considerable selection is expected as the two genomes adjust to the mutually novel genetic background generated by the cross. A further selection may be imposed by the Ether-zymolyase ascospore isolation procedure[21]. The selective forces, whatever their nature, appear to have affected alleles originating from the two parentla lines more or less equally. In the F6 general population, the major allele originated from YE-531 in 47.2% of the markers; in the remaining 52.8% of the markers, the major allele came from S288c (P<0.5 in Table 2). The small excess of S288c alleles may be due to greater adaptation of S288c to laboratory conditions. Interestingly, there were no SNPs at which the YE-531 allele was lost or fixed in F6.

TABLE 2

Distribution of YE-531 SNP allele frequencies in the F6 population.

| Frequency | N | Proportion |
|---|---|---|
| 0.0-0.1 | 292 | 0.008 |
| >0.1-0.2 | 1,408 | 0.040 |
| >0.2-0.3 | 3,726 | 0.106 |
| >0.3-0.4 | 6,375 | 0.181 |
| >0.4-0.5 | 6,753 | 0.192 |
| >0.5-0.6 | 5,894 | 0.168 |
| >0.6-0.7 | 5,527 | 0.157 |
| >0.7-0.8 | 3,968 | 0.113 |
| >0.8-0.9 | 1,134 | 0.032 |
| >0.9-1.0 | 57 | 0.002 |
| P ≤ 0.5 | 18,554 | 0.528 |
| Sum | 35,134 | 1.000 |

Figure 2B:
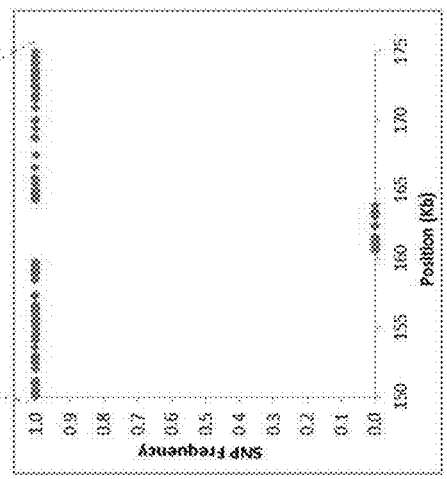

Recombination Blocks in a Random F6 Individual:

The mapping based on pool analysis revealed relatively narrow QTL that were obtained due to multiple recombinations during the 6 AIL generations. However, the mapped QTL obtained by pool analysis do not represent the distribution of the size of recombination blocks of the individual segregants formed by AIL. To evaluate the recombination block structure of an AIL individual, four random F6 haploid segregants: Line-1, Line-4, Line-8, and Line-12 were sequenced. For Line-8, the recombination block size was examined across the entire genome (FIGS. 2A-B). A total of 210 blocks were found across this individual genome, with a median length of about 16.1 Kb. More than 30% of the blocks were smaller than 5 Kb (Table 3). These results are in accord with the obtained very small QTL sizes (see below).

TABLE 3

Recombination block size distribution across the entire genome of a random F6 individual, Line-8.

| haplotype size (bp) | N | % |
|---|---|---|
| 10-100 | 3 | 1.43 |
| 100-1,000 | 22 | 10.48 |
| 1,000-5,000 | 48 | 22.86 |
| 5,000-10,000 | 20 | 9.52 |
| 10,000-100,000 | 77 | 36.67 |
| 100,000-1,000,000 | 40 | 19.05 |
| Total | 210 | |
| Median | 16.1 Kb | |

Figure 3:
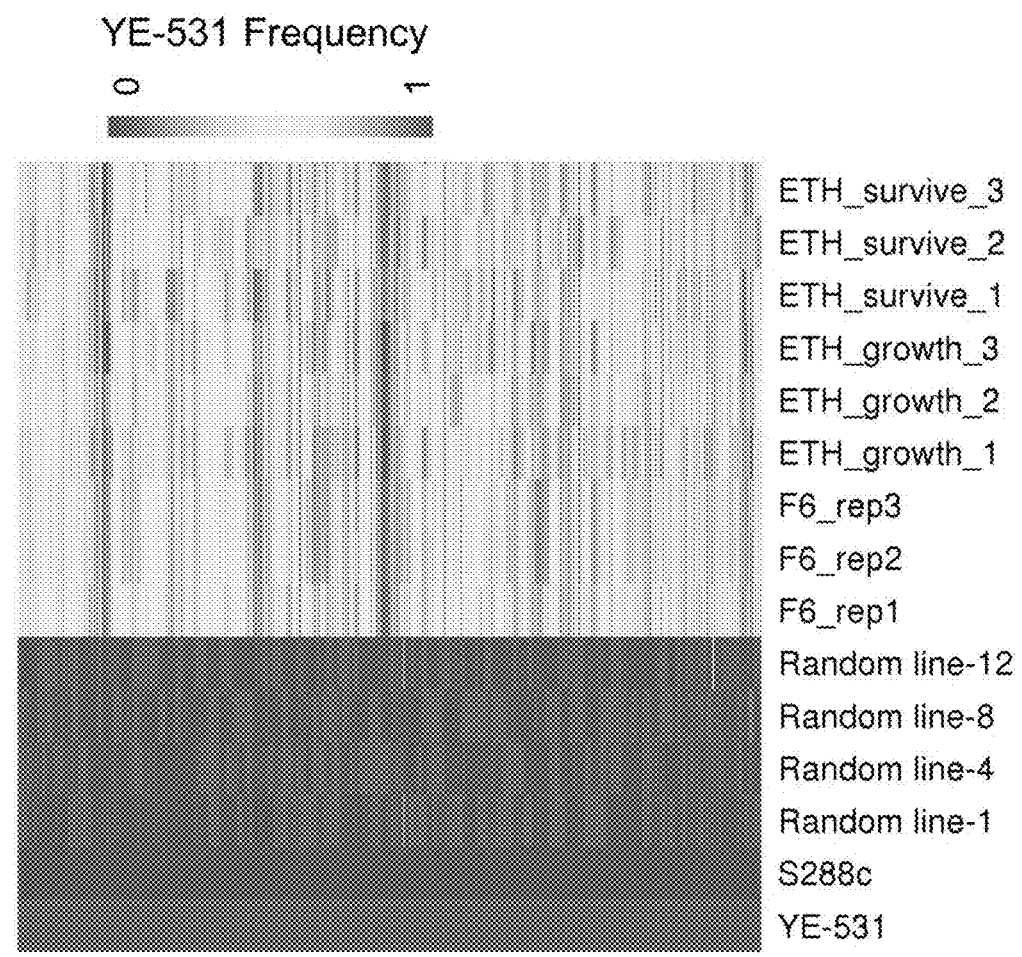
FIG. 3 is a heat map illustrating the frequency distribution of the YE-531 allele across the genome in random haploid lines and in the different pools. The heat map presents the SNP frequency values of over 35,000 informative SNPs (the top of the Y-axis is the start of the yeast genome). Frequencies of the YE-531 allele are 1 (blue) or 0 (red) in haploid lines (parental lines and F6 random lines), and more or less intermediate in the pool. The frequency stretch of alleles (0 or 1) in the random lines: 1, 4, 8 and 12, represents a haplotype block.

A heat map (FIG. 3) displays the narrow haplotype blocks of the 6-generation AIL and the resulting narrow QTLs. The frequency of the YE-531 allele across the genome is presented: for the two haploid parental lines; for the random lines: 1, 4, 8 and 12 single haploid segregants isolated from the F6; and the 9 pools: three each for survival and growth. and three for F6 population control pools. As expected, the random haploid segregants columns were a mixture of narrow blocks of either YE-531 (blue) or S288c (red) parental lines, as also shown in FIGS. 2A-B for Line-8. As expected, QTLs median size was smaller than the haplotype blocks of Line-8 (9.4 Kb and 10.3 Kb for growth-ethanol and survival-ethanol, respectively, and 16.1 Kb for Line-8). The narrow width of Line-8 blocks, confirms the efficacy of the AIL design in generating narrow haplotype blocks that increase mapping resolution. Indeed, if one zoomed in on any of these apparent blocks, one would find that it is composed of numerous sub-blocks, as seen in FIGS. 2A-B.

QTL mapping: Mapping QTLs by means of SDP was based on the difference (D-value) of YE-531 marker allele frequency between the High and control groups, after smoothing of marker frequency by LOESS[22] (FIGS. 4A-C). Note that in the given example of chromosome 11, most large Ds were negative (FIG. 4C). This indicates that the YE-531 allele is less frequent in the tail, i.e., in this case the wild YE-531 allele is associated with decreased growth and survival, while the laboratory s288c allele is associate with increased growth and survival. The same control groups were used for both traits. Comparison of alleles frequencies of the two traits and D-values between them reveals some overlaps, along with regions unique to one or the other (FIGS. 4A-C).

Allele frequencies were LOESS smoothed by chromosomal location; then SD among replicates was smoothed by allele frequency as adapted from Lipkin et al., 2016[23] Finally, variance among replicates was calculated as (smoothed-SD)$^2$. The variance estimates were 0.0010, 0.0034 and 0.0044 among within-tail replicates of the control, growth, and survival pools, respectively. As the three replicate pools in each tail consisted of 30 diploid colonies each, the number of chromosomes per tail pool was 60, and the expected variance among replicate pools would be pq/60, where p is the frequency of the YE-531 allele and q=1-p. Taking a maximum value of pq=0.25, one can expect variance among replicate pools=0.0042. In reality, for most of the SNPs pq <0.25 (Table 2). Thus, the observed values of 0.0034 for growth and 0.0044 for survival are plausible. Based on these estimates, empirical average standard errors of the differences between selected and control pools, were 0.038 and 0.042 for growth and survival, respectively. Using the D-values of individual markers after smoothing for location (Table 4), and the empirical SE, CWER P-values were obtained for each marker x trait combination.

TABLE 4

Distribution of D-values before and after LOESS

D-value was defined as the allele frequency difference between the mean of the three tail groups and the mean of the three control groups for each trait. After LOESS, 94% of D-values were in the range −0.1 to 0.1 for growth, and 86% were in this range for survival.

| | Before LOESS | | | | After LOESS | | | |
|---|---|---|---|---|---|---|---|---|
| | Growth | | Survival | | Growth | | Survival | |
| | N | % | N | % | N | % | N | % |
| >−0.4 − −0.3 | 1 | 0.00003 | 2 | 0.00006 | 0 | 0.00000 | 0 | 0.00000 |
| >−0.3 − −0.2 | 41 | 0.00114 | 48 | 0.00134 | 2 | 0.00006 | 39 | 0.00111 |
| >−0.2 − −0.1 | 1,577 | 0.04401 | 2,550 | 0.07116 | 727 | 0.02069 | 2,640 | 0.07539 |
| >−0.1 − −0.0 | 16,127 | 0.45005 | 16,030 | 0.44734 | 17,649 | 0.50233 | 14,360 | 0.41006 |
| >−0.0 − 0.1 | 17,063 | 0.47617 | 14,340 | 0.40018 | 15,481 | 0.44063 | 15,923 | 0.45470 |
| >0.1 − 0.2 | 1,001 | 0.02793 | 2,798 | 0.07808 | 1,272 | 0.03620 | 2,056 | 0.05871 |
| >0.2 − 0.3 | 14 | 0.00039 | 62 | 0.00173 | 1 | 0.00003 | 1 | 0.00003 |
| >0.3 − 0.4 | 7 | 0.00020 | 2 | 0.00006 | 1 | 0.00003 | | 0.00000 |
| >0.4 − 0.5 | 1 | 0.00003 | 1 | 0.00003 | 1 | 0.00003 | | 0.00000 |
| >0.5 − 0.6 | 1 | 0.00003 | | 0.00000 | | 0.00000 | | 0.00000 |
| >0.6 − 0.7 | 1 | 0.00003 | 1 | 0.00003 | | 0.00000 | | 0.00000 |
| ≤0 | 17,746 | 0.49523 | 18,630 | 0.51990 | 18,378 | 0.52308 | 17,039 | 0.48656 |
| >0 | 18,088 | 0.50477 | 17,204 | 0.48010 | 16,756 | 0.47692 | 17,980 | 0.51344 |
| Total | 35,834 | 1.00000 | 35,834 | 1.00000 | 35,134 | 1.00000 | 35,019 | 1.00000 |

Figure 11:
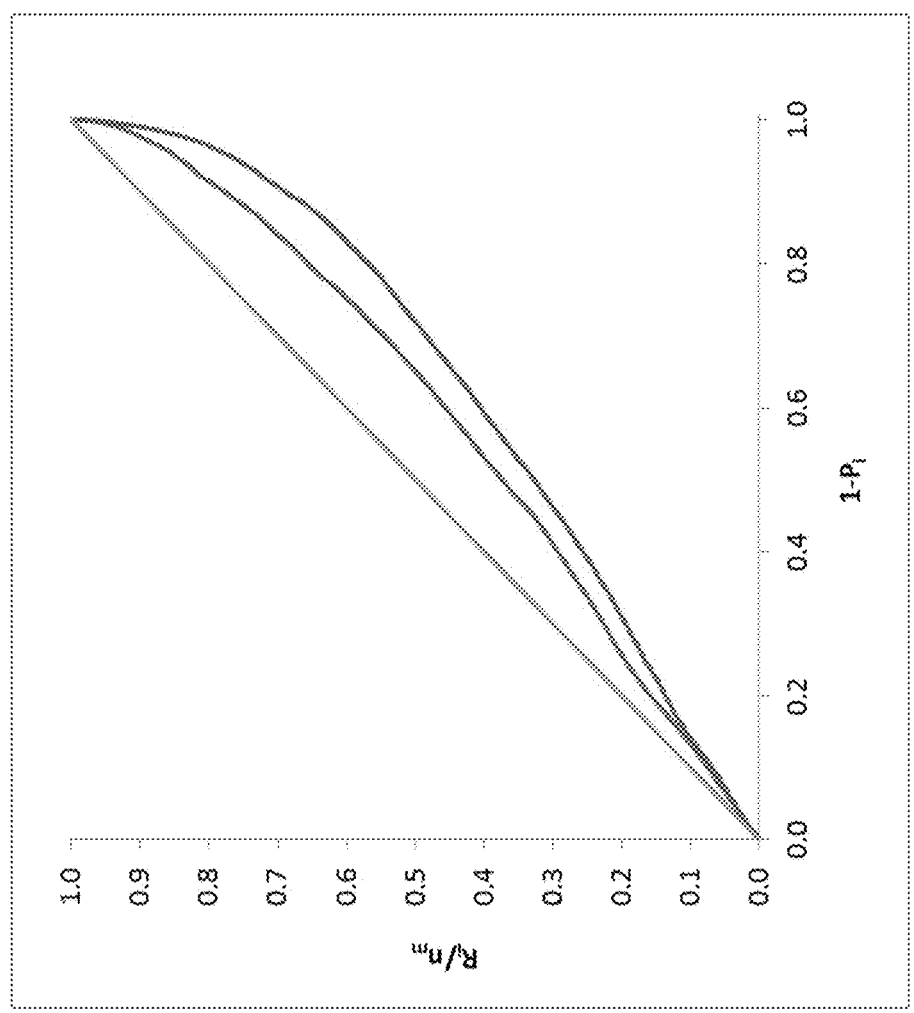
FIG. 11 is a Schweder-Spjotvoll[24] plot for P-values after LOESS smoothing. (1-$P_i$) values were sorted in ascending order. Then $R_i/n_M$, the rank number of the $i^{th}$ marker divided by the total number of marker tests ($n_M$), was plotted against the sorted (1-$P_i$) values. Green, expected 45° regression line; Blue, Growth; Red, Survival. The points corresponding to true null hypotheses should form a straight line, while those for false null hypotheses should deviate from this line. As shown in Methods, the regression lines may be used to estimate the number of true null hypotheses[23,24]. The straight diagonal line crossing the figure from 0.0 to 1.0 at 450, represents the expectation of 1-P-values against 1-P-value rank ($R_i$)/(total number of tests, $n_M$) if all marker-tests were under the null-hypothesis. The two curves below represent the actual results. The slopes of the curves are distinctly less than 450 in the first half of the chart (small 1-$P_i$=large $P_i$), reflecting a deficiency of true null-hypotheses in the dataset. On the other hand, the slopes of the curves are distinctly greater than 450 toward the right hand side of the chart (small $P_i$), reflecting a large number of rejected null-hypotheses (true, significant QTL effects). The greater concavity of the survival curve indicates a larger number of significant markers.

Table 5 shows the distribution of P-values for growth and survival. There was a large excess proportion of P-values in the lowest P-value bin (P<0.10), compared to the proportion of 0.10 expected under the null-hypothesis. This indicates the presence of a large number of rejected null hypotheses, i.e., of true marker-QTL associations. Thus, an appreciable proportion of the markers appear to be close to causative mutations affecting ethanol tolerance. This is also illustrated by the Schweder-Spjotvoll plot[24] (FIG. 11).

TABLE 5

Distribution of marker P values. N, total number of marker tests

| P | Growth | Survival |
|---|---|---|
| ≤0.1 | 0.223 | 0.310 |
| >0.1-0.2 | 0.121 | 0.122 |
| >0.2-0.3 | 0.111 | 0.084 |
| >03-0.4 | 0.089 | 0.079 |
| >0.4-0.5 | 0.082 | 0.078 |
| >0.5-0.6 | 0.081 | 0.071 |
| >0.6-0.7 | 0.067 | 0.062 |
| >0.7-0.8 | 0.068 | 0.057 |
| >0.8-0.9 | 0.084 | 0.068 |
| >0.9-1.0 | 0.074 | 0.068 |
| N | 35,134 | 35,019 |

In accord with the Schweder-Spjotvoll plot, estimates of 26,278 growth and 22,912 survival marker tests were obtained as true null hypotheses ($n_2$), leaving estimates of rejected null hypothesis ($n_1$) of 8,856 and 12,107 for growth and survival, respectively (Table 6). Thus, it is estimated that 25% (8,856/35,134) and 35% (12,107/35,019) of the markers are linked to a causative mutation affecting growth or survival under ethanol stress, respectively.

Based on these $n_2$ estimates, the power of the test[25] and the number of markers reaching significance levels according to trait for various levels of FDR are presented in Table 6. To declare significance an FDR threshold of 0.2 was chosen. Although this eliminates many markers that have high likelihood of representing true effects, it does not result in a corresponding loss of declared QTL. This is because most of the excluded markers simply represent additional markers associated with the same QTL, that reached slightly lower D-values due to sampling or distance from the causative mutation; or singleton tests that reach high significance by technical error of one sort or other.

TABLE 6

Mapping results for different significance levels after FDR correction. $n_1$, estimated number of rejected null hypothesis; $n_2$, estimated number of true null hypotheses. In calculating power, the numbers of significant markers are reduced to take FDR into account.

| FDR | Significant markers | | Power (%) | |
|---|---|---|---|---|
| | Growth | Survival | Growth | Survival |
| ≤0.001 | 37 | 19 | 0.4 | 0.2 |
| ≤0.010 | 94 | 547 | 1.1 | 4.5 |
| ≤0.050 | 383 | 1,875 | 4.1 | 14.7 |
| ≤0.100 | 1,650 | 3,700 | 16.8 | 27.5 |
| ≤0.200 | 3,043 | 7,498 | 27.5 | 49.5 |
| $n_1$ | 8,856 | 12,107 | | |
| $n_2$ | 26,278 | 22,912 | | |
| Total | 35,134 | 35,019 | | |

Declaring QTLs: A chromosomal region with SNPs having FDR≤0.2 was declared as a QTL with a 1 log-drop procedure defining boundaries as in Lipkin et. al., 2016[23] (FIGS. 5A-C). On this basis, 51 growth and 96 survival QTLs were identified (Tables 7 and 8).

TABLE 7

QTLs for growth.

QTL: serial number of QTL within trait; Chr: chromosome number;
Distance: distance between QTLs on the same chromosome; no.: number of genes;
Genes: genes acronyms; Survival QTL: shared QTL

| | | | | | | | Open Reading Frame | Survival |
|---|---|---|---|---|---|---|---|---|
| QTL | Chr | Start | End | Size | Distance | no. | Genes | QTL |
| 1 | 2 | 228,106 | 249,570 | 21,465 | | 10 | YBL002W;YBL003C;YBL004W;YBR001C;YBR002C; YBR003W;YBR004C;YBR005W;YBR006W;YBR007C; | 2 |
| 2 | 2 | 313,673 | 325,701 | 12,029 | | 7 | YBR038W;YBR039W;YBR040W;YBR041W;YBR042C; YBR043C;YBR044C | 3 |
| 3 | 2 | 344,938 | 357,199 | 12,262 | 95,369 | 7 | YBR055C;YBR056W;YBR056W-A;YBR057C;YBR058C; YBR058C-A;YBR059C; | 4 |
| 4 | 3 | 26,192 | 33,566 | 7,375 | | 3 | YCL054W;YCL055W;YCL057W; | |
| 5 | 3 | 34,008 | 41,015 | 7,008 | | 4 | YCL049C;YCL050C;YCL051W;YCL052C; | |
| 6 | 4 | 154,072 | 161,635 | 7,564 | | 2 | YDL167C;YDL171C; | |
| 7 | 4 | 1,485,812 | 1,493,260 | 7,449 | | 6 | YDR523C;YDR524C;YDR524C-B;YDR525W;YDR526C; YDR527W; | |
| 8 | 4 | 1,521,369 | 1,522,807 | 1,439 | 1,359,735 | 0 | | 21 |
| 9 | 6 | 191,655 | 192,358 | 704 | | 0 | | 30 |
| 10 | 7 | 23,509 | 66,339 | 42,831 | | 24 | YGL229C;YGL230C;YGL231C;YGL232WYGL233W;YGL234W; YGL236C;YGL237C;YGL238W;YGL239C;YGL240W;YGL241W; YGL242C;YGL243W;YGL244W;YGL245W;YGL246C;YGL247W; YGL248W;YGL249W;YGL250W;YGL251C;YGL252C;YGL253W; | 33 |
| 11 | 7 | 175,526 | 187,003 | 11,478 | | 5 | YGL169W;YGL170C;YGL171W;YGL172W;YGL173C; | |
| 12 | 7 | 906,984 | 911,599 | 4,616 | 840,646 | 4 | YGR204W;YGR205W;YGR206W;YGR207C; | 38 |
| 13 | 7 | 933,869 | 941,292 | 7,424 | 746,867 | 6 | YGR218W;YGR219W;YGR220C;YGR221C;YGR222W;YGR223C; | |
| 14 | 7 | 959,587 | 966,466 | 6,880 | 47,989 | 5 | YGR234W;YGR235C;YGR236C;YGR237C;YGR238C; | 39 |
| 15 | 7 | 970,290 | 979,683 | 9,394 | 28,999 | 6 | YGR240C;YGR240C-A;YGR241C;YGR242W;YGR243W;YGR244C; | |
| 16 | 8 | 55,265 | 63,183 | 7,919 | | 3 | YHL022C;YHL023C;YHL025W; | 41 |
| 17 | 8 | 93,752 | 93,770 | 19 | | 1 | YHL008C; | 43 |
| 18 | 8 | 96,300 | 96,393 | 94 | 33,118 | 1 | YHL007C; | 44 |

TABLE 7-continued

QTLs for growth.

QTL: serial number of QTL within trait; Chr: chromosome number;
Distance: distance between QTLs on the same chromosome; no.: number of genes;
Genes: genes acronyms; Survival QTL: shared QTL

| QTL | Chr | Start | End | Size | Distance | no. | Open Reading Frame Genes | Survival QTL |
|---|---|---|---|---|---|---|---|---|
| 19 | 8 | 143,824 | 153,195 | 9,372 | 50,055 | 6 | YHR020W;YHR021C;YHR021W-A;YHR022C;YHR022C-A; YHR023W; | 46 |
| 20 | 9 | 164,475 | 179,398 | 14,924 | | 8 | YIL099W;YIL100C-A;YIL101C;YIL103W;YIL104C;YIL105C; YIL106W;YIL107C; | 48 |
| 21 | 9 | 337,905 | 350,729 | 12,825 | | 8 | YIL002C;YIL002W-A;YIL003W;YIL004C;YIL005W;YIL006W; YIL007C;YIL009W; | |
| 22 | 10 | 392,321 | 393,564 | 1,244 | | 1 | YJL026W; | |
| 23 | 10 | 564,269 | 574,310 | 10,042 | | 10 | YJR066W;YJR067C;YJR068W;YJR069C;YJR070C;YJR071W; YJR072C;YJR073C;YJR074W;YJR075W; | |
| 24 | 10 | 726,314 | 727,128 | 815 | 332,751 | 1 | YJR154W; | 55 |
| 25 | 11 | 223,233 | 227,436 | 4,204 | | 4 | YKL112W;YKL113C;YKL114C;YKL115C; | |
| 26 | 11 | 249,846 | 256,761 | 6,916 | | 2 | YKL100C;YKL101W; | |
| 27 | 11 | 510,755 | 518,633 | 7,879 | 283,320 | 5 | YKR037C;YKR038C;YKR039W;YKR040C;YKR041W; | 59 |
| 28 | 11 | 588,930 | 589,078 | 149 | 332,170 | 1 | YKR079C; | |
| 29 | 11 | 652,034 | 658,515 | 6,482 | 133,402 | 2 | YKR103W;YKR104W; | 63 |
| 30 | 12 | 269,206 | 279,169 | 9,964 | | 6 | YLR067C;YLR068W;YLR069C;YLR070C;YLR071C;YLR072W; | |
| 31 | 13 | 220,725 | 229,786 | 9,062 | | 8 | YML021C;YML022W;YML023C;YML024W;YML025C;YML026C; YML027W;YML028W; | |
| 32 | 13 | 624,780 | 632,286 | 7,507 | | 5 | YMR182C;YMR182W-A;YMR183C;YMR184W;YMR185W; | |
| 33 | 13 | 862,890 | 874,942 | 12,053 | 633,105 | 6 | YMR297W;YMR299C;YMR300C;YMR301C;YMR302C;YMR303C; | 75 |
| 34 | 13 | 883,606 | 896,227 | 12,622 | 251,321 | 6 | YMR306C-A;YMR306W;YMR307W;YMR308C;YMR309C;YMR310C; | 76 |
| 35 | 14 | 264,232 | 275,434 | 11,203 | | 7 | YNL193W;YNL195C;YNL196C;YNL197C;YNL198C;YNL199C;YNL200C; | |
| 36 | 14 | 479,875 | 490,250 | 10,376 | | 6 | YNL073W;YNL074C;YNL075W;YNL076W;YNL077W;YNL078W; | |
| 37 | 14 | 733,411 | 736,859 | 3,449 | 457,978 | 3 | YNR057C;YNR058W;YNR059W; | |
| 38 | 14 | 749,402 | 761,395 | 11,994 | 259,153 | 5 | YNR064C;YNR065C;YNR066C;YNR067C;YNR069C; | |
| 39 | 15 | 74,576 | 90,174 | 15,599 | | 8 | YOL122C;YOL124C;YOL125W;YOL126C;YOL127W;YOL128C; YOL129W;YOL130W; | |
| 40 | 15 | 216,247 | 285,417 | 69,171 | | 30 | YOL021C;YOL023W;YOL024W;YOL026C;YOL027C;YOL028C; YOL029C;YOL030W;YOL031C;YOL032W;YOL034W;YOL036W;YOL038C-A; YOL040C;YOL041C;YOL042W;YOL043C;YOL044W;YOL045W;YOL046C; YOL047C;YOL048C;YOL049W;YOL051W;YOL052W;YOL052C;YOL053W; YOL054W;YOL056W;YOL057W;YOL058W; | |
| 41 | 15 | 681,208 | 702,970 | 21,763 | 591,035 | 8 | YOR185C;YOR186W;YOR187W;YOR188W;YOR189W;YOR190W; YOR191W;YOR192C; | |
| 42 | 15 | 821,660 | 831,051 | 9,392 | 536,244 | 4 | YOR266W;YOR267C;YOR269W;YOR270C; | |
| 43 | 15 | 846,763 | 865,788 | 19,026 | 143,794 | 10 | YOR281C;YOR283W;YOR284W;YOR285W;YOR286W;YOR287C; YOR288C;YOR290C;YOR291W;YOR292C; | |
| 44 | 16 | 80,419 | 91,627 | 11,209 | | 7 | YPL242C;YPL243W;YPL244C;YPL245W;YPL246C;YPL247C;YPL248C; | 86 |
| 45 | 16 | 95,750 | 115,252 | 19,503 | | 10 | YPL230W;YPL231W;YPL232W;YPL233W;YPL234C;YPL235W;YPL26C; YPL238C;YPL239W;YPL241C; | |
| 46 | 16 | 221,495 | 247,847 | 26,353 | 129,869 | 15 | YPL160W;YPL161C;YPL162C;YPL163C;YPL164C;YPL165C;YPL166W; YPL167C;YPL158W;YPL169C;YPL170W;YPL171C;YPL172C; YPL173W;YPL174C; | 89 |
| 47 | 16 | 304,831 | 319,901 | 15,071 | 189,580 | 9 | YPL122C;YPL123C;YPL124W;YPL125W;YPL126W;YPL127C;YPL128C; YPL129W;YPL130W; | |
| 48 | 16 | 413,248 | 422,588 | 9,341 | 165,402 | 5 | YPL070W;YPL071C;YPL072W;YPL074W;YPL075W; | |
| 49 | 16 | 876,931 | 882,103 | 5,173 | 557,031 | 3 | YPR167C;YPR168W;YPR169W; | |
| 50 | 16 | 920,832 | 933,594 | 12,763 | 498,245 | 4 | YPR192W;YPR194C;YPR195C;YPR196W; | |
| 51 | 16 | 935,125 | 942,317 | 7,193 | 53,023 | 4 | YPR198W;YPR199C;YPR200C;YPR201W; | 96 |

TABLE 8

QTLs for survival.

QTL: serial number of QTL within trait; Chr: chromosome number;
Distance: distance between QTLs on the same chromosome; no.: number of genes;
Genes: genes acronyms; Growth QTL: shared QTL

| QTL | Chr | Start | End | Size | Distance | no. | Open Reading Frame Genes | Growth QTL |
|---|---|---|---|---|---|---|---|---|
| 1 | 2 | 14,472 | 26,500 | 12,029 | | 4 | YBL101C;YBL102W;YBL104C;YBL105C; | |
| 2 | 2 | 238,080 | 239,951 | 1,872 | | 1 | YBR001C; | 1 |
| 3 | 2 | 320,188 | 331,804 | 11,617 | 293,689 | 6 | YBR041W;YBR042C;YBR043C;YBR044C;YBR045C;YBR046C; | 2 |

TABLE 8-continued

QTLs for survival.

QTL: serial number of QTL within trait; Chr: chromosome number;
Distance: distance between QTLs on the same chromosome; no.: number of genes;
Genes: genes acronyms; Growth QTL: shared QTL

| QTL | Chr | Start | End | Size | Distance | no. | Open Reading Frame Genes | Growth QTL |
|---|---|---|---|---|---|---|---|---|
| 4 | 2 | 341,973 | 371,343 | 29,371 | 102,023 | 13 | YBR054W;YBR055C;YBR056W;YBR056W-A; YBR057C;YBR058C;YBR058C-A; YBR059C;YBR060C;YBR061C;YBR062C;YBR063C;YBR065C; | 3 |
| 5 | 2 | 502,447 | 516,358 | 13,912 | 170,644 | 6 | YBR133C;YBR134W;YBR136W;YBR137W;YBR138C;YBR139W; | |
| 6 | 2 | 544,692 | 556,105 | 11,414 | 173,350 | 5 | YBR151W;YBR152W;YBR153W;YBR154C;YBR157C; | |
| 7 | 2 | 743,899 | 754,355 | 10,457 | 227,542 | 6 | YBR270C;YBR271W;YBR272C;YBR273C;YBR274W;YBR275C; | |
| 8 | 2 | 785,761 | 792,752 | 6,992 | 229,657 | 2 | YBR293W;YBR294W; | |
| 9 | 3 | 44,959 | 51,305 | 6,347 | | 7 | YCL040W;YCL041C;YCL042W;YCL043C;YCL044C;YCL045C; YCL046W; | |
| 10 | 3 | 54,441 | 64,391 | 9,951 | | 7 | YCL032W;YCL033C;YCL034W;YCL036W;YCL037C; YCL038C;YCL039W; | |
| 11 | 3 | 201,189 | 202,431 | 1,243 | 149,885 | 2 | YCR041W;YCR042C; | |
| 12 | 3 | 236,598 | 245,066 | 8,469 | 172,208 | 4 | YCR068W;YCR069W;YCR072C;YCR073C; | |
| 13 | 4 | 213,112 | 233,134 | 20,023 | | 12 | YDL128W;YDL129W;YDL130W;YDL130W-A; YDL131W;YDL132W;YDL133W;YDL134C;YDL135W;YDL136W; YDL137W;YDL138W; | |
| 14 | 4 | 239,583 | 248,311 | 8,729 | | 7 | YDL118W;YDL119C;YDL120W;YDL122W;YDL123W;YDL124W; YDL125C; | |
| 15 | 4 | 249,699 | 259,676 | 9,978 | 16,566 | 6 | YDL112W;YDL113C;YDL114W;YDL115C;YDL116W;YDL117W; | |
| 16 | 4 | 1,156,050 | 1,167,232 | 11,183 | 907,740 | 4 | YDR343C;YDR344C;YDR345C;YDR346C; | |
| 17 | 4 | 1,176,840 | 1,182,448 | 5,609 | 917,165 | 3 | YDR350C;YDR351W;YDR352W; | |
| 18 | 4 | 1,284,111 | 1,294,560 | 10,450 | 116,880 | 5 | YDR407C;YDR408C;YDR409W;YDR410C;YDR411C; | |
| 19 | 4 | 1,391,718 | 1,403,669 | 11,952 | 209,271 | 9 | YDR464W;YDR465C;YDR466W;YDR467C;YDR468C;YDR469W; YDR470C;YDR471W;YDR472W; | |
| 20 | 4 | 1,406,179 | 1,429,122 | 22,944 | 111,620 | 7 | YDR475C;YDR477W;YDR480W;YDR481C;YDR482C;YDR485C; YDR487C; | |
| 21 | 4 | 1,522,055 | 1,522,807 | 753 | 118,387 | 0 | | 8 |
| 22 | 5 | 197,724 | 211,502 | 13,779 | | 8 | YER021W;YER022W;YER023W;YER024W;YER025W;YER026C; YER027C;YER028C; | |
| 23 | 5 | 240,112 | 243,372 | 3,261 | | 2 | YER045C;YER046W; | |
| 24 | 5 | 255,344 | 273,721 | 18,378 | 43,843 | 9 | YER051W;YER052C;YER053C;YER054C;YER055C;YER056C; YER056C-A;YER058W;YER059W; | |
| 25 | 5 | 313,933 | 324,121 | 10,189 | 70,562 | 6 | YER077C;YER078C;YER078W-A;YER079W;YER080W;YER081W; | |
| 26 | 5 | 336,549 | 347,037 | 10,489 | 62,829 | 5 | YER089C;YER090W;YER091C;YER092W;YER093C; | |
| 27 | 5 | 362,788 | 374,887 | 12,100 | 38,668 | 7 | YER102W;YER103W;YER104W;YER105C;YER106W;YER107C; YER107W-A; | |
| 28 | 5 | 387,695 | 432,695 | 45,001 | 40,659 | 22 | YER112W;YER113C;YER114C;YER115C;YER116C;YER117W; YER118C;YER119C;YER119C-A;YER120W; YER121W;YER122C;YER123W;YER124C;YER125W;YER127W; YER128W;YER129W;YER130C;YER131W;YER132C;YER133W; | |
| 29 | 5 | 568,377 | 568,471 | 95 | 193,491 | 1 | YER188W; | |
| 30 | 6 | 191,392 | 192,358 | 967 | | 0 | | 9 |
| 31 | 7 | 8,977 | 16,946 | 7,970 | | 4 | YGL256W;YGL257C;YGL258W;YGL258W-A; | |
| 32 | 7 | 18,315 | 22,111 | 3,797 | | 1 | YGL255W; | |
| 33 | 7 | 51,531 | 66,126 | 14,596 | 34,586 | 9 | YGL229C;YGL230C;YGL231C;YGL232W;YGL233W;YGL234W; YGL236C;YGL237C;YGL238W; | 10 |
| 34 | 7 | 122,622 | 159,705 | 37,084 | 100,512 | 21 | YGL181W;YGL182C;YGL183C;YGL184C;YGL185C;YGL186C; YGL187C;YGL188C;YGL189C;YGL190C;YGL191W;YGL192W; YGL193C;YGL194C;YGL194C-A; YGL195W;YGL196W;YGL197W;YGL198W;YGL199C;YGL200C; | |
| 35 | 7 | 199,690 | 205,830 | 6,141 | 133,565 | 3 | YGL159W;YGL160W;YGL161C; | |
| 36 | 7 | 219,731 | 226,152 | 6,422 | 60,027 | 3 | YGL149W;YGL150C;YGL151W; | |
| 37 | 7 | 799,814 | 808,336 | 8,523 | 593,985 | 6 | YGR155W;YGR156W;YGR157W;YGR158C;YGR159C;YGR160W; | |
| 38 | 7 | 901,731 | 907,907 | 6,177 | 675,580 | 5 | YGR200C;YGR201C;YGR202C;YGR203W;YGR204W; | 12 |
| 39 | 7 | 960,867 | 968,764 | 7,898 | 152,532 | 5 | YGR234W;YGR235C;YGR236C;YGR237C;YGR238C; | 14 |
| 40 | 8 | 7,576 | 14,600 | 7,025 | | 5 | YHL044W;YHL045W;YHL046C;YHL046W-A;YHL047C; | |
| 41 | 8 | 54,496 | 64,446 | 9,951 | | 3 | YL022C;YHL023C;YHL025W; | 16 |
| 42 | 8 | 80,077 | 92,971 | 12,895 | 65,478 | 4 | YHL008C;YHL009C;YHL010C;YHL012W; | |
| 43 | 8 | 93,752 | 93,770 | 19 | 29,307 | 1 | YHL008C; | 17 |
| 44 | 8 | 96,300 | 96,685 | 386 | 3,330 | 1 | YHL007C; | 18 |
| 45 | 8 | 101,246 | 121,477 | 20,232 | 7,477 | 13 | YHL001W;YHL002C-A;YHL002W;YHL003C;YHR001W; YHR001W-A;YHR002W;YHR003C;YHR004C;YHR005C; YHR005C-A;YHR006W;YHR007C; | |
| 46 | 8 | 143,214 | 153,731 | 10,518 | 46,530 | 7 | YHR019C;YHR020W;YHR021C;YHR021W-A;YHR022C; YHR022C-A;YHR023W; | 19 |
| 47 | 9 | 26,200 | 28,067 | 1,868 | | 0 | | |
| 48 | 9 | 160,007 | 167,860 | 7,854 | | 5 | YIL105C;YIL106W;YIL107C;YIL108W;YIL109C; | 20 |
| 49 | 9 | 271,960 | 292,353 | 20,394 | 243,894 | 14 | YIL032C;YIL033C;YIL034C;YIL035C;YIL036C;YIL037C;YIL038C; YIL039W;YIL040W;YIL041W;YIL042C;YIL043C;YIL044C;YIL045W; | |
| 50 | 9 | 417,395 | 428,609 | 11,215 | 249,536 | 4 | YIR033W;YIR034C;YIR035C;YIR036C; | |

TABLE 8-continued

QTLs for survival.

QTL: serial number of QTL within trait; Chr: chromosome number;
Distance: distance between QTLs on the same chromosome; no.: number of genes;
Genes: genes acronyms; Growth QTL: shared QTL

| QTL | Chr | Start | End | Size | Distance | no. | Open Reading Frame Genes | Growth QTL |
|---|---|---|---|---|---|---|---|---|
| 51 | 10 | 39,991 | 53,880 | 13,890 | | 6 | YJL203W;YJL204C;YJL205C;YJL206C;YJL207C;YJL208C; | |
| 52 | 10 | 80,359 | 93,121 | 12,763 | | 10 | YJL176C;YJL177W;YJL178C;YJL179W;YJL180C;YJL181W;YJL183W; YJL184W;YJL185C;YJL186W; | |
| 53 | 10 | 118,772 | 134,235 | 15,464 | 64,893 | 8 | YJL154C;YJL155C;YJL156C;YJL156W-A; YJL157C;YJL158C;YJL159W;YJL160C; | |
| 54 | 10 | 649,368 | 657,109 | 7,742 | 556,248 | 3 | YJR124C;YJR125C;YJR126C; | |
| 55 | 10 | 725,020 | 727,128 | 2,109 | 590,786 | 1 | YJR154W; | 24 |
| 56 | 11 | 234,252 | 244,570 | 10,319 | | 6 | YKL104C;YKL105C;YKL106C-A;YKL106W;YKL107W;YKL108W; | |
| 57 | 11 | 401,736 | 419,256 | 17,521 | | 10 | YKL012W;YKL013C;YKL014C;YKL015W;YKL016C;YKL017C; YKL018C-A;YKL018W;YKL019W;YKL020C; | |
| 58 | 11 | 487,297 | 493,329 | 6,033 | 242,728 | 4 | YKR024C;YKR025W;YKR026C;YKR027W; | |
| 59 | 11 | 503,357 | 518,633 | 15,277 | 84,102 | 9 | YKR031C;YKR032W;YKR035C;YKR036C;YKR037C;YKR038C; YKR039W;YKR040C;YKR041W; | 27 |
| 60 | 11 | 535,712 | 545,136 | 9,425 | 42,384 | 1 | YKR054C; | |
| 61 | 11 | 553,078 | 561,071 | 7,994 | 34,446 | 6 | YKR058W;YKR059W;YKR060W;YKR061W;YKR062W;YKR063C; | |
| 62 | 11 | 565,796 | 584,447 | 18,652 | 20,661 | 13 | YKR065C;YKR066C;YKR067W;YKR068C;YKR069W;YKR070W; YKR071C;YKR072C;YKR073C;YKR074W;YKR075C;YKR076W; YKR077W; | |
| 63 | 11 | 656,736 | 658,515 | 1,780 | 95,666 | 2 | YKR103W;YKR104W; | 29 |
| 64 | 12 | 17,957 | 21,053 | 3,097 | | 1 | YLL061W; | |
| 65 | 12 | 31,899 | 62,374 | 30,476 | | 11 | YLL040C;YLL041C;YLL042C;YLL043W;YLL045C;YLL047W; YLL048C;YLL050C;YLL051C;YLL052C;YLL054C; | |
| 66 | 12 | 176,084 | 190,285 | 14,202 | 155,032 | 10 | YLR015W;YLR016C;YLR017W;YLR018C;YLR019W;YLR020C; YLR021W;YLR022C;YLR023C;YLR024C; | |
| 67 | 12 | 287,397 | 289,660 | 2,264 | 225,024 | 2 | YLR079W;YLR080W; | |
| 68 | 12 | 299,037 | 308,814 | 9,778 | 108,753 | 4 | YLR084C;YLR085C;YLR086W;YLR087C; | |
| 69 | 12 | 361,865 | 370,799 | 8,935 | 72,206 | 7 | YLR106C;YLR107W;YLR108C;YLR109W;YLR110C;YLR11W;YLR112W; | |
| 70 | 12 | 389,347 | 391,675 | 2,329 | 80,534 | 3 | YLR121C;YLR122C;YLR124W; | |
| 71 | 13 | 56,748 | 78,303 | 21,556 | | 10 | YML098W;YL099C;YML099W-A;YML100W;YML100W-A; YML102W;YML103C;YML104C;YML105C;YML106W; | |
| 72 | 13 | 562,752 | 567,163 | 4,412 | | 3 | YMR151W;YMR153W;YMR154C; | |
| 73 | 13 | 742,337 | 755,501 | 13,165 | 664,035 | 9 | YMR235C;YMR236W;YMR237W;YMR238W;YMR239C;YMR240C; YMR241W;YMR242;YMR243C; | |
| 74 | 13 | 777,456 | 832,299 | 54,844 | 210,294 | 14 | YMR257C;YMR258C;YMR259C;YMR260C;YMR261C;YMR263W; YMR265C;YMR267W;YMR273C;YMR276W;YMR277W;YMR278W; YMR279C;YMR280C; | |
| 75 | 13 | 857,214 | 879,414 | 22,201 | 101,714 | 13 | YMR294W;YMR294W-A; YMR295C;YMR296C;YMR297W;YMR299C;YMR300C;YMR301C; YMR302C;YMR303C;YMR304C-A;YMR304W;YMR305C; | 33 |
| 76 | 13 | 881,283 | 905,868 | 24,586 | 48,985 | 13 | YMR306C-A;YMR306W;YMR307W;YMR308C;YMR309C;YMR310C; YMR312W;YMR313C;YMR314W;YMR315W;YMR315W-A; YMR316C-A;YMR316W; | 34 |
| 77 | 14 | 235,815 | 236,202 | 388 | | 1 | YNL219C; | |
| 78 | 14 | 238,429 | 238,429 | 1 | | 1 | YNL218W; | |
| 79 | 14 | 243,530 | 257,114 | 13,585 | 7,329 | 7 | YNL206C;YNL207W;YNL208W;YNL209W;YNL210W;YNL215W; YNL216W; | |
| 80 | 14 | 397,996 | 404,051 | 6,056 | 159,568 | 5 | YNL118C;YNL119W;YNL120C;YNL121C;YNL122C; | |
| 81 | 14 | 602,521 | 643,259 | 40,739 | 345,408 | 11 | YNL007C;YNL008C;YNL009W;YNL010W;YNL011C;YNL012W; YNL14W;YNL016W;YNR002C;YNR007C;YNR009W; | |
| 82 | 14 | 768,862 | 777,358 | 8,497 | 364,812 | 3 | YNR070W;YNR072W;YNR073C; | |
| 83 | 15 | 710,559 | 752,970 | 42,412 | | 21 | YOR193W;YOR194C;YOR195W;YOR196C;YOR197W;YOR199W; YOR201C;YOR202W;YOR204C;YOR205C;YOR206W;YOR207C; YOR208W;YOR211C;YOR212W;YOR213C;YOR214C;YOR215C; YOR216C;YOR217W;YOR219C; | |
| 84 | 15 | 1,030,315 | 1,055,830 | 25,516 | | 8 | YOR370C;YOR371C;YOR372C;YOR373W;YOR374W;YOR378W; YOR380W;YOR381W; | |
| 85 | 16 | 40,694 | 73,474 | 32,781 | | 13 | YPL252C;YPL253C;YPL254W;YPL255W;YPL256C;YPL258C;YPL259C; YPL260W;YPL261C;YPL262W;YPL263C;YPL264C;YPL265W; | |
| 86 | 16 | 83,645 | 91,627 | 7,983 | | 6 | YPL242C;YPL243W;YPL244C;YPL245W;YPL246C;YPL247C; | 44 |
| 87 | 16 | 139,660 | 152,472 | 12,813 | 66,187 | 4 | YPL212W;YPL215W;YPL216W;YPL217C; | |
| 88 | 16 | 167,913 | 176,411 | 8,499 | 76,287 | 7 | YPL195W;YPL196W;YPL198W;YPL199C;YPL200W;YPL201C; YPL202C; | |
| 89 | 16 | 212,295 | 236,471 | 24,177 | 59,824 | 12 | YPL167C;YPL168W;YPL169C;YPL170W;YPL171C;YPL172C; YPL173W;YPL174C;YPL175W;YPL176C;YPL177C;YPL178W; | 46 |
| 90 | 16 | 256,995 | 269,012 | 12,018 | 80,585 | 5 | YPL150W;YPL151W;YPL152W;YPL153W;YPL155C; | |
| 91 | 16 | 328,197 | 337,348 | 9,152 | 91,727 | 4 | YPL113C;YPL115C;YPL116W;YPL117C; | |
| 92 | 16 | 611,302 | 620,415 | 9,114 | 342,291 | 3 | YPR024W;YPR025C;YPR026W; | |
| 93 | 16 | 722,078 | 738,527 | 16,450 | 384,731 | 9 | YPR095C;YPR096C;YPR097W;YPR098C;YPR100W;YPR101W; YPR103W;YPR104C;YPR105C; | |

TABLE 8-continued

QTLs for survival.

QTL: serial number of QTL within trait; Chr: chromosome number;
Distance: distance between QTLs on the same chromosome; no.: number of genes;
Genes: genes acronyms; Growth QTL: shared QTL

| QTL | Chr | Start | End | Size | Distance | no. | Open Reading Frame Genes | Growth QTL |
|---|---|---|---|---|---|---|---|---|
| 94 | 16 | 753,479 | 782,203 | 28,725 | 133,065 | 8 | YPR114W;YPR115W;YPR116W;YPR117W;YPR118W;YPR119W; YPR120C;YPR122W; | |
| 95 | 16 | 788,440 | 818,975 | 30,536 | 49,914 | 14 | YPR125W;YPR127W;YPR128C;YPR129W;YPR131C;YPR132W; YPR133C;YPR136C;YPR138C;YPR139C;YPR140W;YPR141C; YPR142W;YPR143W; | |
| 96 | 16 | 935,320 | 941,176 | 5,857 | 153,118 | 4 | YPR198W;YPR199C;YPR200C;YPR201W; | 51 |

Mapping resolution based on the 1 log-drop boundaries was very high, yielding QTLs smaller than commonly found. Size of the QTLs averaged 11.2 kb (0.02-69.2 kb) for growth and 12.8 kb (0.001-54.8 kb) for survival (Tables 7 and 8). The distance between QTLs on the same chromosome averaged 350.0 kb (29.0-1,359.7 kb) and 186.2 kb (3.3-917.2 kb) for growth and survival, respectively. Thus, QTLs as close as 3.3 kb were distinguished.

Three of the survival QTLs and two of the growth QTLs did not include any annotated genes. For both survival and growth, 10% of QTLs included only a single gene (10 and 5 QTLs respectively) (FIGS. 6A-C).

Twenty-one of the QTLs overlapped between the two traits as would be expected, both by chance and given the initial survival selection of the segregants.

Within the QTL boundaries 3,943 mapped SNPs and indels were identified within the growth QTL and 7,936 were identified within the survival QTL. Tables 9A-B shows overall distribution of mapped SNPs and indels among QTL, ORFs, synonymous and nonsynonymous substitutions, and regulatory sequences.

TABLE 9A

Overall distribution by traits of significant SNPs and indels among QTL, ORFs and regulatory sites. Syn, synonymous substitutions; Non-Syn, nonsynonymous substitutions. Reliable SNPs are those used for QTL definition (methods, quality control).

| | Content | Growth | Survival |
|---|---|---|---|
| QTL | SNPs | 3,592 | 7,204 |
| | Indels | 351 | 732 |
| | ORF's | 311 | 614 |
| | Regulatory sites | 81 | 145 |
| ORF | Indels | 57 | 112 |
| | Syn SNPs | 1,073 | 2,055 |
| | Non-Syn SNPs | 616 | 1,167 |
| Regulatory sites | Indels | 19 | 23 |
| | SNPs | 62 | 122 |

Functional enrichment of the QTL genes according to GO term categories: The genes contained within the boundaries of the QTL were examined for functional enrichment, using the web-based tool FunSpec (Robinson, et al. 2002). Significant enrichment was not found. This is not unexpected. The basic assumption underlying enrichment analyses is that genetic variation in a complex quantitative trait is generated by causative mutations in genes belonging to a limited number of "causative" GO categories. It can plausibly be argued, that only one ORF per QTL would belong to one of the causative GO categories; the others to unrelated categories. In total, there were 311 ORFs in the 51 QTLs for growth (mean, 6.1 ORF per QTL) and 614 ORFs in the 96 QTL for survival (6.4 ORF per QTL). Thus, any enrichment of the ORFs with respect to a GO category would be diluted 5-fold; sufficient to mask the enrichment. Limiting the field to QTL containing only a single ORF, or to QTL containing 5 or fewer ORFs, also did not yield any significant enrichment.

The field was then limited to those ORFs that included nonsynonymous mutations and indels, assuming that such mutations have higher likelihood to affect protein function and serve as causative mutations than synonymous mutations. This selection retained about two-third of the initial gene lists. For survival, significant enrichment was still not found. For growth, however, FunSpec found a significant enrichment ($P=1.3e-05$) for the MIPS category "regulation of C-compounds and carbohydrate metabolism" [number 01.05.25]. Table 9B lists the QTL genes in this category. The same selected dataset was tested using the GeneMANIA (Zuberi, et al. 2013) tool, but significant enrichment was not found.

TABLE 9B

Over-represented QTL genes found by FunSpec

| Gene | QTL |
|---|---|
| HAP2 | 10 |
| RTG2 | 10 |
| HXK2 | 10 |
| PFK1 | 15 |
| SNF6 | 16 |
| PFK26 | 20 |
| RGR1 | 30 |
| MKS1 | 36 |
| GCR2 | 35 |
| GAL11 | 40 |
| SNF2 | 43 |
| GCR1 | 48 |
| TAF14 | 47 |
| BEM4 | 46 |
| GAL4 | 44 |

Figure 14A:
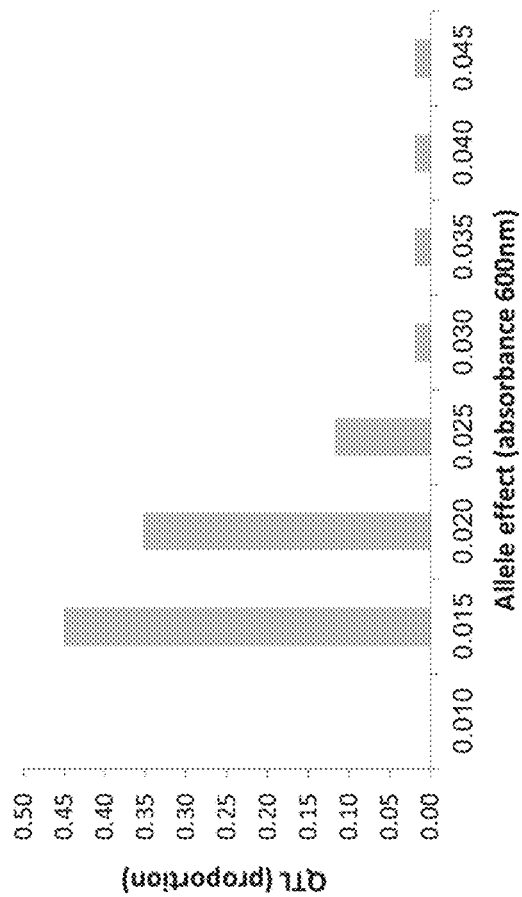
FIGS. 14A-B: Distribution of QTL allele effects for survival and growth. The average effects for the 3 top markers in each QTL are given. The distributions differ in detail, but both show complete absence of QTL of large effect, very low frequency of QTL of moderate effects, and a very large number of QTL of small effect. Thus, distributions differ from the infinitesimal model, in that the almost all variation is in QTL of small, but mappable effect; but also differ from typical QTL model in the complete absence of QTL of large effect, and paucity of QTL of moderate effect (A) Survival. (B) Growth.
Figure 14B:
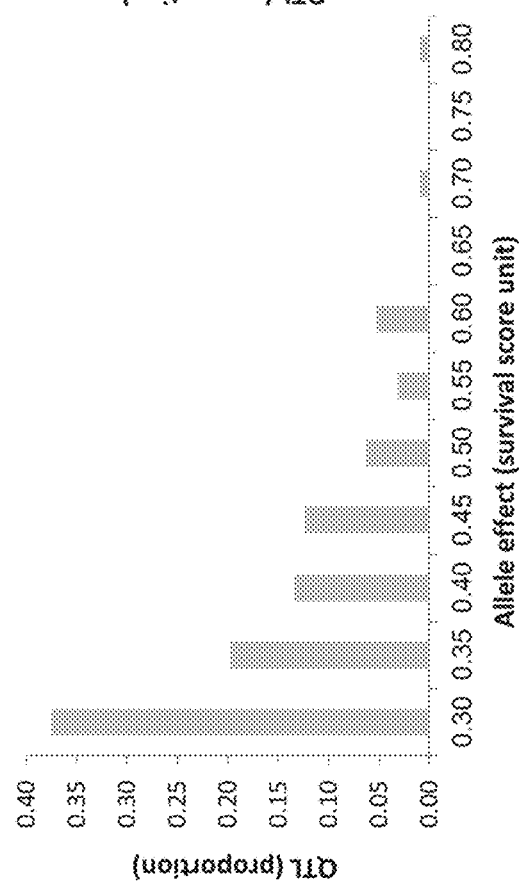

Many QTLs of small effect contribute to phenotypic variation: Allele effects averaged 0.018 (0.012-0.044) absorbance 600 nm for growth and 0.357 (0.207-0.794) survival score for survival (Tables 10A and 10B, herein below). FIG. 14A-B shows the distribution of QTL-effects for growth and survival. For both traits, the distribution is rather atypical for quantitative trait, namely: complete absence of QTLs of large effect (i.e., QTL individually explaining >5% of phenotypic variance); very small number of QTLs of moderate effect (i.e., QTL individually explaining 2% to 5% of phenotypic variance; and the remainder made up of QTLs of small effect (individually explaining <2% of phenotypic variance). Mean and range of contribution of individual QTL to the phenotypic variance were essentially the same for the two traits, namely, 0.7% (0.3-3.1%) for growth and 0.7% (0.3-3.3%) for survival. The total QTL-contribution to the phenotypic variance was, 34.7% and 72.0% for growth and survival, respectively. The total QTL-contribution to the genetic variance may be considerably greater. If, for example, heritability of the traits is 0.5, then the mapped QTLs would account for (34.7/50.0=) 69% of genetic variation for growth, and essentially all genetic variation for survival.

TABLE 10A

QTL allele effect (δ) and contribution to the phenotypic variance (cP) Growth (OD units at 600 nm)

| Chr | QTL | δ | cP | Chr | QTL | δ | cP | Chr | QTL | δ | cP |
|---|---|---|---|---|---|---|---|---|---|---|---|
| 2 | 1 | 0.034 | 0.020 | 8 | 18 | 0.044 | 0.031 | 14 | 35 | 0.019 | 0.006 |
| 2 | 2 | 0.021 | 0.007 | 8 | 19 | 0.015 | 0.005 | 14 | 36 | 0.019 | 0.003 |
| 2 | 3 | 0.021 | 0.005 | 9 | 20 | 0.015 | 0.005 | 14 | 37 | 0.013 | 0.003 |
| 3 | 4 | 0.012 | 0.003 | 9 | 21 | 0.012 | 0.003 | 14 | 38 | 0.022 | 0.009 |
| 3 | 5 | 0.014 | 0.004 | 10 | 22 | 0.018 | 0.006 | 15 | 39 | 0.017 | 0.007 |
| 4 | 6 | 0.013 | 0.004 | 10 | 23 | 0.021 | 0.007 | 15 | 40 | 0.015 | 0.004 |
| 4 | 7 | 0.015 | 0.004 | 10 | 24 | 0.014 | 0.003 | 15 | 41 | 0.013 | 0.004 |
| 4 | 8 | 0.021 | 0.008 | 11 | 25 | 0.020 | 0.009 | 15 | 42 | 0.014 | 0.004 |
| 6 | 9 | 0.027 | 0.016 | 11 | 26 | 0.017 | 0.006 | 15 | 43 | 0.019 | 0.007 |
| 7 | 10 | 0.015 | 0.005 | 11 | 27 | 0.015 | 0.004 | 16 | 44 | 0.019 | 0.008 |
| 7 | 11 | 0.025 | 0.010 | 11 | 28 | 0.020 | 0.008 | 16 | 45 | 0.015 | 0.005 |
| 7 | 12 | 0.017 | 0.005 | 11 | 29 | 0.019 | 0.008 | 16 | 46 | 0.013 | 0.004 |
| 7 | 13 | 0.014 | 0.004 | 12 | 30 | 0.014 | 0.003 | 16 | 47 | 0.012 | 0.003 |
| 7 | 14 | 0.019 | 0.008 | 13 | 31 | 0.020 | 0.009 | 16 | 48 | 0.013 | 0.004 |
| 7 | 15 | 0.015 | 0.005 | 13 | 32 | 0.017 | 0.006 | 16 | 49 | 0.016 | 0.004 |
| 8 | 16 | 0.019 | 0.007 | 13 | 33 | 0.016 | 0.005 | 16 | 50 | 0.013 | 0.003 |
| 8 | 17 | 0.037 | 0.025 | 13 | 34 | 0.020 | 0.009 | 16 | 51 | 0.014 | 0.004 |
| | | | | | | | | | Avg | 0.018 | 0.007 |
| | | | | | | | | | Total | | 0.347 |

TABLE 10B

QTL allele effect (δ) and contribution to the phenotypic variance (cP) Survival (survival trait units)

| Chr | QTL | δ | cP | Chr | QTL | δ | cP | Chr | QTL | δ | cP |
|---|---|---|---|---|---|---|---|---|---|---|---|
| 2 | 1 | 0.244 | 0.003 | 7 | 33 | 0.334 | 0.006 | 12 | 65 | 0.309 | 0.006 |
| 2 | 2 | 0.584 | 0.017 | 7 | 34 | 0.561 | 0.010 | 12 | 66 | 0.251 | 0.004 |
| 2 | 3 | 0.480 | 0.006 | 7 | 35 | 0.279 | 0.005 | 12 | 67 | 0.479 | 0.009 |
| 2 | 4 | 0.436 | 0.006 | 7 | 36 | 0.337 | 0.007 | 12 | 68 | 0.353 | 0.006 |
| 2 | 5 | 0.460 | 0.009 | 7 | 37 | 0.269 | 0.005 | 12 | 69 | 0.328 | 0.005 |
| 2 | 6 | 0.489 | 0.010 | 7 | 38 | 0.320 | 0.006 | 12 | 70 | 0.373 | 0.006 |
| 2 | 7 | 0.405 | 0.007 | 7 | 39 | 0.286 | 0.005 | 13 | 71 | 0.287 | 0.005 |
| 2 | 8 | 0.550 | 0.012 | 8 | 40 | 0.423 | 0.011 | 13 | 72 | 0.415 | 0.010 |
| 3 | 9 | 0.337 | 0.006 | 8 | 41 | 0.452 | 0.013 | 13 | 73 | 0.258 | 0.004 |
| 3 | 10 | 0.335 | 0.005 | 8 | 42 | 0.296 | 0.006 | 13 | 74 | 0.254 | 0.004 |
| 3 | 11 | 0.377 | 0.009 | 8 | 43 | 0.794 | 0.033 | 13 | 75 | 0.413 | 0.009 |
| 3 | 12 | 0.455 | 0.012 | 8 | 44 | 0.376 | 0.007 | 13 | 76 | 0.253 | 0.004 |
| 4 | 13 | 0.284 | 0.005 | 8 | 45 | 0.240 | 0.004 | 14 | 77 | 0.576 | 0.006 |
| 4 | 14 | 0.231 | 0.003 | 8 | 46 | 0.246 | 0.004 | 14 | 78 | 0.693 | 0.013 |
| 4 | 15 | 0.316 | 0.006 | 9 | 47 | 0.249 | 0.004 | 14 | 79 | 0.265 | 0.004 |
| 4 | 16 | 0.364 | 0.009 | 9 | 48 | 0.234 | 0.003 | 14 | 80 | 0.250 | 0.004 |
| 4 | 17 | 0.274 | 0.005 | 9 | 49 | 0.303 | 0.006 | 14 | 81 | 0.313 | 0.006 |
| 4 | 18 | 0.294 | 0.005 | 9 | 50 | 0.412 | 0.011 | 14 | 82 | 0.207 | 0.003 |
| 4 | 19 | 0.294 | 0.005 | 10 | 51 | 0.415 | 0.011 | 15 | 83 | 0.308 | 0.005 |
| 4 | 20 | 0.274 | 0.004 | 10 | 52 | 0.247 | 0.004 | 15 | 84 | 0.311 | 0.006 |
| 4 | 21 | 0.550 | 0.017 | 10 | 53 | 0.297 | 0.006 | 16 | 85 | 0.277 | 0.005 |
| 5 | 22 | 0.301 | 0.005 | 10 | 54 | 0.309 | 0.006 | 16 | 86 | 0.403 | 0.010 |
| 5 | 23 | 0.358 | 0.008 | 10 | 55 | 0.418 | 0.008 | 16 | 87 | 0.388 | 0.010 |
| 5 | 24 | 0.347 | 0.008 | 11 | 56 | 0.341 | 0.008 | 16 | 88 | 0.336 | 0.005 |
| 5 | 25 | 0.372 | 0.009 | 11 | 57 | 0.391 | 0.010 | 16 | 89 | 0.301 | 0.006 |
| 5 | 26 | 0.281 | 0.005 | 11 | 58 | 0.299 | 0.005 | 16 | 90 | 0.426 | 0.012 |

TABLE 10B-continued

QTL allele effect (δ) and contribution to the phenotypic variance (cP) Survival (survival trait units)

| Chr | QTL | δ | cP | Chr | QTL | δ | cP | Chr | QTL | δ | cP |
|---|---|---|---|---|---|---|---|---|---|---|---|
| 5 | 27 | 0.281 | 0.005 | 11 | 59 | 0.387 | 0.008 | 16 | 91 | 0.356 | 0.008 |
| 5 | 28 | 0.285 | 0.005 | 11 | 60 | 0.258 | 0.004 | 16 | 92 | 0.303 | 0.006 |
| 5 | 29 | 0.351 | 0.007 | 11 | 61 | 0.260 | 0.004 | 16 | 93 | 0.424 | 0.011 |
| 6 | 30 | 0.564 | 0.020 | 11 | 62 | 0.394 | 0.010 | 16 | 94 | 0.267 | 0.005 |
| 7 | 31 | 0.264 | 0.004 | 11 | 63 | 0.525 | 0.018 | 16 | 95 | 0.551 | 0.018 |
| 7 | 32 | 0.274 | 0.005 | 12 | 64 | 0.441 | 0.011 | 16 | 96 | 0.266 | 0.004 |
|     |     |       |       |     |     |       |       | Avg |     | 0.357 | 0.008 |
|     |     |       |       |     |     |       |       | Total |   |       | 0.720 |

δ, allele effect; cP, the contribution of the QTL to the phenotypic variance.

RHA strongly supports the mapping results: For validation, the present inventors investigated a few of the most likely candidate genes (mapped down to a single gene or due to their biological function) that were also located in genomic sites enabling simple gene manipulation. Based on mapping, it was hypothesized that a candidate mutation generating a phenotypic difference between a tail and F6 control (i.e., on F6 genetic background) should also cause a difference in the same direction, between the two alleles in an F1 background on an RHA test.

Figure 15B:
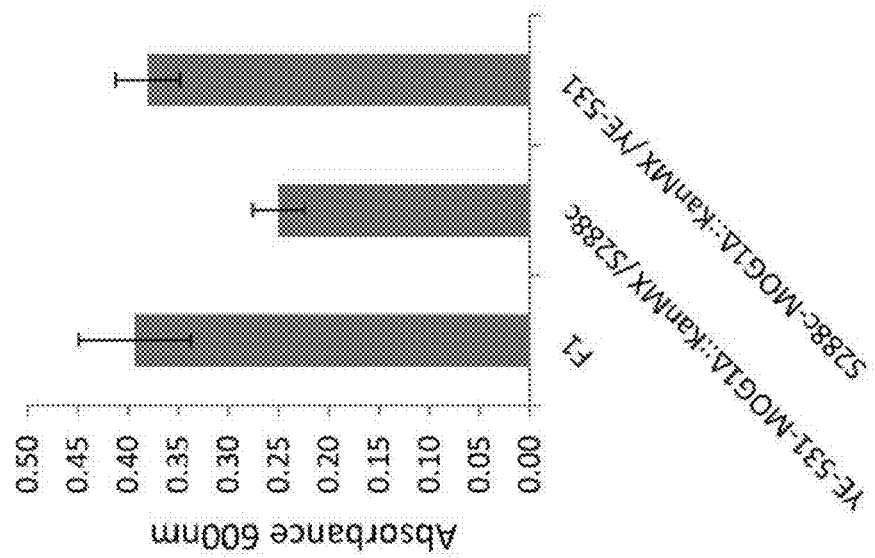
FIGS. 15A-B: Reciprocal hemizygosity analysis confirms the contribution of ADH2 and MOG1 to ethanol tolerance trait. Growth ability tests under ethanol stress (left, 10%; right, 11%) of F1 and ADH2/MOG1 reciprocal hemizygous deletions. The mean values of 4 repeats in a single batch and the SD are presented. See tests for statistical significance, based on two batches, in Table 1E. (A) ADH2 gene contributes to ethanol tolerance trait. The effect was small, as might be expected for effect of a single gene only, but in the correct direction and statistically significant (Table 1E). (B) MOG1 gene contributes to ethanol tolerance trait. F1 hybrids were individually deleted for the ADH2 and MOG1 alleles. In both cases, the deletion of S288c-alleles in the background of the F strain resulted in a better growth ability than of the deletion of YE-531-alleles (YE-531-allele increase ethanol tolerance).
Figure 15A:
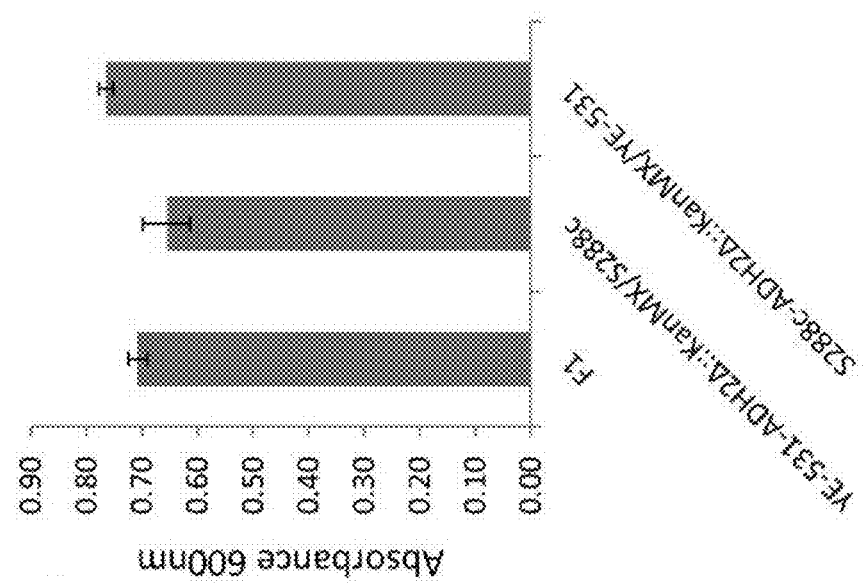
Figure 16:
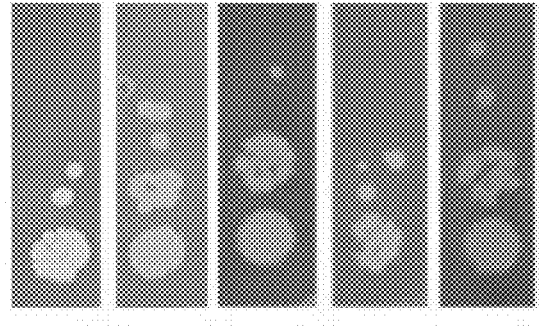
FIG. 16: Reciprocal hemizygosity analysis confirms the contribution of YJR154W and MGS1 to ethanol survival trait. Survival ability tests of reciprocal hemizygous deletions, was tested under ethanol stress (19% (V/V)). In the background of the F1 strain, the deletion of YE-531-allele (and expression of the S288c allele) resulted in a better survival ability than of the deletion of S288c allele for MGS1 (and expression of the YE-531 allele). Thus, YE-531-allele increased ethanol tolerance. The opposite was obtained for YJR154W, as in this case YE-531-allele increased ethanol tolerance.

Four of the ten gene x trait combinations, differed significantly in the RHA (FIGS. 15A-B-16, Table 1E). Of the six remaining RHA, one (NTH2×survival) gave exactly equal results, while five differed in the expected direction, but did not reach statistical significance.

All 9 differing RHA comparisons had the same direction as the QTL mapping (Table 1E). Thus, applying a sign test the null hypothesis that the favorable alleles identified by QTL mapping and the favorable alleles identified by RHA are independent is falsified at p<0.0002. Hence, at least some, and most likely all of the RHA comparisons which did not reach significance can be taken to represent Type II errors, so that overall support of the QTL results by the RHA is very strong.

The effect of ADH2 was validated by RHA for growth, while the positive allele was contributed from YE-531 (Table 1E). Since ADH2 is an alcohol dehydrogenase which oxidizes ethanol to acetaldehyde (de Smidt, et al. 2012), the identified positive allele is expected to reduce ethanol production. Indeed, there was greater ethanol production in the YE-531-allele's deletion strain in the F1 background, relative to its reciprocal deletion in the F1 (FIG. 17). By knocking out both copies of the ADH2 allele, ethanol production was greater than in the F1 and reciprocal deletions. Importantly, initial glucose levels were equal for all samples (6.68% (w/v)). At the end (after 17 hours of incubation), for all samples glucose was not completely utilized, so that glucose levels were not a limiting factor.

CONCLUSION

In the present study a low-cost quantum leap in the number and map resolution of QTL identified in a single experiment was achieved by combining a number of advanced design, molecular, and statistical procedures in HRMT. This cost effective tool-kit can be applied with any sexual model organism. The used HRMT includes AIL design to increase mapping resolution (applied here for the first time for mapping QTL affecting ethanol tolerance); Ether-zymolyase (EZ) ascospore isolation procedure[21] to increase by orders of magnitude the number of segregants obtained in a yeast cross; two-stage individual phenotyping to increase trait heritability; selective DNA pooling s with genotyping by sequencing so that all causative mutations are included in the analyzed markers; use of DNA pools to enable low cost "genotyping by deep sequencing" of many individuals; LOESS smoothing of allele frequencies to reduce error variation; Log Drop analysis to define QTL boundaries.

Application of these procedures to ethanol tolerance in yeast provided high resolution QTL mapping, often to the level of the individual gene; more than twice the number of QTL affecting a single trait of any QTL mapping experiment in yeast; an order of magnitude increase in the number of QTL affecting ethanol tolerance of any single previous QTL mapping experiment for this trait (145 versus up to 19) (Swinnen, et al. 2012) (Ehrenreich, et al. 2010), (Hu, et al. 2007), (Snoek, et al. 2016) (Pais, et al. 2013); Taken together these procedures place yeast as a model organism par excellence for genetic analysis of complex traits in general, and ethanol tolerance in particular.

The AIL experimental design was carried out by intercrossing an F1 created by crossing a common laboratory line (S288c) and a line isolated from nature (YE-531). Phylogenetic analysis confirmed that these two lines are widely separated.

Multiple recombination events across six AIL generations, resulted in a fine-grained mosaic genome. EZ technology[21] overcame the technical challenge of producing large numbers of segregants in a yeast cross, providing more than $10^5$ segregants in each of the AIL generations. Large population size minimized sampling effects on the distribution of recombination points across generations[13], and increased statistical power to detect QTL with relatively small effects.

In contrast to previous studies using AIL[15,16] that phenotyped the mapping population by simply applying a stressor and selecting the survivors, in the present study a more accurate two-stage phenotyping procedure was used to evaluate ethanol tolerance. In the first stage, a sample of 300 candidate colonies that survived under moderate ethanol stress were selected at random out of much larger number of survivors ($>10^5$), to preserve genetic variation while providing moderate selection for ethanol tolerance. In the second stage, the 300 candidate colonies were individually phenotyped for growth and for survival under ethanol stress. Individual phenotyping, as opposed to previous studies that mostly did only bulk phenotypic evaluation, allowed more precise selection of colonies to create the phenotypic tails and increase mapping accuracy. It should be noted however, that increased accuracy by individual phenotyping was at the expense of some reduction in selection intensity, and did not make full use of the very large number of segregants that were available.

For each of the two traits separately, the most tolerant 90 among the 300 candidates for growth and the most tolerant 90 among the 300 for survival were chosen for mapping QTL under ethanol stress. The use of pools allowed genotyping by deep sequencing of considerably more individuals than would have been feasible by individual whole genome sequencing, thus increasing the statistical power by increasing sample size. Taking this into account, it can be concluded that any loss in power due to pooling instead of individual sequencing is more than offset by the exceptionally high coverage obtained (on order of ~1000× for all pools).

A novel combination of two statistical methods was efficiently used for high resolution QTL mapping. Local smoothing as implemented by LOESS was applied here for the first time in QTL mapping for accurate estimation of the frequency and variance of each SNP. Following Lipkin et al. (PLOS ONE, 2016), a Log drop algorithm was applied to define boundaries of QTLs.

Figure 7B:
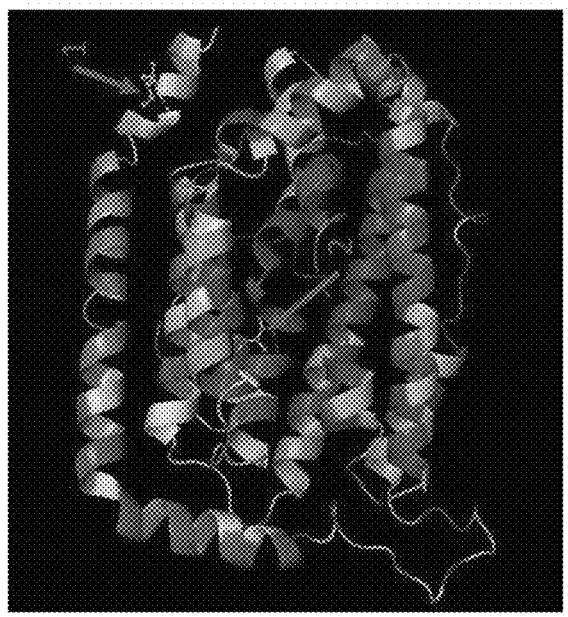
FIGS. 7A-B: Examples of strong candidate mutations located in a QTL, presented in three-dimensional (3D) protein structures. Color scale represents amino acid conservation scores as defined by ConSurf software (Ashkenazy, et al. 2010; Celniker, et al. 2013): (Blue—conserved, Red—variable). (A) A candidate causative mutation in MMP1 mapped to survival QTL 63. The mutation site at the red arrow (chr 12: 18,377; supplementary dataset S2), is located in an alpha helix conserved region. The substitution of GCC for GTC caused an alteration of Alanine to Valine. A destabilizing effect of this mutation on the protein, was predicted by DUET in 5 predicted models (Pires, et al. 2014). (B) Two candidate causative mutations in RNR2 (PDB: 1SMQ), mapped to growth QTL 22. The mutation site at red arrow 1 (chr10: 392,498; supplementary dataset S2) is located on the protein surface in a non-conserved region. The substitution of ACA for AAA caused an alteration of Threonine to Lysine. This mutation has high probability of affecting protein-protein interaction, as predicted by ODA (Fernandez-Recio, et al. 2005). The mutation at red arrow 2 (chr10: 393,112; supplementary dataset S2) is located in a highly conserved region. The substitution of TCC for GCC caused an alteration of Serine to Alanine. A destabilizing effect of this mutation on the protein was predicted by DUET (Pires, et al. 2014).
Figure 7A:
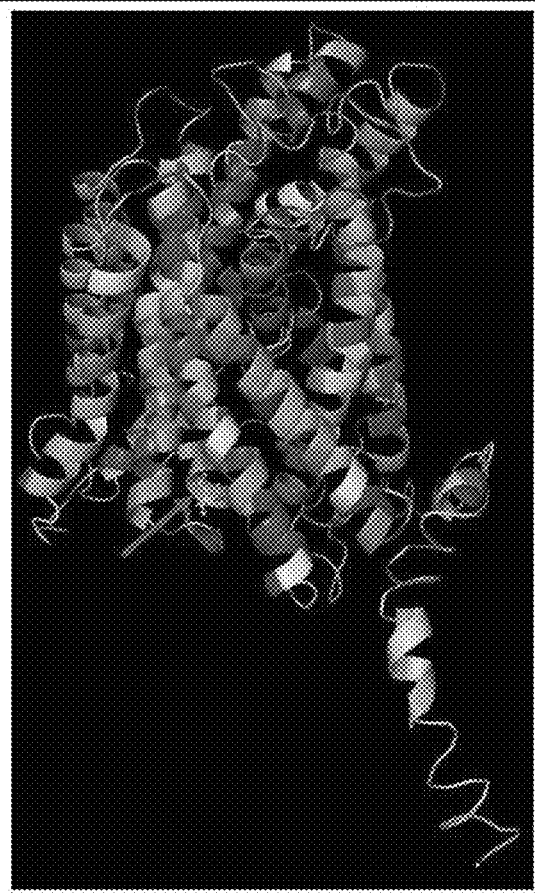
Figure 8:
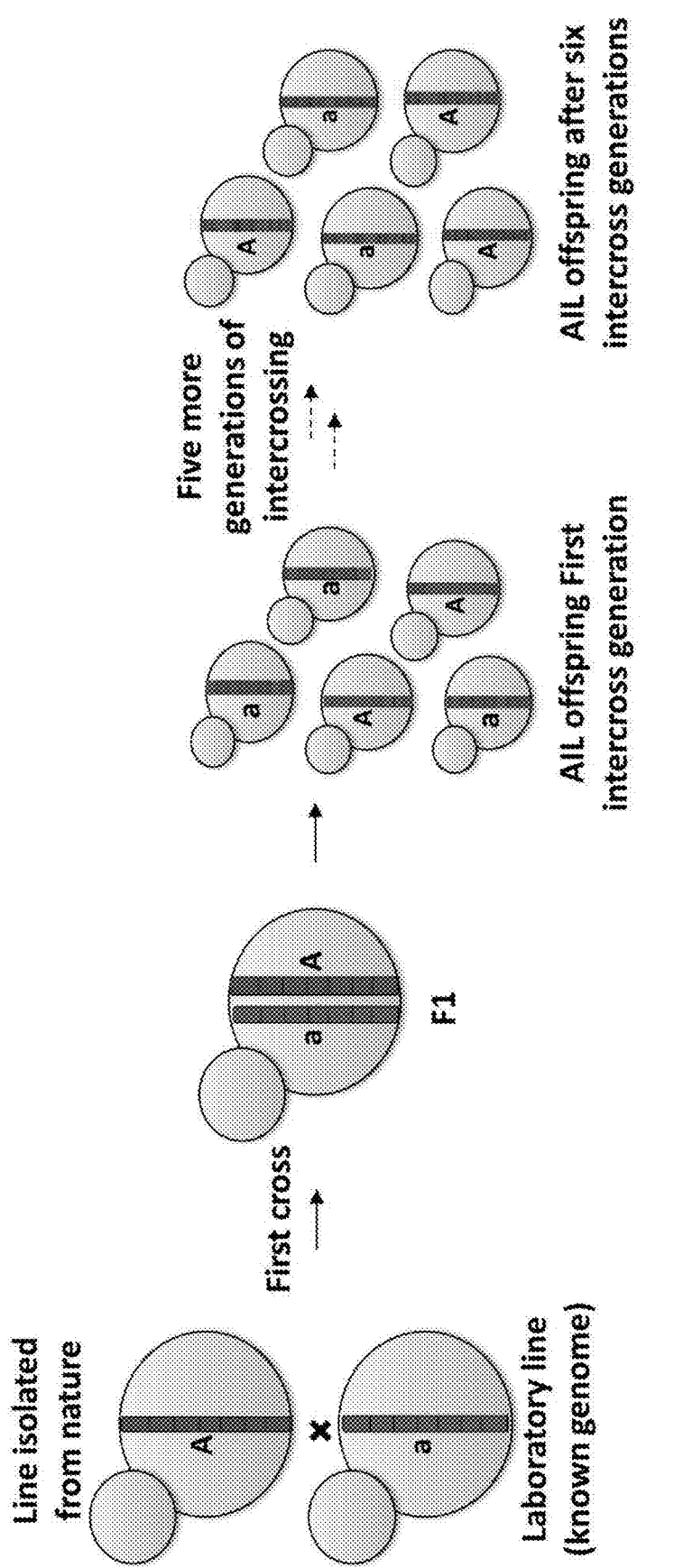
FIG. 8 illustrates the AIL scheme for fine mapping. A haploid strain isolated from nature (YE-531)[17] and a laboratory haploid strain ($S228_c$) were crossed to create an F1. The F1 went through sporulation followed by germination and intercrosses for 5 more generations, creating a mosaic genome. A/a, QTL alleles[13].

Some of the QTLs include mutations that are likely to have a direct phenotypic effect. Such mutations are those that involve early stop codons, mutations in conserved regions, frameshift mutations and more (Tables 11-12). Indeed, in the growth and survival QTLs, 2 and 10 mutations respectively involved substitution of an amino acid by an early stop codon while in 4 and 11 mutations, respectively, a stop codon was changed to an amino acid (in respect to the sequence of S288c). Several mapped mutations were predicted to have a strong effect on protein structure and function of two genes (MMP1 and RNR2) mapped to a level of a single gene (FIGS. 7A-B). For MMP1, a S-methylmethionine permease (membrane transport protein) (Rouillon, et al. 1999), a non-silent mutation substitution in MMP1, located in an alpha helix-conserved region was predicted to reduce the stability of the protein. Since membrane function and structure interference under ethanol stress is well known, the predicted effect of MMP1 on ethanol tolerance is not surprising (Sikkema, et al. 1995). RNR2, the second investigated gene is a ribonucleotide reductase which is regulated by DNA replication and DNA damage checkpoint pathways (Elledge and Davis 1987). For RNR2, two non-silent mutations were mapped; one located on the surface of the protein in a site predicted to affect protein-protein interactions, the other located in a highly conserved region and predicted to reduce the stability of the protein.

The contribution of the gene, ADH2 mapped in this study, was successfully confirmed by RHA. The positive allele in this case contributed from YE-531 (Table 1E; FIG. 15A. However, since ADH2 is an alcohol dehydrogenase whose primary function is to oxidize ethanol to acetaldehyde (de Smidt, et al. 2012), the same allele is expected to reduce ethanol production. The present inventors validated that expectation, showing increased production of ethanol by the YE-531-allele deletion strain in the F1 background, relative to its reciprocal deletion and the F1 (FIG. 17). Also, by knockout of both copies of ADH2 alleles in the F1 background gave highest ethanol production relative to the other tested lines, as also shown by previous studies (Ida, et al. 2012; Ye, et al. 2016).

Four of the ten gene x trait combinations tested, differed significantly in the RHA analyses (FIGS. 15A-B-16), and five other gene x trait combinations differed in the correct direction, but did not reach statistical significance (Table 1E). These results strongly support the mapping results.

Several mapped genes participate in known stress response and protection mechanisms, under ethanol stress. The genes FAS2, FAT1, and FAA3 participate in fatty acid synthesis and transport pathways, which are part of adaptation mechanisms that protect the cell against ethanol toxicity (Sikkema, et al. 1995). Adaptive cross protection mechanisms also include changes in HSP expression. Accordingly, the present inventors mapped for survival the binding site of HSF1 product, a trimeric heat shock transcription factor (Bonner, et al. 1992); SSA4, which is a HSP that was upregulated upon ethanol stress (Quan, et al. 2004). One more general stress response system is STRE, promoter elements which mediate transcription and leads to a tolerant state towards any stress condition (Estruch 2000). Therefore, not surprisingly MSN2 was mapped for both traits and MSN4 was mapped for growth, both bind DNA at STRE of responsive genes.

The mapped genes: ADH2, MOG1, MGS1 and YJR154W, were significantly validated by RHA. ADH2 is an alcohol dehydrogenase whose primary function is to oxidize ethanol to acetaldehyde (de Smidt, et al. 2012). MOG1 is involved in nuclear transport mechanism (Oki and Nishimoto 1998), known to protect the cell from stress induced damage (Saavedra, et al. 1996; Takemura, et al. 2004). MGS1 is related to DNA replication stress (Tkach, et al. 2012). YJR154W is uncharacterized. The HRMT allowed mapping of many dozens QTLs of small effect, while only a very few QTLs of moderate to large effect were found. The somewhat lesser statistical power of other studies (Swinnen, et al. 2012) (Ehrenreich, et al. 2010), (Hu, et al. 2007), (Snoek, et al. 2016) (Cubillos, et al. 2011) would have limited them to the few QTLs of moderate to large effect, with the great bulk of QTLs of small effect out of reach. Some part of the "Missing Heritability" conundrum (Manolio, et al. 2009) may be attributed to these minor QTLs, which are only identified in experiments with high statistical power.

Tables 11 and 12 show the various positions of sequences identified using the presently disclosed methods for identifying loci associated with growth and survival respectively. The columns are:

Chr—The chromosome which the mutation located in as shown

Pos: The position of the mutation in the chromosome (bp)

QTL: The QTL serial number

Feature: The type of genetic element which the mutation represents

Ref. Allele: Allele of the reference genome

Alter. Allele: Allele of YE-531

Original codon: Reference genome

New codon: New SNP (only for SNP located inside a ORF)

Original AA: Reference genome

Syn. substitution: Synonymous substitution

Non-syn. substitution: Non-synonymous substitution

---

Lengthy table referenced here

US11692166-20230704-T00001

Please refer to the end of the specification for access instructions.

Lengthy table referenced here

US11692166-20230704-T00002

Please refer to the end of the specification for access instructions.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Amorim, H. V., Lopes, M. L., de Castro Oliveira, J. V., Buckeridge, M. S. & Goldman, G. H. Scientific challenges of bioethanol production in Brazil. *Appl Microbiol Biotechnol* 91, 1267-75 (2011).
2. Hu, X. H. et al. Genetic dissection of ethanol tolerance in the budding yeast *Saccharomyces cerevisiae*. *Genetics* 175, 1479-87 (2007).
3. Swinnen, S., Thevelein, J. M. & Nevoigt, E. Genetic mapping of quantitative phenotypic traits in *Saccharomyces cerevisiae*. *FEMS Yeast Res* 12, 215-27 (2012).
4. Liti, G. & Louis, E J. Advances in quantitative trait analysis in yeast. *PLoS Genet* 8, e1002912 (2012).
5. Darvasi, A. & Soller, M. Selective DNA pooling for determination of linkage between a molecular marker and a quantitative trait locus. *Genetics* 138, 1365-73 (1994).
6. Ehrenreich, I. M. et al. Dissection of genetically complex traits with extremely large pools of yeast segregants. *Nature* 464, 1039-42 (2010).
7. Korol, A., Frenkel, Z., Cohen, L., Lipkin, E. & Soller, M. Fractioned DNA pooling: a new cost-effective strategy for fine mapping of quantitative trait loci. *Genetics* 176, 2611-23 (2007).
8. Duitama, J. et al. Improved linkage analysis of Quantitative Trait Loci using bulk segregants unveils a novel determinant of high ethanol tolerance in yeast. *BMC Genomics* 15, 207 (2014).
9. Schlotterer, C., Tobler, R., Kofler, R. & Nolte, V. Sequencing pools of individuals—mining genome-wide polymorphism data without big funding. *Nat Rev Genet* 15, 749-63 (2014).
10. Swinnen, S. et al. Identification of novel causative genes determining the complex trait of high ethanol tolerance in yeast using pooled-segregant whole-genome sequence analysis. *Genome Res* 22, 975-84 (2012).
11. Wilkening, S. et al. An evaluation of high-throughput approaches to QTL mapping in *Saccharomyces cerevisiae*. *Genetics* 196, 853-65 (2014).
12. Pais, T. M. et al. Comparative polygenic analysis of maximal ethanol accumulation capacity and tolerance to high ethanol levels of cell proliferation in yeast. *PLoS Genet* 9, e1003548 (2013).
13. Darvasi, A. & Soller, M. Advanced intercross lines, an experimental population for fine genetic mapping. *Genetics* 141, 1199-207 (1995).
14. Long, A., Liti, G., Luptak, A. & Tenaillon, O. Elucidating the molecular architecture of adaptation via evolve and resequence experiments. *Nat Rev Genet* 16, 567-82 (2015).
15. Parts, L. et al. Revealing the genetic structure of a trait by sequencing a population under selection. *Genome Res* 21, 1131-8 (2011).
16. Cubillos, F. A. et al. High-resolution mapping of complex traits with a four-parent advanced intercross yeast population. *Genetics* 195, 1141-55 (2013).
17. Ezov, T. K. et al. Molecular-genetic biodiversity in a natural population of the yeast *Saccharomyces cerevisiae* from "Evolution Canyon": microsatellite polymorphism, ploidy and controversial sexual status. *Genetics* 174, 1455-68 (2006).
18. Liti, G. et al. Population genomics of domestic and wild yeasts. *Nature* 458, 337-41 (2009).
19. Chang, S. L. & Leu, J. Y. A tradeoff drives the evolution of reduced metal resistance in natural populations of yeast. *PLoS Genet* 7, e1002034 (2011).
20. Lebowitz, M. D. et al. Vectorcardiographic and blood pressure correlates of obstructive pulmonary diseases in a community population. *Chest* 89, 78-84 (1986).
21. Bahalul, M., Kaneti, G. & Kashi, Y. Ether-zymolyase ascospore isolation procedure: an efficient protocol for ascospores isolation in *Saccharomyces cerevisiae* yeast. *Yeast* 27, 999-1003 (2010).
22. W. S. Cleveland, E. G. a. W. M. S. Local regression models. in *Statistical models* in *S* (ed. Hastie, C. a. T. J.) (Wadsworth & Brooks/Cole Advanced Books & Software, Pacific Grove, Calif., 1992).
23. Lipkin, E. et al. The Use of Kosher Phenotyping for Mapping QTL Affecting Susceptibility to Bovine Respiratory Disease. *PLoS ONE* 11, e0153423 (2016).
24. Spjotvoll, T. S. E. Plots of P-values to evaluate many tests simultaneously. *Biometrika* 69, 493-502 (1982).
25. Mosig, M. O. et al. A whole genome scan for quantitative trait loci affecting milk protein percentage in Israeli-Holstein cattle, by means of selective milk DNA pooling in a daughter design, using an adjusted false discovery rate criterion. *Genetics* 157, 1683-98 (2001).
26. Weller, J. I. & Soller, M. An analytical formula to estimate confidence interval of QTL location with a saturated genetic map as a function of experimental design. *Theor Appl Genet* 109, 1224-9 (2004).
27. Cherry, J. M. et al. *Saccharomyces* Genome Database: the genomics resource of budding yeast. *Nucleic Acids Res* 40, D700-5 (2012).
28. Snoek, T., Verstrepen, K J. & Voordeckers, K. How do yeast cells become tolerant to high ethanol concentrations? *Curr Genet* 62, 475-80 (2016).
29. Wood, A. R. et al. Defining the role of common variation in the genomic and biological architecture of adult human height. *Nat Genet* 46, 1173-86 (2014).
30. Kubota, S. et al. Effect of ethanol on cell growth of budding yeast: genes that are important for cell growth in the presence of ethanol. *Biosci Biotechnol Biochem* 68, 968-72 (2004).

31. Finn, R. D. et al. The Pfam protein families database: towards a more sustainable future. *Nucleic Acids Res* 44, D279-85 (2016).
32. Qian, W., Ma, D., Xiao, C., Wang, Z. & Zhang, J. The genomic landscape and evolutionary resolution of antagonistic pleiotropy in yeast. *Cell Rep* 2, 1399-410 (2012).
33. Chandler, M., Stanley, G., Rogers, P. & Chambers, P. A genomic approach to defining the ethanol stress response in the yeast *Saccharomyces cerevisiae. Ann Microbiol* 54, 427-454 (2004).
34. Yoshikawa, K. et al. Comprehensive phenotypic analysis for identification of genes affecting growth under ethanol stress in *Saccharomyces cerevisiae. FEMS Yeast Res* 9, 32-44 (2009).
35. Steinmetz, L. M. et al. Systematic screen for human disease genes in yeast. *Nat Genet* 31, 400-4 (2002).
36. Takemura, R., Inoue, Y. & Izawa, S. Stress response in yeast mRNA export factor: reversible changes in Rat8p localization are caused by ethanol stress but not heat shock. *J Cell Sci* 117, 4189-97 (2004).
37. Saavedra, C., Tung, K. S., Amberg, D. C., Hopper, A. K. & Cole, C. N. Regulation of mRNA export in response to stress in *Saccharomyces cerevisiae. Genes Dev* 10, 1608-20 (1996).
38. Lam, F. H., Ghaderi, A., Fink, G. R. & Stephanopoulos, G. Biofuels. Engineering alcohol tolerance in yeast. *Science* 346, 71-5 (2014).
39. Stanley, D., Chambers, P. J., Stanley, G. A., Borneman, A. & Fraser, S. Transcriptional changes associated with ethanol tolerance in *Saccharomyces cerevisiae. Appl Microbiol Biotechnol* 88, 231-9 (2010).
40. Cubillos, F. A. Exploiting budding yeast natural variation for industrial processes. *Curr Genet* 62, 745-751 (2016).
41. Judd, S. R. & Petes, T. D. Physical lengths of meiotic and mitotic gene conversion tracts in *Saccharomyces cerevisiae. Genetics* 118, 401-10 (1988).
42. Link, A J. & Olson, M. V. Physical map of the *Saccharomyces cerevisiae* genome at 110-kilobase resolution. *Genetics* 127, 681-98 (1991).
43. Andrews, S. FastQC: a quality control tool for high throughput sequence data. (Babraham Bioinformatics, worldwideweb(dot)bioinformatics(dot)babraham(dot)acdotuk/projects/fastqc/, 2010).
44. Hernandez, D., Francois, P., Farinelli, L., Osteras, M. & Schrenzel, J. De novo bacterial genome sequencing: millions of very short reads assembled on a desktop computer. *Genome Res* 18, 802-9 (2008).
45. Bao, E., Jiang, T. & Girke, T. AlignGraph: algorithm for secondary de novo genome assembly guided by closely related references. *Bioinformatics* 30, i319-i328 (2014).
46. Li, H. & Durbin, R. Fast and accurate short read alignment with Burrows-Wheeler transform. *Bioinformatics* 25, 1754-60 (2009).
47. McKenna, A. et al. The Genome Analysis Toolkit: a MapReduce framework for analyzing next-generation DNA sequencing data. *Genome Res* 20, 1297-303 (2010).
48. Kurtz, S. et al. Versatile and open software for comparing large genomes. *Genome Biol* 5, R12 (2004).
49. Sean Taylor, R. S., Richard Kurts, Carl Fisher, Viresh Patel and Frank Bizouam. A Practical Guide To High Resolution Melt Analysis Genotyping. in Hercules Calif. Vol. 6004 (ed. Laboratories, B.-R.) (Bulletin, 2010).
50. Bertels, F., Silander, O. K., Pachkov, M., Rainey, P. B. & van Nimwegen, E. Automated reconstruction of whole-genome phylogenies from short-sequence reads. *Mol Biol Evol* 31, 1077-88 (2014).
51. Bagnato, A. et al. Quantitative trait loci affecting milk yield and protein percentage in a three-country Brown Swiss population. *J Dairy Sci* 91, 767-83 (2008).
52. Benjamini, Y. & Hochberg, Y. Controlling the False Discovery Rate: A Practical and Powerful Approach to Multiple Testing. *Journal of the Royal Statistical Society. Series B (Methodological)* 57, 289-300 (1995).
53. Zuberi, K. et al. GeneMANIA prediction server 2013 update. *Nucleic Acids Res* 41, W115-22 (2013).

Additional references cited in the application:

Arya, R., M. Mallik, and S. C. Lakhotia, 2007 Heat shock genes—integrating cell survival and death. J Biosci 32(3): 595-610.

Ashkenazy, H., et al., 2010 ConSurf 2010: calculating evolutionary conservation in sequence and structure of proteins and nucleic acids. Nucleic Acids Res 38(Web Server issue):W529-33.

Bernstein, F. C., et al. 1977 The Protein Data Bank: a computer-based archival file for macromolecular structures. J Mol Biol 112(3):535-42.

Bonner, J. J., S. Heyward, and D. L. Fackenthal, 1992 Temperature-dependent regulation of a heterologous transcriptional activation domain fused to yeast heat shock transcription factor. Mol Cell Biol 12(3):1021-30.

Bothast, R. J., and M. A. Schlicher, 2005 Biotechnological processes for conversion of corn into ethanol. Appl Microbiol Biotechnol 67(1):19-25.

Celniker, Gershon, et al., 2013 ConSurf: Using Evolutionary Data to Raise Testable Hypotheses about Protein Function. Israel Journal of Chemistry 53(3-4):199-206.

Darvasi, A., and M. Soller, 1994 Selective DNA pooling for determination of linkage between a molecular marker and a quantitative trait locus. Genetics 138(4):1365-73.

de Smidt, O., J. C. du Preez, and J. Albertyn, 2012 Molecular and physiological aspects of alcohol dehydrogenases in the ethanol metabolism of *Saccharomyces cerevisiae*. FEMS Yeast Res 12(1):33-47.

Ehrenreich, I. M., et al., 2010 Dissection of genetically complex traits with extremely large pools of yeast segregants. Nature 464(7291):1039-42.

Elledge, S. J., and R. W. Davis, 1987 Identification and isolation of the gene encoding the small subunit of ribonucleotide reductase from *Saccharomyces cerevisiae*: DNA damage-inducible gene required for mitotic viability. Mol Cell Biol 7(8):2783-93.

Estruch, F., 2000 Stress-controlled transcription factors, stress-induced genes and stress tolerance in budding yeast. FEMS Microbiol Rev 24(4):469-86.

Fernandez-Recio, J., et al., 2005 Optimal docking area: a new method for predicting protein-protein interaction sites. Proteins 58(1):134-43.

Hu, X. H., et al., 2007 Genetic dissection of ethanol tolerance in the budding yeast *Saccharomyces cerevisiae*. Genetics 175(3):1479-87.

Ida, Y., et al., 2012 Stable disruption of ethanol production by deletion of the genes encoding alcohol dehydrogenase isozymes in *Saccharomyces cerevisiae*. J Biosci Bioeng 113(2):192-5.

Kelley, L. A., et al., 2015 The Phyre2 web portal for protein modeling, prediction and analysis. Nat Protoc 10(6):845-58.

Manolio, T. A., et al., 2009 Finding the missing heritability of complex diseases. Nature 461(7265):747-53.

Mosig, M. O., et al., 2001 A whole genome scan for quantitative trait loci affecting milk protein percentage in Israeli-Holstein cattle, by means of selective milk DNA pooling in a daughter design, using an adjusted false discovery rate criterion. Genetics 157(4): 1683-98.

Pires, D. E., D. B. Ascher, and T. L. Blundell, 2014 DUET: a server for predicting effects of mutations on protein stability using an integrated computational approach. Nucleic Acids Res 42(Web Server issue):W314-9.

Quan, X., et al. 2004 Regulated nuclear accumulation of the yeast hsp70 Ssa4p in ethanol-stressed cells is mediated by the N-terminal domain, requires the nuclear carrier Nmd5p and protein kinase C. FASEB J 18(7):899-901.

Robinson, M. D., et al., 2002 FunSpec: a web-based cluster interpreter for yeast. BMC Bioinformatics 3:35.

Rouillon, A., Y. Surdin-Kerjan, and D. Thomas, 1999 Transport of sulfonium compounds. Characterization of the s-adenosylmethionine and s-methylmethionine permeases from the yeast *Saccharomyces cerevisiae*. J Biol Chem 274(40):28096-105.

Roy, A., A. Kucukural, and Y. Zhang, 2010 I-TASSER: a unified platform for automated protein structure and function prediction. Nat Protoc 5(4):725-38.

Sikkema, J., J. A. de Bont, and B. Poolman, 1995 Mechanisms of membrane toxicity of hydrocarbons. Microbiol Rev 59(2):201-22.

Snoek, T., K. J. Verstrepen, and K. Voordeckers, 2016 How do yeast cells become tolerant to high ethanol concentrations? Curr Genet 62(3):475-80.

Steinmetz, L. M., et al. 2002 Dissecting the architecture of a quantitative trait locus in yeast. Nature 416(6878):326-30.

Swinnen, S., et al., 2012 Identification of novel causative genes determining the complex trait of high ethanol tolerance in yeast using pooled-segregant whole-genome sequence analysis. Genome Res 22(5):975-84.

Yang, J., et al., 2015 The I-TASSER Suite: protein structure and function prediction. Nat Methods 12(1):7-8.

Ye W, Zhang W, Liu T, Tan G, Li H, Huang Z. 2016. Improvement of Ethanol Production in *Saccharomyces cerevisiae* by High-Efficient Disruption of the ADH2 Gene Using a Novel Recombinant TALEN Vector. Front Microbiol 7:1067. Cubillos F A, Billi E, Zorgo E, Parts L, Fargier P, Omholt S, Blomberg A, Warringer J, Louis E J, Liti G. 2011. Assessing the complex architecture of polygenic traits in diverged yeast populations. Mol Ecol 20:1401-1413.

LENGTHY TABLES

The patent contains a lengthy table section. A copy of the table is available in electronic form from the USPTO web site (https://seqdata.uspto.gov/?pageRequest=docDetail&DocID=US11692166B2). An electronic copy of the table will also be available from the USPTO upon request and payment of the fee set forth in 37 CFR 1.19(b)(3).

What is claimed is:

1. A yeast strain of the species *Saccharomyces cerevisiae* being capable of surviving 15% (V/V) ethanol stress for at least 5 hours and capable of propagating under 9.5% (V/V) ethanol stress for at least 22 hours, the strain having a mutation of A to G in YJR154W gene at position 726,760 of chromosome 10.

2. The yeast strain of claim 1, having an additional mutation in at least one gene selected from the group consisting of alcohol dehydrogenase-2 (ADH2), Multicopy suppressor Of is Gsp1 (MOG1), ReTroGrade regulation2 (RTG2), Maintenance of genome stability 1 (MGS1), Zinc-Regulated Transporter1 (ZRT1), RiboNucleotide Reductase (RNR2) and S-MethylMethionine Permease (MMP1).

3. The yeast strain of claim 1, being capable of propagating at a temperature above 30° C.

4. The yeast strain of claim 1, being capable of propagating in a medium comprising an amount of sugar above 5%.

5. A yeast strain, being a progeny of the yeast strain of claim 1.

6. A culture comprising the yeast strain of claim 1 and a culture medium, wherein the percentage of ethanol in said medium is from about 5% (V/V) to about 50% (V/V).

7. The culture of claim 6, wherein the medium comprises a liquid medium.

8. The culture of claim 7, wherein said liquid medium comprises yeast extract peptone dextrose (YPD).

9. The culture of claim 6, wherein said medium further comprises a carbon source.

10. The culture of claim 9, wherein said carbon source is glucose.

11. The culture of claim 9, wherein said carbon source is a waste product.

12. A food, beverage or animal feed comprising the yeast strain of claim 1.

* * * * *